US008481531B2

(12) United States Patent
Saxty et al.

(10) Patent No.: US 8,481,531 B2
(45) Date of Patent: Jul. 9, 2013

(54) BICYCLIC HETEROCYCLYL DERIVATIVES AS FGFR KINASE INHIBITORS FOR THERAPEUTIC USE

(75) Inventors: Gordon Saxty, Cambridge (GB); Valerio Berdini, Cambridge (GB); Eddy Jean Edgard Freyne, Rumst (BE); Alexandra Papanikos, Antwerp (BE); Pascal Benderitter, Orbe (CH); Werner Constant Johan Embrechts, Beerse (BE); Berthold Wroblowski, Vosselaar (BE); Rhalid Akkari, Vacquières (FR)

(73) Assignee: Astex Therapeutics Ltd, Cambridge (GB)

( * ) Notice: Subject to any disclaimer, the term of this patent is extended or adjusted under 35 U.S.C. 154(b) by 0 days.

(21) Appl. No.: 13/264,593

(22) PCT Filed: Apr. 15, 2010

(86) PCT No.: PCT/GB2010/050617
§ 371 (c)(1),
(2), (4) Date: Oct. 14, 2011

(87) PCT Pub. No.: WO2010/119284
PCT Pub. Date: Oct. 21, 2010

(65) Prior Publication Data
US 2012/0035171 A1     Feb. 9, 2012

Related U.S. Application Data

(60) Provisional application No. 61/169,487, filed on Apr. 15, 2009.

(30) Foreign Application Priority Data

Apr. 15, 2009  (GB) .................................. 0906472.6

(51) Int. Cl.
| | |
|---|---|
| *A61K 31/5377* | (2006.01) |
| *A61K 31/437* | (2006.01) |
| *A61K 31/496* | (2006.01) |
| *C07D 413/02* | (2006.01) |
| *C07D 471/04* | (2006.01) |
| *C07D 401/02* | (2006.01) |
| *C07D 239/20* | (2006.01) |

(52) U.S. Cl.
USPC ................ 514/233.2; 514/253.04; 514/256; 514/300; 544/127; 544/333; 544/362; 546/121

(58) Field of Classification Search
USPC .......... 514/233.2, 253.04, 256, 300; 544/127, 544/333, 362; 546/121
See application file for complete search history.

(56) References Cited

U.S. PATENT DOCUMENTS

| | | |
|---|---|---|
| 5,554,630 A | 9/1996 | Teuber et al. |
| 5,990,146 A | 11/1999 | Boschelli et al. |
| 6,465,484 B1 | 10/2002 | Bilodeau et al. |
| 6,498,165 B1 | 12/2002 | Armstrong et al. |
| 6,855,719 B1 | 2/2005 | Thomas et al. |
| 7,074,801 B1 | 7/2006 | Yoshida et al. |
| 8,071,614 B2 | 12/2011 | Saxty et al. |
| 8,076,354 B2 | 12/2011 | Saxty et al. |
| 8,131,527 B1 | 3/2012 | Saxty et al. |
| 2002/0041880 A1 | 4/2002 | DeFeo-Jones et al. |
| 2003/0203897 A1 | 10/2003 | Love et al. |
| 2004/0019210 A1 | 1/2004 | Chivikas Connolly et al. |
| 2004/0067948 A1 | 4/2004 | Hallett |
| 2004/0220189 A1 | 11/2004 | Sun et al. |
| 2004/0267510 A1 | 12/2004 | Bemis et al. |
| 2006/0035921 A1 | 2/2006 | Castelhano et al. |
| 2006/0089362 A1 | 4/2006 | Seno et al. |
| 2006/0116402 A1 | 6/2006 | Crew et al. |
| 2006/0189629 A1 | 8/2006 | Bolger et al. |
| 2007/0185140 A1 | 8/2007 | Bordon-Pallier et al. |
| 2008/0139606 A1 | 6/2008 | Tabart et al. |
| 2008/0167314 A1 | 7/2008 | Uchikawa et al. |

FOREIGN PATENT DOCUMENTS

| | | |
|---|---|---|
| EP | 1382603 A1 | 1/2004 |
| EP | 1724258 A1 | 11/2006 |
| EP | 1748048 A1 | 1/2007 |
| EP | 1790650 A1 | 5/2007 |
| EP | 1882475 A1 | 1/2008 |
| EP | 2116543 A1 | 11/2009 |
| JP | 2001-057292 | 2/2001 |
| JP | 2004-002826 | 1/2004 |
| WO | 9535296 A1 | 12/1995 |
| WO | 96/34866 A1 | 11/1996 |
| WO | 97/12613 A1 | 4/1997 |
| WO | 98/03510 A1 | 1/1998 |
| WO | 98/54093 A1 | 12/1998 |
| WO | 99/38868 A1 | 8/1999 |
| WO | 00/12089 A1 | 3/2000 |
| WO | 00/53605 A1 | 9/2000 |
| WO | 01/00207 A1 | 1/2001 |
| WO | 01/00213 A1 | 1/2001 |
| WO | 01/00214 A1 | 1/2001 |
| WO | 01/14375 A1 | 3/2001 |
| WO | 01/18000 A1 | 3/2001 |
| WO | 01/21634 A1 | 3/2001 |
| WO | 01/38326 A2 | 5/2001 |
| WO | 01/66098 A2 | 9/2001 |
| WO | 02/12238 A2 | 2/2002 |
| WO | 02/34748 A1 | 5/2002 |
| WO | 02/38569 A1 | 5/2002 |

(Continued)

OTHER PUBLICATIONS

Search Report for GB0625827.1 dated Apr. 25, 2007.

(Continued)

*Primary Examiner* — Samantha Shterengarts
(74) *Attorney, Agent, or Firm* — Heslin Rothenberg Farley & Mesiti P.C.

(57) ABSTRACT

The invention relates to new bicyclic heterocyclyl derivatives of formula (I), to pharmaceutical compositions comprising said compounds and to the use of said compounds in the treatment of diseases, e.g. cancer.

20 Claims, No Drawings

FOREIGN PATENT DOCUMENTS

| | | |
|---|---|---|
| WO | 02/46168 A1 | 6/2002 |
| WO | 02/066477 A2 | 8/2002 |
| WO | 02/066478 A1 | 8/2002 |
| WO | 02/066480 A2 | 8/2002 |
| WO | 02/066481 A1 | 8/2002 |
| WO | 02/074773 A1 | 9/2002 |
| WO | 02/080914 A2 | 10/2002 |
| WO | 03/007955 A2 | 1/2003 |
| WO | 03/048132 A1 | 6/2003 |
| WO | 03/050117 A1 | 6/2003 |
| WO | 03/050119 A2 | 6/2003 |
| WO | 03/082208 A2 | 10/2003 |
| WO | 03/092595 A2 | 11/2003 |
| WO | 03/099811 A1 | 12/2003 |
| WO | 03/099816 A1 | 12/2003 |
| WO | 03/099817 A1 | 12/2003 |
| WO | 03/101993 A1 | 12/2003 |
| WO | 2004/026867 A2 | 4/2004 |
| WO | 2004/035579 A1 | 4/2004 |
| WO | 2004/052286 A2 | 6/2004 |
| WO | 2004/052315 A2 | 6/2004 |
| WO | 2004/087153 A2 | 10/2004 |
| WO | 2005/021531 A1 | 3/2005 |
| WO | 2005/021544 A2 | 3/2005 |
| WO | 2005/054230 A1 | 6/2005 |
| WO | 2005/075470 A1 | 8/2005 |
| WO | 2006/000420 A1 | 1/2006 |
| WO | 2006/034402 A2 | 3/2006 |
| WO | 2006/038001 A1 | 4/2006 |
| WO | 2006/070198 A1 | 7/2006 |
| WO | 2006/070943 A1 | 7/2006 |
| WO | 2006/091671 A1 | 8/2006 |
| WO | 2006/094235 A1 | 9/2006 |
| WO | 2006/108103 A1 | 10/2006 |
| WO | 2006/135667 A1 | 12/2006 |
| WO | 2007/036732 A1 | 4/2007 |
| WO | 2007/109362 A2 | 9/2007 |
| WO | 2007/112093 A2 | 10/2007 |
| WO | 2008/003511 A1 | 1/2008 |
| WO | 2008/008747 A1 | 1/2008 |
| WO | 2008/075068 A2 | 6/2008 |
| WO | 2008/078091 A1 | 7/2008 |
| WO | 2008/078100 A2 | 7/2008 |
| WO | 2008/081910 A1 | 7/2008 |
| WO | 2008/124323 A1 | 10/2008 |
| WO | 2008/154642 A2 | 12/2008 |
| WO | 2009/002534 A1 | 12/2008 |
| WO | 2009/047506 A1 | 4/2009 |
| WO | 2009/047522 A1 | 4/2009 |
| WO | 2009/150240 A1 | 12/2009 |
| WO | 2010/119284 A1 | 10/2010 |
| WO | 2010/119285 A1 | 10/2010 |

OTHER PUBLICATIONS

Search Report for GB0719998.7 dated Nov. 12, 2007.
Search Report for PCT/GB2007/004960 dated Sep. 22, 2008.
Search Report for GB0625826.3 dated Apr. 25, 2007.
Search Report for GB0720000.9 dated Nov. 12, 2007.
Search Report for PCT/GB2007/004934 dated May 6, 2008.
Search Report for GB0810902.7 dated Sep. 17, 2008.
Search Report for PCT/EP2009/057318 dated Oct. 12, 2009.
Search Report for GB0720038.9 dated Apr. 17, 2008.
Search Report for PCT/GB2008/003439 dated Jan. 29, 2009.
Search Report for GB0720041.3 dated Apr. 17, 2008.
Search Report for PCT/GB2008/003418 dated Jan. 29, 2009.
Search Report for GB0906472.6 dated Jul. 7, 2009.
Search Report for PCT/GB2010/050617 dated Jul. 20, 2010.
Search Report for GB0906470.0 dated Jul. 8, 2009.
Search Report for PCT/GB2010/050618 dated Jul. 23, 2010.
Bilodeau, Mark T. et al., Design and Synthesis of 1,5-Dairylbenzimidazoles as Inhibitors of the VEGF-Receptor KDR, Bioorganic & Medicinal Chemistry Letters 13, 2003, pp. 2485-2488.
Clark, Michael P. et al., Development of new pyrrolopyrimidine-based inhibitors of Janus kinase 3 (JAK3), Bioorganic & Medicinal Chemistry Letters 17 (5), 2007, pp. 1250-1253.
Wermuth, Camille G., Molecular Variations Based on Isosteric Replacements, The Practice of Medicinal Chemistry, 1996, pp. 203-237.
Fraley, Mark E. et al., Synthesis and Initial SAR Studies of 3,6-Disubstituted Pyrazolo[1,5-*a*]pyrimidines: A New Class of KDR Kinase Inhibitors, Bioorganic & Medicinal Chemistry Letters 12, 2002, pp. 2767-2770.
Wu, Zhicai et al., Design and Synthesis of 3,7-diarylimidazopyridines as inhibitors of the VEGF-receptor KDR, Bioorganic & Medicinal Chemistry Letters 14, 2004, pp. 909-912.
Fraley, Mark E. et al., Optimization of a Pyrazolo[1,5-*a*]pyrimidine Class of KDR Kinase Inhibitors: Improvements in Physical Properties Enhance Cellular Activity and Pharmacokinetics, Bioorganic & Medicinal Chemistry Letters 12, 2002, pp. 3537-3541.
Skaper, Stephen D. et al., The FGFR1 Inhibitor PD 173074 Selectively and Potently Antagonizes FGF-2 Neurotrophic and Neurotropic Effects, Journal of Neurochemistry, 2000, pp. 1520-1527.
Mohammadi, Moosa et al., Crystal structure of an angiogenesis inhibitor bound to the FGR receptor tyrosine kinase domain, The EMBO Journal, vol. 17, No. 20, 1998, pp. 5896-5904.
Connolly, Cleo J.C. et al., Discovery and Structure-Activity Studies of a Novel Series of Pyrido[2,3-*d*]Pyrimidine Tyrosine Kinase Inhibitors, Bioorganic & Medicinal Chemistry Letters, vol. 7, No. 18, 1997, pp. 2415-2420.
Hamby, James M. et al., Structure-Activity Relationships for a Novel Series of Pyrido[2,3-*d*]pyrimidine Tyrosine Kinase Inhibitors, J. Med. Chem, 40, 1997, pp. 2296-2303.
Scribner, Andrew et al., Synthesis and biological activity of imidazopyridine anticoccidial agents: Part I, European Journal of Medicinal Chemistry 42, 2007, pp. 1334-1357.
Anderson, Malcolm et al., Imidazo[1,2-*a*]pyridines: A Potent and Selective Class of Cyclin-Dependent Kinase Inhibitors Identified Through Structure-Based Hybridisation, Bioorganic & Medicinal Chemistry Letters 13, 2003, pp. 3021-3026.
Mohammadi, Moosa et al., Structures of the Tyrosine Kinase Domain of Fibroblast Growth Factor Receptor in Complex with Inhibitors, Science, 276, 1997, pp. 955-960.
Dorwald, F. Zaragoza, Side Reactions in Organic Synthesis, 2005, Wiley: VCH, Weinheim p. IX of Preface.
Vippagunta, Sudha R., et al., Crystalline solids, Advanced Drug Delivery Reviews 48, 2001, pp. 3-26.
West, Anthony R., Solid state chemistry and its applications, Department of Chemistry, University of Aberdeen, 1988, pp. 358 and 365.
Hamdi et al. "Solvates of Indomethacin"; *Journal of Thermal Analysis and Calorimetry*; 2004; pp. 985-1001; vol. 76.
Morissette et al. "High-throughput crystallization: polymorphs, salts, co-crystals and solvates of pharmaceutical solids"; *Advanced Drug Delivery Reviews*; 2004; pp. 275-300; vol. 56.
Palmer, Brian D., et al."Structure-Activity Relationships for 1-Phenylbenzimidazoles as Selective ATP Site Inhibitors of the Platelet-Derived Growth Factor Receptor" *Journal of Medicinal Chemistry*, 1998, 41 (27), pp. 5457-5465.

US 8,481,531 B2

BICYCLIC HETEROCYCLYL DERIVATIVES AS FGFR KINASE INHIBITORS FOR THERAPEUTIC USE

CROSS REFERENCE TO RELATED APPLICATIONS

This application is a national stage filing under section 371 of International Application No. PCT/GB2010/050617, filed on Apr. 15, 2010, and published in English on Oct. 21, 2010, as WO 2010/119284, and claims priority to British Application No. 0906472.6 filed on Apr. 15, 2009, and to U.S. Provisional Application No. 61/169,487, filed on Apr. 15, 2009. The entire disclosures of each of the prior applications are hereby incorporated herein by reference.

FIELD OF THE INVENTION

The invention relates to new bicyclic heterocyclyl derivative compounds, to pharmaceutical compositions comprising said compounds and to the use of said compounds in the treatment of diseases, e.g. cancer.

SUMMARY OF THE INVENTION

According to a first aspect of the invention there is provided a compound of formula (I):

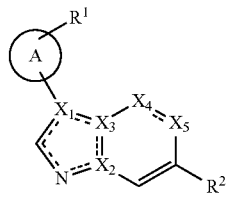

(I)

wherein
$X_1$, $X_2$ and $X_3$ are each independently selected from carbon or nitrogen, such that at least one of $X_1$-$X_3$ represents nitrogen;
$X_4$ represents $CR^3$, nitrogen, NH or C=O;
$X_5$ represents $CR^6$, nitrogen, NH or C=O;
provided that no more than three of $X_1$-$X_5$ represent nitrogen;
------ represents a single or double bond, such that when $X_5$ represents C=O, $X_4$ and $X_5$ are joined by a single bond and such that at least one bond within the 5 membered ring system is a double bond;
$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy, amino, or —$C_{1-6}$alkylamino;
$R^6$ represents halogen, hydrogen, $C_{1-6}$ alkyl, $C_{1-6}$ alkoxy, $C_{2-6}$ alkenyl, $C_{2-6}$ alkynyl, —C≡N, $C_{3-8}$ cycloalkyl, $C_{3-8}$ cycloalkenyl, —NHSO$_2$R$^w$, —CH=N—OR$^w$, or a 3-6 membered monocyclic heterocyclyl group wherein said $C_{1-6}$ alkyl, $C_{2-6}$ alkenyl, $C_{2-6}$ alkynyl, $C_{1-6}$alkoxy and heterocyclyl groups may be optionally substituted by one or more $R^a$ groups;
A represents an aromatic or non-aromatic carbocyclyl or heterocyclyl group which may be optionally substituted by one or more (e.g. 1, 2 or 3) $R^a$ groups;
$R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$NR$^4$R$^5$, —NHCSNR$^4$R$^5$, —NHCOR$^4$, —NHCSR$^4$, —NHCSSR$^4$, —NHC(=NR$^4$)NR$^4$R$^5$, —NHC(=N—CN)NR$^4$R$^5$, —NHC(=NR$^4$)R$^5$, —NH—C(=NH)—NH—CO—R$^4$, —NHCSOR$^4$, —NH-COSR$^4$ or an NH-heterocyclyl group wherein the heterocyclyl group represents thiadiazolyl or oxadiazolyl and the heterocyclyl group may be optionally substituted by one or more (e.g. 1, 2 or 3) $R^a$ groups;
$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—CO—OR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;
$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —(CH$_2$)$_n$—OH, —(CH$_2$)$_n$—O—$C_{1-6}$alkyl, —CO—(CH$_2$)$_n$—$C_{1-6}$ alkoxy, —(CH$_2$)$_s$—CN, —$C_{1-6}$ alkylamino, —$C_{1-6}$ alkyl-N($C_{1-6}$ alkyl)$_2$, —$C_{1-6}$ alkyl-NH($C_{1-6}$ alkyl), —(CH$_2$)$_n$—$C_{3-8}$ cycloalkyl, amino, -amino$C_{1-6}$ alkyl, -amino($C_{1-6}$ alkyl)$_2$, —(CH$_2$)$_s$—NH—SO$_2$—N($C_{1-6}$alkyl)$_q$, —(CH$_2$)$_s$—N($C_{1-4}$ alkyl)-SO$_2$—N($C_{1-6}$alkyl)$_q$, —(CH$_2$)$_s$—O—C(=O)—$C_{1-4}$ alkyl-N($C_{1-6}$alkyl)$_q$, —(CH$_2$)$_s$—$C_{3-8}$ cycloalkenyl, or when attached to nitrogen or carbon atom $R^x$ and $R^y$ can form a ring;
$R^2$ represents a —CR$^v$=N—OR$^w$ group;
$R^v$ and $R^w$ independently represent hydrogen or $R^b$;
$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^x$, —(CH$_2$)$_n$—O—R$^x$, —O—(CH$_2$)$_n$—OR$^x$, halo$C_{1-6}$ alkyl, halo$C_{1-6}$ alkoxy, $C_{1-6}$ alkanol, =O, =S, nitro, —Si(R$^x$)$_4$, —(CH$_2$)$_s$—CN, —S—R$^x$, SO—R$^x$, —SO$_2$—R$^x$, —COR$^x$, aryl, heterocyclyl group, —(CR$^x$R$^y$)$_s$—COOR$^z$, —(CR$^x$R$^y$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$—(CH$_2$)$_s$—SO$_2$—R$^y$, —NR$^x$—(CH$_2$)$_s$—R$^z$, —(CH$_2$)$_s$—O—C(=O)—$C_{1-4}$alkyl-NR$^x$R$^y$, —(CH$_2$)$_s$—NR$^x$—(CH$_2$)$_n$—O—C(=O)—R$^z$, —(CR$^x$R$^y$)—O—C(=O)—R$^z$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$, —(CH$_2$)$_s$—SO$_2$NR$^x$R$^y$ or —NH—C(=NH)—NH$_2$; wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more $R^x$ groups;
$R^b$ represents a -Q-$R^a$ group or a —Y-carbocyclyl or —Z-heterocyclyl group wherein said carbocyclyl and heterocyclyl groups may be optionally substituted by one or more (e.g. 1, 2 or 3) $R^a$ groups;
Y and Z independently represent a direct bond, —CO—(CR$^x$R$^y$)$_s$—, —(CR$^x$R$^y$)$_s$—CO—, —COO—, —(CR$^x$R$^y$)$_n$—, —NR$^x$—(CR$^x$R$^y$)$_s$—, —(CR$^x$R$^y$)$_s$—NR$^x$—, —CONR$^x$—, —SO$_2$NR$^x$—, —NR$^x$CONR$^y$—, —NR$^x$CS-NR$^y$—, —(CR$^x$R$^y$)$_s$—O—, S—, —SO— or —(CR$^x$R$^y$)$_s$—SO$_2$—;
Q represents NR$^x$, S(O)$_q$ or a direct bond;
m and n independently represent an integer from 1-4;
s and t independently represent an integer from 0-4;
q represents an integer from 0-2;
wherein when $R^v$ represents hydrogen, $R^w$ cannot represent hydrogen or —CH$_3$;
or a pharmaceutically acceptable salt, solvate or derivative thereof.

WO 2008/078100 (Astex), WO 2008/078091 (Astex), WO 2009/047522 (Astex), WO 2009/047506 (Astex), WO2009/150240 (Astex), US 2004/0067948 (MSD), WO 02/38569 (MSD), WO 01/38326 (MSD), U.S. Pat. No. 7,074,801 (Eisai), US 2002/0041880 (Merck), WO 98/54093 (Merck), WO 2006/091671 (Eli Lilly), WO 2003/048132 (Merck), WO 2004/052286 (Merck), WO 00/53605 (Merck), WO 03/101993 (Neogenesis), WO 2006/135667 (BMS), WO 2002/46168 & WO 2002/066478 (Astra Zeneca), WO 2005/080330 (Chugai), WO 2006/094235 (Sirtris Pharmaceuticals), WO 2006/034402 (Synta Pharmaceuticals), WO 02/074773 (Merck) and US 2004/067948 (Hallet) each disclose a series of heterocyclyl derivatives.

DETAILED DESCRIPTION OF THE INVENTION

According to a first aspect of the invention there is provided a compound of formula (I):

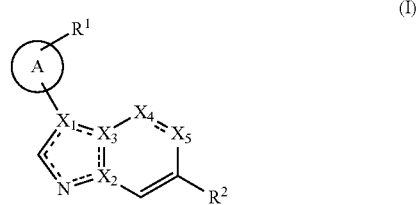

wherein
$X_1$, $X_2$ and $X_3$ are each independently selected from carbon or nitrogen, such that at least one of $X_1$-$X_3$ represents nitrogen;
$X_4$ represents $CR^3$, nitrogen, NH or C=O;
$X_5$ represents $CR^6$, nitrogen, NH or C=O;
provided that no more than three of $X_1$-$X_5$ represent nitrogen;
----- represents a single or double bond, such that when $X_5$ represents C=O, $X_4$ and $X_5$ are joined by a single bond and such that at least one bond within the 5 membered ring system is a double bond;
$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy, amino, or —$C_{1-6}$alkylamino;
$R^6$ represents halogen, hydrogen, $C_{1-6}$ alkyl, $C_{1-6}$ alkoxy, $C_{2-6}$ alkenyl, $C_{2-6}$ alkynyl, C≡N, $C_{3-8}$ cycloalkyl, $C_{3-8}$ cycloalkenyl, —NHSO$_2R^w$, —CH=N—OR$^w$, or a 3-6 membered monocyclic heterocyclyl group wherein said $C_{1-6}$ alkyl, $C_{2-6}$ alkenyl, $C_{2-6}$ alkynyl, $C_{1-6}$ alkoxy and heterocyclyl groups may be optionally substituted by one or more $R^a$ groups;
A represents an aromatic or non-aromatic carbocyclyl or heterocyclyl group which may be optionally substituted by one or more (e.g. 1, 2 or 3) $R^a$ groups;
$R^1$ represents —NHCONR$^4R^5$, —NHCOOR$^4$, —NH—CO—(CH$_2$)$_n$—NR$^4R^5$, —NH—(CH$_2$)$_n$—CONR$^4R^5$, —NH—CO—(CH$_2$)$_n$—COOR$^4$, —NH—CO—(CH$_2$)$_n$—CSOR$^4$, —NHSO$_2R^4$, —NHSO$_2$NR$^4R^5$, —NHCSNR$^4R^5$, —NHCOR$^4$, —NHCSR$^4$, —NHCSSR$^4$, —NHC(=NR$^4$)NR$^4R^5$, —NHC(=N—CN)NR$^4R^5$, —NHC(=NR$^4$)R$^5$, —NH—C(=NH)—NH—CO—R$^4$, —NHCSOR$^4$, —NH-COSR$^4$ or an NH-heterocyclyl group wherein the heterocyclyl group represents thiadiazolyl or oxadiazolyl and the heterocyclyl group may be optionally substituted by one or more (e.g. 1, 2 or 3) $R^a$ groups;
$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^xR^y$, —(CH$_2$)$_s$—CO-OR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-6}$ cycloalkenyl, aryl and heterocyclyl groups may be optionally substituted by one or more (e.g. 1, 2 or 3) $R^a$ groups;
$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —(CH$_2$)$_n$—OH, —(CH$_2$)$_n$—O—$C_{1-6}$alkyl, —CO—(CH$_2$)$_n$—$C_{1-6}$ alkoxy, —(CH$_2$)$_s$—CN, —$C_{1-6}$ alkylamino, —$C_{1-6}$ alkyl-N($C_{1-6}$ alkyl)$_2$, —$C_{1-6}$ alkyl-NH($C_{1-6}$ alkyl), —(CH$_2$)$_s$—$C_{3-8}$ cycloalkyl, amino, -amino$C_{1-6}$ alkyl, -amino($C_{1-6}$ alkyl)$_2$, —(CH$_2$)$_s$—NH—SO$_2$—N($C_{1-6}$alkyl)$_q$, —(CH$_2$)$_s$—N($C_{1-4}$ alkyl)-SO$_2$—N($C_{1-6}$alkyl)$_q$, —(CH$_2$)$_s$—O—C(=O)—$C_{1-4}$ alkyl-N($C_{1-6}$alkyl)$_q$, —(CH$_2$)$_s$—$C_{3-8}$ cycloalkenyl, or when attached to nitrogen or carbon atom $R^x$ and $R^y$ can form a ring;
$R^2$ represents a —CR$^v$=N—OR$^w$ group;
$R^v$ and $R^w$ independently represent hydrogen or $R^b$;
$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^x$, —(CH$_2$)$_n$—O—R$^x$, —O—(CH$_2$)$_n$—OR$^x$, halo$C_{1-6}$ alkyl, halo$C_{1-6}$ alkoxy, $C_{1-6}$ alkanol, =O, =S, nitro, —Si(R$^x$)$_4$, —(CH$_2$)$_s$—CN, —S—R$^x$, —SO—R$^x$, —SO$_2$—R$^x$, —COR$^x$, aryl, heterocyclyl group, —(CR$^xR^y$)$_s$—COOR$^z$, —(CR$^xR^y$)$_s$—CONR$^xR^y$, —(CH$_2$)$_s$—NR$^xR^y$, —(CH$_2$)$_s$—NR$^xCOR^y$, —(CH$_2$)$_s$—NR$^x$—(CH$_2$)$_s$—SO$_2$—R$^y$, —NR$^x$—(CH$_2$)$_s$—R$^z$, —(CH$_2$)$_s$—O—C(=O)—$C_{1-4}$alkyl-NR$^xR^y$, —(CH$_2$)$_s$—NR$^x$—(CH$_2$)$_n$—O—C(=O)—R$^z$, —(CR$^xR^y$)—O—C(=O)—R$^z$, —(CH$_2$)$_s$—NH—SO$_2$—NR$^xR^y$, —OCONR$^xR^y$, —(CH$_2$)$_s$—NR$^xCO_2R^y$, —O—(CH$_2$)$_s$—CR$^xR^y$—(CH$_2$)$_t$—OR$^z$, —(CH$_2$)$_s$—SO$_2$NR$^xR^y$ or —NH—C(=NH)—NH$_2$ groups; wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more $R^x$ groups;
$R^b$ represents a -Q-$R^a$ group or a —Y-carbocyclyl or —Z-heterocyclyl group wherein said carbocyclyl and heterocyclyl groups may be optionally substituted by one or more (e.g. 1, 2 or 3) $R^a$ groups;
Y and Z independently represent a direct bond, —CO—(CR$^xR^y$)$_s$—, —(CR$^xR^y$)$_s$—CO—, —COO—, —(CR$^xR^y$)—, —NR$^x$—(CR$^xR^y$)$_s$—, —(CR$^xR^y$)$_s$—NR$^x$—, —CONR$^x$—, —NR$^xCO$—, —SO$_2$NR$^x$—, —NR$^xSO_2$—, —NR$^x$-CONR$^y$—, —NR$^xCSNR^y$—, —O—(CR$^xR^y$)$_s$—, —(CR$^xR^y$)$_s$—O—, S—, —SO— or —(CR$^xR^y$), —SO$_2$—;
Q represents NR$^x$, S(O)$_q$ or a direct bond;
m and n independently represent an integer from 1-4;
s and t independently represent an integer from 0-4;
q represents an integer from 0-2;
wherein when $R^v$ represents hydrogen, $R^w$ cannot represent hydrogen or —CH$_3$;
or a pharmaceutically acceptable salt, solvate or derivative thereof.

According to one particular aspect of the invention there is provided a compound of formula (Ia):

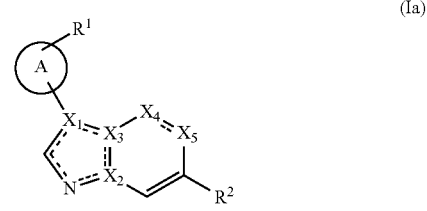

wherein $X_1$, $X_2$ and $X_3$ are each independently selected from carbon or nitrogen, such that at least one of $X_1$-$X_3$ represents nitrogen and such that when $X_1$ represents nitrogen, at least one of $X_2$, $X_3$, $X_4$ and $X_5$ is nitrogen;

$X_4$ represents $CR^3$, nitrogen, NH or C=O;

$X_5$ represents $CR^6$, nitrogen, NH or C=O;

provided that no more than three of $X_1$-$X_5$ represent nitrogen;

------ represents a single or double bond, such that the bond between $X_4$ and $X_5$ represents a single bond only when $X_4$ or $X_5$ represents C=O and such that at least one bond within the 5 membered ring system is a double bond;

$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy, amino, or —$C_{1-6}$alkylamino;

$R^6$ represents halogen, hydrogen, $C_{1-6}$ alkyl, $C_{1-6}$ alkoxy, $C_{2-6}$ alkenyl, $C_{2-6}$ alkynyl, C≡N, $C_{3-8}$ cycloalkyl, $C_{3-8}$ cycloalkenyl, —NHSO$_2$R$^w$, —CH=N—OR$^w$, or a 3-6 membered monocyclic heterocyclyl group wherein said $C_{1-6}$ alkyl, $C_{2-6}$ alkenyl, $C_{2-6}$ alkynyl, $C_{1-6}$ alkoxy and heterocyclyl groups may be optionally substituted by one or more $R^a$ groups;

A represents an aromatic or non-aromatic carbocyclyl or heterocyclyl group which may be optionally substituted by one or more (e.g. 1, 2 or 3) $R^a$ groups;

$R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$NR$^4$R$^5$, —NHCSNR$^4$R$^5$, —NHCOR$^4$, —NHCSR$^4$, —NHCSSR$^4$, —NHC(=NR$^4$)NR$^4$R$^5$, —NHC(=N—CN)NR$^4$R$^5$, —NHC(=NR$^4$)R$^5$, —NH—C(=NH)—NH—CO—R$^4$, —NHCSOR$^4$, —NH-COSR$^4$ or an NH-heterocyclyl group wherein the heterocyclyl group represents thiadiazolyl or oxadiazolyl and the heterocyclyl group may be optionally substituted by one or more (e.g. 1, 2 or 3) $R^a$ groups;

$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—CO-OR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;

$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —(CH$_2$)$_n$—OH, —CH$_2$)$_n$—O—$C_{1-6}$alkyl, —CO—(CH$_2$)$_n$—$C_{1-6}$ alkoxy, —(CH$_2$)$_s$—CN, —$C_{1-6}$ alkylamino, —$C_{1-6}$ alkyl-N(C$_{1-6}$ alkyl)$_2$, —$C_{1-6}$ alkyl-NH(C$_{1-6}$ alkyl), —(CH$_2$)$_s$C$_{3-8}$ cycloalkyl, amino, -amino$C_{1-6}$ alkyl, -amino(C$_{1-6}$ alkyl)$_2$, —(CH$_2$)$_s$—NH—SO$_2$—N(C$_{1-6}$alkyl)$_q$, —(CH$_2$)$_s$—N(C$_{1-4}$ alkyl)-SO$_2$—N(C$_{1-6}$alkyl)$_q$, —(CH$_2$)$_s$—O—C(=O)—C$_{1-4}$ alkyl-N(C$_{1-6}$alkyl)$_q$, —(CH$_2$)$_s$—C$_{3-8}$ cycloalkenyl, or when attached to nitrogen or carbon atom $R^x$ and $R^y$ can form a ring;

$R^2$ represents a —CR$^v$=N—OR$^w$ group;

$R^v$ and $R^w$ independently represent hydrogen or $R^b$;

$R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —OR$^x$, —(CH$_2$)$_n$—O—R$^x$, —O—(CH$_2$)$_n$—OR$^x$, halo$C_{1-6}$ alkyl, halo$C_{1-6}$ alkoxy, $C_{1-6}$ alkanol, =O, =S, nitro, —Si(R$^x$)$_4$, —(CH$_2$)$_s$—CN, —S—R$^x$, —SO—R$^x$, —SO$_2$—R$^x$, —COR$^x$, aryl, heterocyclyl group, —(CR$^x$R$^y$)$_s$—COOR$^z$, —(CR$^x$R$^y$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$—(CH$_2$)$_s$—SO$_2$—R$^y$, —NR$^x$—(CH$_2$)$_s$—R$^z$, —(CH$_2$)$_s$—NR$^x$—O—C(=O)—C$_{1-4}$alkyl-NR$^x$R$^y$, —(CH$_2$)$_s$—NR$^x$—(CH$_2$)$_n$—O—C(=O)—R$^z$, —(CR$^x$R$^y$)—O—C(=O)—R$^z$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$, —(CH$_2$)$_s$—SO$_2$NR$^x$R$^y$ or —NH—C(=NH)—NH$_2$ groups; wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more $R^x$ groups;

$R^b$ represents a -Q-$R^a$ group or a —Y-carbocyclyl or —Z-heterocyclyl group wherein said carbocyclyl and heterocyclyl groups may be optionally substituted by one or more (e.g. 1, 2 or 3) $R^a$ groups;

Y and Z independently represent a direct bond, —CO—(CR$^x$R$^y$)$_s$—, —(CR$^x$R$^y$)$_s$—CO—, —COO—, —(CR$^x$R$^y$)$_n$—, —NR$^x$—(CR$^x$R$^y$)$_s$—, —(CR$^x$R$^y$)$_s$—NR$^x$—, —CONR$^x$—, —NR$^x$CO—, —SO$_2$NR$^x$—, —NR$^x$SO$_2$—, —NR$^x$CONR$^y$—, —NR$^x$CSNR$^y$—, —O—(CR$^x$R$^y$)$_s$—, —(CR$^x$R$^y$)$_s$—O—, S—, —SO— or —(CR$^x$R$^y$)$_s$—SO$_2$—;

Q represents NR$^x$, S(O)$_q$ or a direct bond;

m and n independently represent an integer from 1-4;

s and t independently represent an integer from 0-4;

q represents an integer from 0-2;

wherein when $R^v$ represents hydrogen, $R^w$ cannot represent hydrogen or —CH$_3$;

or a pharmaceutically acceptable salt, solvate or derivative thereof.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

In each of the group (CR$^x$R$^y$)$_n$ or (CR$^x$R$^y$)$_s$ the $R^x$ and $R^y$ groups can each be independently selected from the definitions of $R^x$ and $R^y$ for each CR$^x$R$^y$ unit i.e. (CR$^x$R$^y$)$_n$ where n is 2, indicates CR$^x$R$^y$—CR$^x$R$^y$ and each of $R^x$ and $R^y$ are selected independently from each other and from each of $R^x$ and $R^y$ in the other unit.

The term '$C_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{2-6}$ alkenyl' as used herein as a group or a part of the group refers to a linear or branched hydrocarbon group containing a C=C bond.

The term '$C_{1-6}$ alkoxy' as used herein refers to an —O—$C_{1-6}$ alkyl group wherein $C_{1-6}$ alkyl is as defined herein. Examples of such groups include methoxy, ethoxy, propoxy, butoxy, pentoxy or hexoxy and the like.

The term '$C_{1-6}$ alkanol' as used herein refers to a $C_{1-6}$ alkyl group substituted by one or more hydroxy groups, wherein $C_{1-6}$ alkyl is as defined herein. Examples of such groups include hydroxymethyl, hydroxyethyl, hydroxypropyl and the like.

The term '$C_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-6}$ cycloalkyl' as used herein refers to a saturated monocyclic hydrocarbon ring of 3 to 6 carbon atoms. Examples of such groups include cyclopropyl, cyclobutyl, cyclopentyl, cyclohexyl, and the like.

The term 'halogen' as used herein refers to a fluorine, chlorine, bromine or iodine atom.

The term 'halo$C_{1-6}$ alkyl' as used herein refers to a $C_{1-6}$ alkyl group as defined herein wherein at least one hydrogen atom is replaced with halogen. Examples of such groups include fluoroethyl, trifluoromethyl or trifluoroethyl and the like.

The term 'haloC$_{1-6}$ alkoxy' as used herein refers to a C$_{1-6}$ alkoxy group as herein defined wherein at least one hydrogen atom is replaced with halogen. Examples of such groups include difluoromethoxy or trifluoromethoxy and the like.

References to "carbocyclyl" and "heterocyclyl" groups as used herein shall, unless the context indicates otherwise, include both aromatic and non-aromatic ring systems. Thus, for example, the term "carbocyclyl and heterocyclyl groups" includes within its scope aromatic, non-aromatic, unsaturated, partially saturated and fully saturated carbocyclyl and heterocyclyl ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Where reference is made herein to carbocyclyl and heterocyclyl groups, the carbocyclyl or heterocyclyl ring can, unless the context indicates otherwise, be unsubstituted or substituted by one or more substituents for example molecular fragments, molecular scaffolds or functional groups as discussed herein. It will be appreciated that references to "carbocyclyl" and "heterocyclyl" groups include reference to carbocyclyl and heterocyclyl groups which may be optionally substituted by one or more (e.g. 1, 2 or 3) R$^a$ or R$^b$ groups.

The carbocyclyl or heterocyclyl groups can be aryl or heteroaryl groups having from 5 to 12 ring members, more usually from 5 to 10 ring members. The term "aryl" as used herein refers to a carbocyclyl group having aromatic character and the term "heteroaryl" is used herein to denote a heterocyclyl group having aromatic character. The terms "aryl" and "heteroaryl" embrace polycyclic (e.g. bicyclic) ring systems wherein one or more rings are non-aromatic, provided that at least one ring is aromatic. In such polycyclic systems, the group may be attached by the aromatic ring, or by a non-aromatic ring.

The term "non-aromatic group" embraces unsaturated ring systems without aromatic character, partially saturated and fully saturated carbocyclyl and heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated carbocyclyl groups include cycloalkyl groups as defined below. Partially saturated carbocyclyl groups include cycloalkenyl groups as defined below, for example cyclopentenyl, cyclohexenyl, cycloheptenyl and cyclooctenyl. Saturated heterocyclyl groups include piperidine, morpholine, thiomorpholine. Partially saturated heterocyclyl groups include pyrazolines, for example 2-pyrazoline and 3-pyrazoline.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic aryl and heteroaryl groups containing an aromatic ring and a non-aromatic ring include tetrahydronaphthalene, tetrahydroisoquinoline, tetrahydroquinoline, dihydrobenzthiene, dihydrobenzfuran, 2,3-dihydrobenzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

Examples of carbocyclyl aryl groups include phenyl, naphthyl, indenyl, and tetrahydronaphthyl groups.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The carbocyclyl and heterocyclyl groups can be polycyclic fused ring systems or bridged ring systems such as bicycloalkanes, tricycloalkanes and their oxa- and aza analogues (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

Examples of non-aromatic carbocyclyl groups include cycloalkane groups such as cyclohexyl and cyclopentyl, cycloalkenyl groups such as cyclopentenyl, cyclohexenyl, cycloheptenyl and cyclooctenyl, as well as cyclohexadienyl, cyclooctatetraene, tetrahydronaphthenyl and decalinyl.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

Examples of ring systems encompassed by the definitions of $X_1$-$X_5$ are shown in the following formulae (a)-(t):

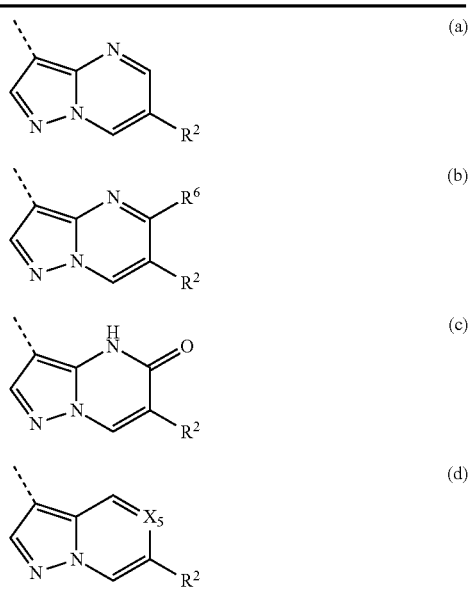

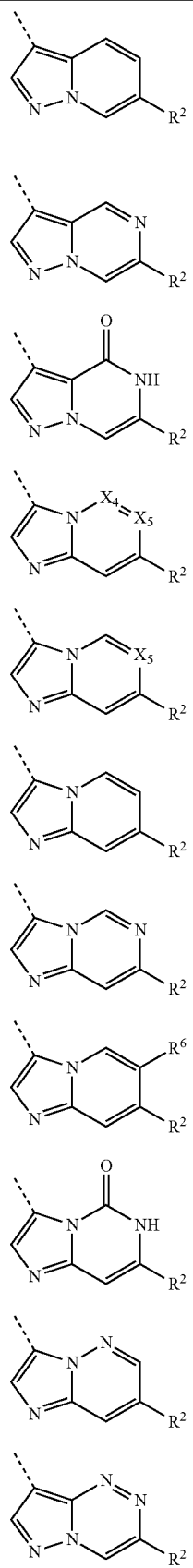

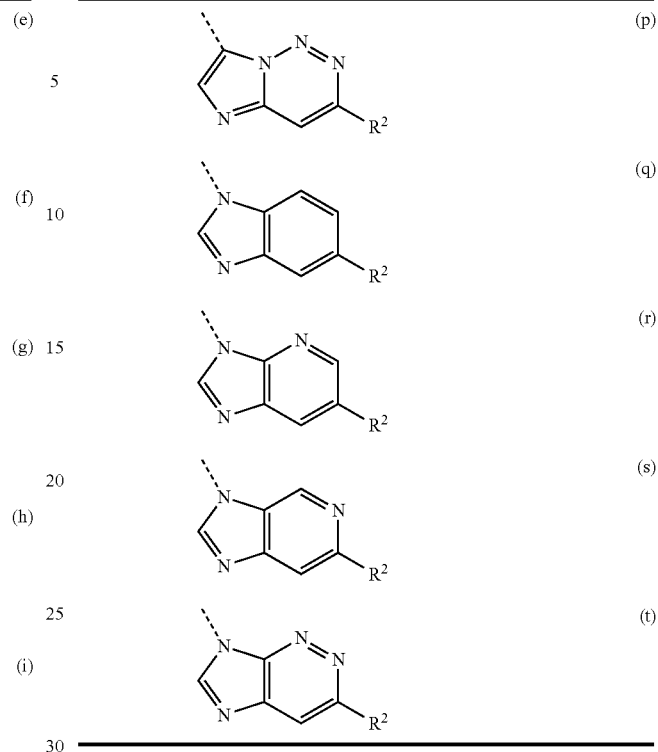

Further examples of ring systems encompassed by the definitions of $X_1$-$X_5$ are shown in the following formulae (u)-(v):

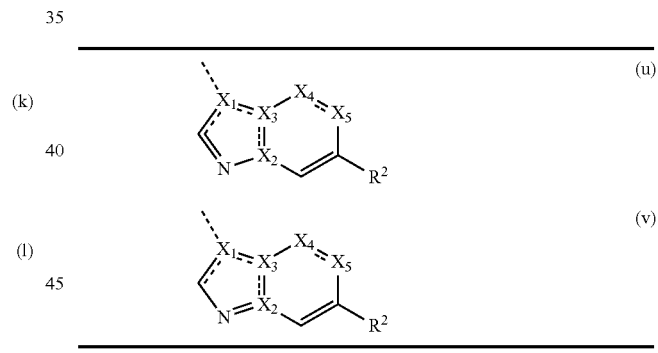

In one embodiment the ring systems encompassed by the definitions of $X_1$-$X_5$ are shown in the above formulae (a)-(p) and (r)-(t).

As mentioned above in one embodiment, ----- represents a single or double bond. It will be clear to the skilled person that when $X_4$ or $X_5$ represents C=O, $X_4$ and $X_5$ are joined by a single bond. In one embodiment $X_4$ and $X_5$ are joined by a double bond.

In one embodiment, two bonds within the 5 membered ring system are double bonds.

In one embodiment, $X_1$ represents C.

In one embodiment, $X_1$ and $X_3$ represent C, $X_5$ represents CH and $X_2$ and $X_4$ represent nitrogen (i.e. a ring system of formula (a)).

In an alternative embodiment, $X_1$ and $X_3$ represent C, $X_4$ and $X_5$ represent CH and $X_2$ represents nitrogen (i.e. a ring system of formula (e)).

In an alternative embodiment, $X_1$ and $X_3$ represent C, $X_4$ represents CH and $X_2$ and $X_5$ represent nitrogen (i.e. a ring system of formula (f)).

In an alternative embodiment, $X_1$ and $X_2$ represent C, $X_3$ represents nitrogen, $X_4$ represents $CR^3$ (e.g. CH) and $X_5$ represents $CR^3$ (e.g. C-Me) (i.e. an example of a ring system of formula (h)).

In an alternative embodiment, $X_1$ and $X_2$ represent C, $X_4$ and $X_5$ represent CH and $X_3$ represents nitrogen (i.e. an example of a ring system of formula (j)).

In an alternative embodiment, $X_1$ and $X_2$ represent C, $X_4$ represents CH and $X_3$ and $X_5$ represent nitrogen (i.e. an example of a ring system of formula (k)).

In an alternative embodiment, $X_2$ and $X_3$ represent C, $X_5$ represents CH and $X_1$ and $X_4$ represent nitrogen (i.e. an example of a ring system of formula (r)).

In one embodiment, $X_1$, $X_3$ and $X_5$ represent C and $X_2$ and $X_4$ represent nitrogen (i.e. an example of a ring system of formula (a)).

In an alternative embodiment, $X_1$, $X_3$, $X_4$ and $X_5$ represent C and $X_2$ represents nitrogen (i.e. an example of a ring system of formula (e)).

In an alternative embodiment, $X_1$, $X_3$ and $X_4$ represent C and $X_2$ and $X_5$ represent nitrogen (i.e. an example of a ring system of formula (f)).

In an alternative embodiment, $X_1$ and $X_2$ represent C, $X_3$ represents nitrogen, $X_4$ represents $CR^3$ (e.g. CH) and $X_5$ represents $CR^6$ (e.g. C-Me) (i.e. an example of a ring system of formula (h)).

In an alternative embodiment, $X_1$, $X_2$, $X_4$ and $X_5$ represent C and $X_3$ represents nitrogen (i.e. an example of a ring system of formula (j)).

In an alternative embodiment, $X_1$, $X_2$ and $X_4$ represent C and $X_3$ and $X_5$ represent nitrogen (i.e. an example of a ring system of formula (k)).

In an alternative embodiment, $X_2$, $X_3$ and $X_5$ represent C and $X_1$ and $X_4$ represent nitrogen (i.e. an example of a ring system of formula (r)).

In one embodiment, $X_2$ represents C.

In one embodiment, $X_3$ represents N.

In one embodiment, $X_4$ represents CH or $CR^3$.

In one embodiment, $X_5$ represents CH or $CR^6$.

In one embodiment, when $X_1$, $X_3$ and $X_5$ represent C and $X_2$ and $X_4$ represent nitrogen, $R^1$ represents a group other than —$NHCOR^4$.

In one embodiment, when $X_1$, $X_2$, $X_4$ and $X_5$ represent C and $X_3$ represents nitrogen, $R^1$ represents a group other than —NH—CO—$(CH_2)_n$—$NR^4R^6$ or —$NHCONR^4R^5$.

In one embodiment, when $X_3$ represents nitrogen and A represents phenyl, $R^1$ represents a group other than —NHCOR$^4$.

In one embodiment, when $X_1$, $X_3$ and $X_5$ represent C and $X_2$ and $X_4$ represent nitrogen, $R^a$ is a group other than =O.

In one embodiment, the compound is of formula (Ia) wherein $X_2$, $X_3$, $X_4$ and $X_5$ represent C and $X_1$ represents nitrogen, $R^1$ represents a group other than —$NHCOR^4$ or —$NHSO_2R^4$.

In one embodiment, when $X_5$ represents $CR^3$ and $R^3$ represents a heterocyclyl group, said heterocyclyl group is other than pyrazole (e.g. optionally substituted pyrazole).

In one embodiment $R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, or halo$C_{1-6}$ alkoxy.

In another embodiment $R^3$ represents amino or —$C_{1-6}$alkylamino.

In one embodiment. $X_1$-$X_5$ represent a ring system of formulae (a), (e), (f), (j), (k) or (r). In a further embodiment, $X_1$-$X_5$ represent a ring system of formulae (a), (e), (f), (j), (k) or (r). In a further embodiment. $X_1$-$X_5$ represent a ring system of formula (a) or (j). In a further embodiment, $X_1$-$X_5$ represent a ring system of formula (j).

Examples of ring systems encompassed by the definition A are shown in the following formulae A1-A15:

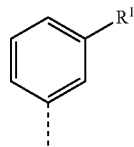 A1

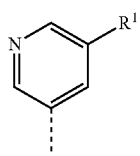 A2

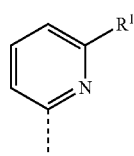 A3

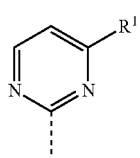 A4

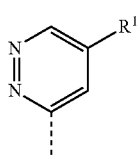 A5

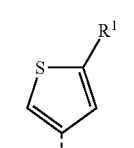 A6

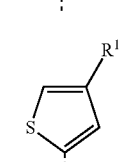 A7

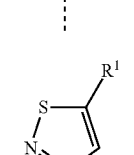 A8

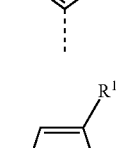 A9

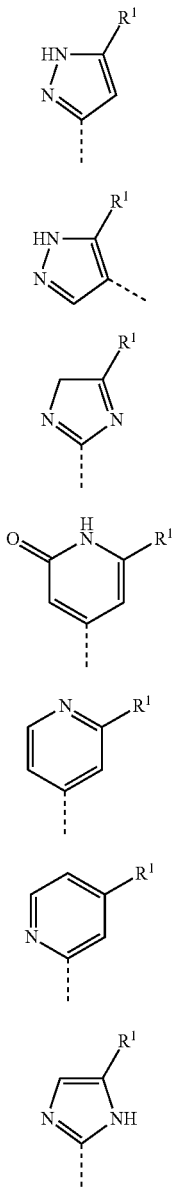

The group A12 can be any tautomer of imidazole e.g. A12a

In one embodiment. A is a group other than pyrazolyl. In one embodiment. A is a group other than imidazolyl.

In one embodiment, A represents a group selected from any one of formulae A1 to A10 and A12-A15. In a further embodiment, A is selected from A2. A14 and A15. In a further embodiment, A is selected from A2.

In one embodiment, A is the group A1 which can be optionally substituted by one or more (e.g. 1, 2 or 3) $R^a$ groups.

It will be appreciated that in the embodiment wherein $X_1$ represents nitrogen, ring A will be attached to said $X_1$ group via a carbon atom.

In one embodiment, A represents a 5- or 6-membered aromatic group.

In one embodiment, A represents a 5-membered aromatic group.

In one embodiment, A represents a non-aromatic group.

In one embodiment, A represents a 6-membered aromatic group.

In one embodiment, A represents pyridin-3-yl or phenyl.

In one embodiment, A represents a group other than pyrazinyl. In one embodiment, A represents a group other than pyrimidinyl. In one embodiment. A represents a group other than pyridinyl or pyrimidinyl. In a further embodiment, A represents unsubstituted phenyl.

In one embodiment, A represents a monocyclic aromatic carbocyclyl or heterocyclyl ring system having for example a 5, 6 or 7 membered ring. In a further embodiment, A represents a 6 membered carbocyclyl ring. In a yet further embodiment, A represents a phenyl group (i.e. a ring system of formula A1\ optionally substituted by one or more (e.g. 1, 2 or 3) $R^a$ groups. In one embodiment, A represents unsubstituted phenyl or phenyl substituted with an —$(CH_2)_s$—$CONR^xR^y$ (e.g. —$CONH_2$), —$(CH_2)_s$—CN (e.g. —CN), $C_{1-6}$ alkyl (e.g. methyl) or —$OR^x$ (e.g. methoxy) group.

In one embodiment, A represents a monocyclic aromatic carbocyclyl or heterocyclyl ring system having for example a 5, 6 or 7 membered ring. In a further embodiment, A represents a 6 membered carbocyclyl ring. In a yet further embodiment, A represents a phenyl group (i.e. a ring system of formula A1) or a pyridyl group (i.e. a ring system of formula A2 or A3) optionally substituted by one or more (e.g. 1, 2 or 3) $R^a$ groups. In one embodiment, A represents unsubstituted phenyl or phenyl substituted with an —$(CH_2)_s$—$CONR^xR^y$ (e.g. —$CONH_2$), —$(CH_2)_s$—CN (e.g. —CN), halogen (e.g. fluorine), $C_{1-6}$ alkyl (e.g. methyl), $C_{1-6}$ alkanol (e.g. —$CH_2OH$) or —$OR^x$ (e.g. methoxy or —$OCH(Me)_2$) group.

In one embodiment, A represents a 6 membered monocyclic aromatic carbocyclyl or heterocyclyl ring system (e.g. phenyl or pyridyl), substituted by $R^1$ at the 3-position or 5-position. When A represents phenyl, in one embodiment $R^1$ is present at the 3-position of the phenyl with respect to the position of attachment to $X_1$.

In one embodiment, A represents a 6 membered monocyclic aromatic carbocyclyl or heterocyclyl ring system (e.g. phenyl or pyridyl), substituted by $R^1$ at the 5-position and further optionally substituted by a single $R^a$ group at the 3-position.

In one embodiment A represents a 6 membered monocyclic aromatic carbocyclyl or heterocyclyl ring system (e.g. phenyl or pyridyl), substituted by $R^1$ at the 5-position and further substituted by a single $R^a$ group at the 3-position.

In one embodiment A represents a 6 membered monocyclic aromatic carbocyclyl ring system (e.g. phenyl), substituted by $R^1$ at the 5-position and further optionally substituted by a single $R^a$ group at the 3-position.

In a further embodiment, A represents a phenyl substituted by $R^1$ at the 5-position and further optionally substituted by a single $R^a$ group at the 3-position.

In one embodiment A represents a 6 membered monocyclic aromatic carbocyclyl ring system (e.g. phenyl), substituted by $R^1$ at the 5-position and further substituted by a single $R^a$ group at the 3-position.

In a further embodiment. A represents a phenyl substituted by $R^1$ at the 5-position and further substituted by a single $R^a$ group at the 3-position.

When $R^a$ is a group substituted on A, $R^a$ in particular represents —$OR^x$. In particular $R^x$ represents $C_{1-6}$alkyl, for example —$CH(CH_3)_2$.

In another embodiment, A represents a phenyl substituted by $R^1$ at the 5-position and further optionally substituted by a single $R^a$ group at the 3-position, wherein $R^a$ represents $C_{2-4}$alkyloxy, halo$C_{2-4}$alkyloxy, $C_{1-4}$alkoxy$C_{1-4}$alkyl, cyclobutoxy, cyclopropoxy, —$N(C_{1-4}alkyl)_2$, —$C_{1-4}$alkyl-$NH(C_{1-4}alkyl)$, —$C_{1-4}$alkyl-$N(C_{1-4}alkyl)_2$, or —$S(=O)_2$—$C_{1-4}$alkyl.

In another embodiment, A represents a phenyl substituted by $R^1$ at the 5-position and further optionally substituted by a single $R^a$ group at the 3-position, wherein $R^a$ represents $C_{2-4}$alkyloxy or $C_{3-4}$ cycloalkyloxy.

In a further embodiment, A represents unsubstituted phenyl.

In one embodiment, $R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$NR$^4$R$^5$, —NHCSNR$^4$R$^5$, —NHCSR$^4$, —NHCSSR$^4$, —NHC(=NR$^4$)NR$^4$R$^5$, —NHC(=NR$^4$)R$^5$, —NH—C(=NH)—NH—CO—R$^4$, —NHCSOR$^4$ or —NHCOSR$^4$.

In one embodiment, $R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, NHSO$_2$NR$^4$R$^5$, —NHCSNR$^4$R$^5$, —NHCSR$^4$, —NHCSSR$^4$, —NHC(=NR$^4$)NR$^4$R$^5$, —NHC(=NR$^4$)R$^5$, —NH—C(=NH)—NH—CO—R$^4$, —NHCSOR$^4$ or —NHCOSR$^4$.

In one embodiment, $R^1$ represents —NHCONR$^4$R$^5$, —NHCOOR$^4$, —NH—CO—(CH$_2$)$_n$—NR$^4$R$^5$, —NH—CO—(CH$_2$)$_n$—COOR$^4$, —NHSO$_2$R$^4$, or —NHCSNR$^4$R$^5$.

In one embodiment, $R^1$ represents —NHCONR$^4$R$^5$, —NHCOOR$^4$, NHSO$_2$NR$^4$R$^5$, —NH—(CH$_2$)$_n$—CONR$^4$R$^5$, —NH—(CH$_2$)$_n$—COOR$^4$, —NH—CH$_2$-aryl, —NH—CO—(CH$_2$)$_n$—NR$^4$R$^5$, —NH—CO—(CH$_2$)$_n$—COOR$^4$, —NHSO$_2$R$^4$, or —NHCSNR$^4$R$^5$.

In one embodiment, $R^1$ represents a NH-heterocyclyl group wherein the heterocyclyl group represents thiadiazole or oxadiazole and the heterocyclyl group may be optionally substituted by one or more (e.g. 1, 2 or 3) $R^a$ groups.

In one embodiment, $R^1$ represents a NH-thiadiazolyl or NH-oxadiazolyl wherein the heterocyclyl group may be optionally substituted by one $R^a$ group.

In one embodiment $R^1$ is NH-[1,3,4]thiadiazol-2-yl. In another embodiment $R^1$ is NH-[1,3,4]oxadiazol-2-yl.

In one embodiment, $R^1$ represents —NHCONR$^4$R$^5$. In a further embodiment, $R^4$ represents hydrogen or $C_{1-6}$ alkyl (e.g. methyl) and $R^5$ represents hydrogen, $C_{1-6}$ alkyl (e.g. methyl, ethyl or butyl), —(CH$_2$)$_n$—NR$^x$R$^y$ (e.g. —(CH$_2$)$_2$NH$_2$ or —(CH$_2$)$_3$NH$_2$), —(CH$_2$)$_n$-aryl (e.g. benzyl optionally substituted by a halogen atom, such as a fluorine atom), or halo$C_{1-6}$ alkyl (e.g. —CH$_2$—CF$_3$).

In one embodiment, $R^1$ represents —NHCONR$^4$R$^5$. In a further embodiment, $R^4$ represents $C_{1-6}$ alkyl (e.g. methyl) or halo$C_{1-6}$ alkyl. In a further embodiment, $R^4$ represents $C_{1-6}$ alkyl (e.g. methyl) or halo$C_{1-6}$ alkyl (e.g. —(CH$_2$)$_2$—F, —CH$_2$—CH—F$_2$, —CH(Me)-CF$_3$ or —CH$_2$—CF$_3$). In a yet further embodiment, $R^4$ represents halo$C_{1-6}$ alkyl (e.g. —CH$_2$—CF$_3$).

In one embodiment, $R^1$ represents —NHCONR$^4$R$^5$. In a further embodiment, $R^4$ represents hydrogen or $C_{1-6}$ alkyl (e.g. methyl) and $R^5$ represents hydrogen, $C_{1-6}$ alkyl (e.g. methyl, ethyl, butyl, —CH(Me)$_2$, —CH$_2$CH(Me)$_2$ or —C(Me)$_3$), $C_{1-6}$ alkyl substituted by one or more $R^a$ groups (e.g. —CH$_2$—C(Me)$_2$—CH$_2$—NH$_2$, —CH$_2$—CH(Me)-OMe or —CH$_2$—C(F)$_2$—CH$_2$NH$_2$), $C_{1-6}$ alkanol (e.g. —CH$_2$—CH(OH)—CH$_2$OH), —(CH$_2$)$_n$—NR$^x$R$^y$ (e.g. —(CH$_2$)$_2$NHCOOt-Bu, —(CH$_2$)$_2$NH$_2$ or —(CH$_2$)$_3$NH$_2$), —(CH$_2$)$_n$-aryl (e.g. benzyl optionally substituted by a halogen atom, such as a fluorine atom), —(CH$_2$)$_n$-heterocyclyl (e.g. —CH$_2$-dioxaolanyl (optionally substituted by one or more $C_{1-6}$ alkyl (e.g. methyl) groups), —CH$_2$-tetrahydrofuranyl or —CH$_2$-piperidinyl) or halo$C_{1-6}$ alkyl (e.g. —(CH$_2$)$_2$—F, —CH$_2$—CH—F$_2$, —CH(Me)-CF$_3$ or —CH$_2$—CF$_3$).

In one embodiment, when A represents phenyl and $R^1$ represents —NHCONR$^4$R$^5$, $R^4$ and $R^5$ represent a group other than phenyl.

In another embodiment. A represents phenyl. $R^1$ represents —NHCONR$^4$R$^5$. $R^4$ represents halo$C_{1-6}$ alkyl and $R^5$ represents hydrogen.

In one embodiment. $R^1$ represents —NHCOOR$^4$. In a further embodiment, $R^4$ represents $C_{1-6}$ alkyl (e.g. methyl) or halo$C_{1-6}$ alkyl. In a further embodiment, $R^4$ represents $C_{1-6}$ alkyl (e.g. methyl) or halo$C_{1-6}$ alkyl (e.g. —CH$_2$—CF$_3$). In a yet further embodiment, $R^4$ represents $C_{1-6}$ alkyl (e.g. methyl).

In one embodiment, $R^1$ represents —NH—CO—(CH$_2$)$_n$—NR$^4$R$^5$. In a further embodiment, n represents 1 and $R^4$ and $R^5$ both represent hydrogen.

In one embodiment, $R^1$ represents —NH—CO—(CH$_2$)$_n$—COOR$^4$. In a further embodiment, n represents 2 and $R^4$ represents hydrogen.

In one embodiment, $R^1$ represents —NHSO$_2$R$^4$. In a further embodiment, $R^4$ represents $C_{1-6}$ alkyl (e.g. methyl) or —(CH$_2$)$_n$—NR$^x$R$^y$ (e.g. where NR$^x$R$^y$ represents NH$_2$ or NMe$_2$).

In one embodiment, $R^1$ represents —NHCSNR$^4$R$^5$. In a further embodiment, one of $R^4$ and $R^5$ represents hydrogen and the other represents $C_{1-6}$ alkyl (e.g. ethyl).

In one embodiment, $R^1$ represents —NHCOR$^4$. In a further embodiment, $R^4$ represents $C_{1-6}$ alkyl (e.g. methyl, ethyl or propyl) or $C_{1-6}$ alkanol (e.g. —CH$_2$OH).

In a further embodiment, $R^1$ represents —NHCONR$^4$R$^5$ (e.g. —NHCONHEt or —NHCONHCH$_2$CF$_3$) or —NHCSNR$^4$R$^5$ (e.g. —NHCSNHEt). In a yet further embodiment, $R^1$ represents —NHCONR$^4$R$^5$ (e.g. —NH-CONHEt or —NHCONHCH$_2$CF$_3$). In a yet further embodiment, $R^1$ represents —NHCONHCH$_2$CF$_3$.

In a one embodiment, $R^1$ represents NHSO$_2$NR$^4$R$^5$. In a further embodiment, $R^4$ represents hydrogen and $R^5$ represents halo$C_{1-6}$ alkyl (e.g. —CH$_2$—CF$_3$).

In one embodiment, $R^1$ represents —NH—(CH$_2$)$_n$—CONR$^4$R$^5$. In a further embodiment, n represents 1, $R^4$ represents hydrogen and $R^5$ represents hydrogen or $C_{1-6}$ alkyl (e.g. methyl).

In one embodiment, $R^1$ represents —NH—(CH$_2$)$_n$—COOR$^4$. In a further embodiment, n represents 1 and $R^4$ represents hydrogen.

When $R^6$ represents a heterocyclyl group, in one embodiment the heterocyclyl group is other than pyrazolyl (e.g. optionally substituted pyrazolyl).

In one embodiment, $R^6$ represents hydrogen.

In one embodiment, $R^6$ represents $C_{1-6}$ alkoxy (e.g. unsubstituted $C_{1-6}$ alkoxy).

In one embodiment, $X_5$ represents CH, nitrogen or C=O.

In one embodiment, one of $R^v$ and $R^w$ represents hydrogen. In a further embodiment $R^v$ represents hydrogen.

In one embodiment $R^v$ represents hydrogen and $R^w$ represents -Q-R$^a$.

In a further embodiment Q represents a direct bond and $R^a$ represents —(CH$_2$)$_n$—O—R$^x$.

In a still further embodiment $R^x$ represents hydrogen, —(CH$_2$)$_n$—O—$C_{1-6}$alkyl or —(CH$_2$)$_n$—OH.

In one embodiment Q represents a direct bond and $R^a$ represents —(CH$_2$)$_s$—NR$^x$R$^y$. In a further embodiment one of $R^x$ and $R^y$ represents hydrogen or $C_{1-6}$alkyl and the other represents —(CH$_2$)$_n$—O—$C_{1-6}$alkyl. In a still further embodiment one of $R^x$ and $R^y$ represents —(CH$_2$)$_n$—O—$C_{1-6}$alkyl and the other represents —(CH$_2$)$_s$—$C_{3-8}$cycloalkenyl. In a still further embodiment one of $R^x$ and $R^y$ represents $C_{1-6}$alkyl and the other represents $C_{1-6}$alkyl or —$(CH_2)_n$—OH.

In one embodiment Q represents a direct bond and $R^a$ represents —$(CH_2)_s$—$NR^x$—$(CF_{12})_s$—$SO_2R^y$. In a further embodiment $R^x$ and $R^y$ independently represent hydrogen or $C_{1-6}$alkyl. In a still further embodiment $R^x$ represents hydrogen or $C_{1-6}$alkyl and $R^y$ represents $C_{1-6}$alkyl.

In one embodiment $R^v$ represents hydrogen and $R^w$ represents a —Z-heterocyclyl group wherein said heterocyclyl group may be optionally substituted by one or more (e.g. 1, 2 or 3) $R^a$ groups.

In a further embodiment Z represents a direct bond. In a still further embodiment said heterocyclyl group is substituted by one or more $C_{1-6}$alkyl groups.

In a still further embodiment Z represents —$(CR^xR^y)_n$— and in a still further embodiment $R^x$ and $R^y$ both represent hydrogen. In a still further embodiment said heterocyclyl group is substituted by one or more $C_{1-6}$alkyl, —O—$R^x$, —$(CH_2)_n$—O—W, —$(CH_2)_s$—$SO_2$—$NR^xR^y$, —$(CH_2)_s$N-$R^xR^y$ or —NH—C(=NH)—$NH_2$ group. In a yet further embodiment $R^x$ and $R^y$ independently represent hydrogen or $C_{1-6}$alkyl.

In a yet further embodiment Z represents —$(CR^xR^y)_s$—$NR^x$— and in a still further embodiment $R^x$ and $R^y$ both represent hydrogen. In a still further embodiment said heterocyclyl group is substituted by one or more $C_{1-6}$alkyl group.

In a yet further embodiment Z represents —$(CR^xR^y)_s$—CO— and in a still further embodiment W and $R^y$ both represent hydrogen. In a still further embodiment said heterocyclyl group is substituted by one or more $C_{1-6}$alkyl group.

In one embodiment Z is —$(CR^xR^y)_s$—$NR^x$. In another embodiment Z is —$(CR^xR^y)_n$—. In one embodiment $R^x$ and $R^y$ are independently selected from hydrogen and hydroxyl. In a further embodiment Z is —$CH_2$—CHOH—$CH_2$—NH— or —$CH_2$—CHOH—$CH_2$—.

In one embodiment s is an integer from 1-4. In another embodiment s is an integer from 2-3. In further embodiment s is zero. In a still further embodiment s is 3.

In one embodiment $R^w$ is —$(CR^xR^y)_s$—$NR^x$-carbocyclyl, wherein the carbocyclyl group is a $C_{3-6}$ cycloalkyl group.

In one embodiment $R^w$ is —$(CR^xR^y)_n$-heterocyclyl, wherein the heterocyclyl group is a nitrogen containing heterocyclyl group.

In one embodiment, one of $R^v$ and $R^w$ represents -Q-$R^a$. In one embodiment $R^v$ represents -Q-$R^a$. In one embodiment, $R^w$ represents -Q-$R^a$.

In one embodiment $R^v$ represents -Q-$R^a$ and $R^w$ represents hydrogen. In a further embodiment Q represents a direct bond and $R^a$ represents $C_{1-6}$alkyl (e.g. methyl, ethyl).

In one embodiment $R^v$ and $R^w$ independently represent -Q-$R^a$ wherein Q represents a direct bond and $R^a$ represents $C_{1-6}$alkyl, —$(CH_2)_n$—O—$R^x$ or —$(CH_2)_n$—O—$C_{1-6}$alkyl. In a still further embodiment $R^v$ represents $C_{1-6}$alkyl (e.g. methyl or ethyl). In a still further embodiment $R^x$ represents hydrogen or $C_{1-6}$alkyl.

In one embodiment, one of $R^v$ and $R^w$ represents a —Y-carbocyclyl or —Z-heterocyclyl group. In one embodiment $R^w$ represents a —Y-carbocyclyl or —Z-heterocyclyl group.

In one embodiment $R^v$ represents -Q-$R^a$ wherein Q represents a direct bond and $R^a$ represents $C_{1-6}$alkyl (e.g. methyl) and $R^w$ represents a —Z-heterocyclyl group wherein said heterocyclyl groups may be optionally substituted by one or more (e.g. 1, 2 or 3) $R^a$ groups.

In a further embodiment Z represents —$(CR^xR^y)_n$— and in a still further embodiment $R^x$ and $R^y$ both represent hydrogen.

In one embodiment $R^v$ represents a —Y-carbocyclyl or —Z-heterocyclyl group.

In one embodiment $R^v$ represents a —Y-carbocyclyl group and $R^w$ represents hydrogen. In a further embodiment Y is a direct bond. In yet a further embodiment Y represents —$(CR^xR^y)_n$—. In a still further embodiment $R^x$ and $R^y$ represent hydrogen.

In one embodiment $R^v$ represents $C_{1-6}$ alkyl group or a —Y—$C_{3-6}$ cycloalkyl group and $R^w$ represents hydrogen. In a still further embodiment Y is a direct bond. In yet a further embodiment $R^v$ represents methyl group or a cyclopropyl group and $R^w$ represents hydrogen.

In one embodiment $R^v$ represents a —Y-carbocyclyl group and $R^w$ represents a -Q-$R^a$ group. In a further embodiment Q represents a direct bond and $R^a$ represents $C_{1-6}$alkyl or —$(CH_2)_n$—O—$R^x$. In a still further embodiment Y is a direct bond. In yet a further embodiment Y represents —$(CR^xR^y)_n$—. In a still further embodiment $R^x$ and $R^y$ represent hydrogen.

In one embodiment $R^v$ represents a —Y-carbocyclyl group and $R^w$ represents a -Q-$R^a$ group. In a still further embodiment Y is a direct bond. In yet a further embodiment $R^v$ represents a cyclopropyl group. In a further embodiment Q represents a direct bond and $R^a$ represents —$(CH_2)_n$—O—$R^x$. In a still further embodiment n represents 2 and $R^x$ represents hydrogen.

In one embodiment when $R^v$ and/or $R^w$ represent $R^b$ and $R^b$ represents a —Y-carbocyclyl or —Z-heterocyclyl group wherein said carbocyclyl and heterocyclyl group is substituted by one or more (e.g. 1, 2 or 3) $R^a$ groups $R^a$ represents halogen, $C_{1-6}$ alkyl, $C_{2-6}$ alkenyl, $C_{2-6}$ alkynyl, $C_{3-8}$ cycloalkyl, $C_{3-8}$ cycloalkenyl, —$OR^x$, —$(CH_2)_n$—O—$R^x$, —O—$(CH_2)_n$—$OR^x$, halo$C_{1-6}$ alkyl, halo$C_{1-6}$ alkoxy, $C_{1-6}$ alkanol, =O, =S, nitro, —Si$(R^x)_4$, —$(CH_2)_s$—CN, —S—$R^x$, SO—$R^x$, —$SO_2$—$R^x$, aryl, heterocyclyl group, —$(CR^xR^y)_s$—$CONR^xR^y$, —$(CH_2)_s$—$NR^xR^y$, —$(CH_2)_s$—$NR^xCOR^y$, —$(CH_2)_s$—$NR^x$—$(CH_2)_s$—$SO_2$—$R^y$, —$NR^x$—$(CH_2)_s$—$R^z$, —$(CH_2)_s$—O—C(=O)—$C_{1-4}$alkyl-$NR^xR^y$, —$(CH_2)_s$—$NR^x$—$(CH_2)_n$—O—C(=O)—$R^z$, —$(CR^xR^y)$—O—C(=O)—$R^z$, —$(CH_2)_s$—NH—$SO_2$—$NR^xR^y$, —$OCONR^xR^y$, —$(CH_2)_s$—$NR^xCO_2R^y$, —O—$(CH_2)_s$—$CR^xR^y$—$(CH_2)_t$—$OR^z$, —$(CH_2)_s$—$SO_2NR^xR^y$ or —NH—C(=NH)—$NH_2$; wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more $R^x$ groups.

In one embodiment, $R^b$ independently represents a -Q-$R^a$ group or a —Y-carbocyclyl or —Z-heterocyclyl group wherein said carbocyclyl and heterocyclyl groups may be optionally substituted by one $R^a$ group.

In one embodiment, Y represents a direct bond or —O—$(CH_2)_s$— (e.g. —O—$CH_2$—).

In one embodiment, Y and Z independently represent a direct bond, —CO—$(CH_2)_s$—, —COO—, —$(CH_2)_n$—, —$NR^x(CH_2)_n$—, —$(CH_2)_n$—$NR^x$, —$CONR^x$, —$NR^xCO$—, —$SO_2NR^x$, —$NR^xSO_2$—, —$NR^xCONR^y$—, —$NR^xCS$-$NR^y$—, —O—$(CH_2)_s$—, —$(CH_2)_s$—O—, S—, —SO— or —$(CH_2)_s$—$SO_2$—.

In one embodiment, Y and Z independently represent a direct bond or —CO—, —O—$(CH_2)_s$— or —$(CH_2)_n$—NH—.

In one embodiment, Y and Z independently represent a direct bond or —CO—, —O—$(CH_2)_s$— or —$(CH_2)_s$—NH—.

In one embodiment, Y represents a direct bond.

In one embodiment, Z represents a direct bond.

In one embodiment, Z represents a direct bond, —CO—, —(CH$_2$)$_n$— (e.g. —CH$_2$—, —(CH$_2$)$_2$— or —(CH$_2$)$_3$—) or —O—. In a further embodiment, Z represents —(CH$_2$)$_n$— (e.g. —CH$_2$—).

In one embodiment, Z represents a direct bond, CO, —(CH$_2$)$_n$— (e.g. —CH$_2$—, —(CH$_2$)$_2$— or —(CH$_2$)$_3$—), —(CH$_2$)$_n$—NH— or —O—. In a further embodiment, Z represents —(CH$_2$)$_n$— (e.g. —CH$_2$—).

In one embodiment, Z represents a direct bond, —CO—, —(CH$_2$)$_n$— (e.g. —CH$_2$—, —(CH$_2$)$_2$— or —(CH$_2$)$_3$—), —(CH$_2$)$_s$—NH— (e.g. —NH—) or —O—. In a further embodiment, Z represents —(CH$_2$)$_n$— (e.g. —CH$_2$—).

In one embodiment, Z represents a direct bond, —CO—, —(CH$_2$)$_n$— (e.g. —CH$_2$—, —(CH$_2$)$_2$— or —(CH$_2$)$_n$— (e.g. —CH$_2$—).

In one embodiment the compound of formula (I) is a compound of formula (Ib) or (Ic):

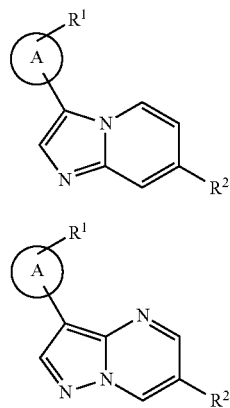

wherein
A represents an aromatic carbocyclyl or heterocyclyl group which may be optionally substituted by one or more (e.g. 1, 2 or 3) R$^a$ groups;
R$^1$ represents —NHCONR$^4$R$^5$, —NHCOOR$^4$, —NH—CO—(CH$_2$)$_n$—NR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$NR$^4$R$^5$, —NHCOR$^4$;
R$^4$ and R$^5$ independently represent hydrogen, C$_{1-6}$ alkyl, C$_{2-6}$ alkenyl, C$_{2-6}$ alkynyl, C$_{3-8}$ cycloalkyl, C$_{3-8}$ cycloalkenyl, C$_{1-6}$ alkanol, haloC$_{1-6}$ alkyl, —(CH$_2$)$_n$—NR$^x$R$^y$, —(CH$_2$)$_s$—CO-OR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said C$_{1-6}$ alkyl, C$_{2-6}$ alkenyl, C$_{2-6}$ alkynyl, C$_{3-8}$ cycloalkyl, C$_{3-8}$ cycloalkenyl, aryl and heterocyclyl groups may be optionally substituted by one or more (e.g. 1, 2 or 3) R$^a$ groups;
R$^x$, R$^y$ and R$^z$ independently represent hydrogen, C$_{1-6}$ alkyl, C$_{2-6}$ alkenyl, C$_{2-6}$ alkynyl, C$_{1-6}$ alkanol, hydroxy, C$_{1-6}$ alkoxy, haloC$_{1-6}$ alkyl, —CO—(CH$_2$)$_n$—C$_{1-6}$ alkoxy, C$_{3-8}$ cycloalkyl or C$_{3-8}$ cycloalkenyl;
R$^2$ represents a —CR$^v$=N—OR$^w$ group;
R$^w$ and R$^w$ independently represent hydrogen or R$^b$;
R$^a$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —O—(CH$_2$), —OR$^x$, haloC$_{1-6}$ alkyl, haloC$_{1-6}$ alkoxy, C$_{1-6}$ alkanol, =O, =S, nitro, —(CH$_2$)$_s$—CN, —S—R$^x$, —SO—R$^x$, —SO$_2$—R$^x$, —COR$^x$, —(CR$^x$R$^y$)$_s$—COOR$^z$, —(CH$_2$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$SO$_2$—R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$ or —(CH$_2$), —SO$_2$NR$^x$R$^y$ groups;
R$^b$ represents a -Q-R$^a$ group or a —Y— carbocyclyl or —Z-heterocyclyl group wherein said aryl and heterocyclyl groups may be optionally substituted by one or more (e.g. 1, 2 or 3) R$^a$ groups;
Y and Z independently represent a direct bond, —CO—(CH$_2$)$_s$—, —COO—, —(CH$_2$)$_n$—, —NR$^x$—(CH$_2$)$_n$—, —(CH$_2$)$_n$—NR$^x$—, —CONR$^x$—, —NR$^x$CO—, —SO$_2$NR$^x$—, —NR$^x$SO$_2$—, —NR$^x$CONR$^y$—, —NR$^x$CS-NR$^y$—, —O—(CH$_2$)$_s$—, —(CH$_2$)$_s$—O—, S—, —SO— or —(CH$_2$)$_s$—SO$_2$—;
Q represents NR$^x$, S(O)$_q$ or a direct bond;
m and n independently represent an integer from 1-4;
s and t independently represent an integer from 0-4;
q represent an integer from 0-2;
wherein when R$^v$ represents hydrogen R$^w$ cannot represent hydrogen or —CH$_3$;
or a pharmaceutically acceptable salt, solvate or derivative thereof.

In one embodiment of compounds of formula (Ib) and (Ic), Y and Z independently represent a direct bond, —CO—(CH$_2$)$_s$—, —COO—, —(CH$_2$)$_n$—, —NR$^x$—(CH$_2$)$_s$—, —(CH$_2$)$_s$—NR$^x$—, —CONR$^x$—, —NR$^x$CO—, —SO$_2$NR$^x$—, —NR$^x$SO$_2$—, —NR$^x$CONR$^y$—, —NR$^x$CS-NR$^y$—, —O—(CH$_2$)$_s$—, —(CH$_2$)$_s$—O—, S—, —SO— or —(CH$_2$)$_s$—SO$_2$—;

In a further embodiment the compound of formula (I) is a compound of formula (Id):

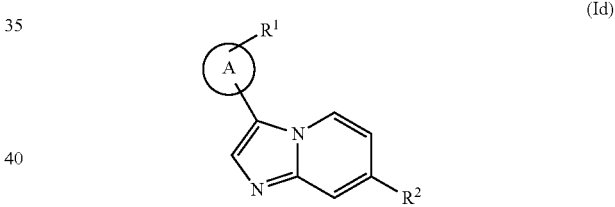

wherein
A represents a phenyl group which may be optionally substituted by one R$^a$ group wherein R$^a$ is —OR$^x$; R$^1$ represents —NHCONR$^4$R$^5$;
R$^4$ represents hydrogen;
R$^5$ represents haloC$_{1-6}$ alkyl;
R$^x$, R$^y$ and R$^z$ independently represent hydrogen, C$_{1-6}$ alkyl, C$_{2-6}$ alkenyl, C$_{2-6}$ alkynyl, C$_{1-6}$ alkanol, hydroxy, C$_{1-6}$ alkoxy, haloC$_{1-6}$ alkyl, —CO—(CH$_2$)$_n$—C$_{1-6}$alkoxy, C$_{3-8}$ cycloalkyl or C$_{3-8}$ cycloalkenyl;
R$^2$ represents a —CR$^v$=N—OR$^w$ group;
R$^v$ represents hydrogen, C$_{1-6}$ alkyl, C$_{3-8}$ cycloalkyl or —Y-carbocyclyl;
R$^w$ is selected from:
  hydrogen;
  -Q-R$^a$ wherein Q represents a direct bond and R$^a$ represents C$_{1-6}$ alkyl or —(CH$_2$)$_n$—O—R$^x$, wherein R$^x$ represents hydrogen, —(CH$_2$)$_n$—O—C$_{1-6}$ alkyl or —(CH$_2$)$_n$—OH, or R$^a$ represents —(CH$_2$)$_s$—NR$^x$R$^y$ wherein one of R$^x$ and R$^y$ represents hydrogen or C$_{1-6}$ alkyl and the other represents —(CH$_2$)$_n$—O—C$_{1-6}$ alkyl or —(CH$_2$)$_s$—C$_{3-s}$cycloalkenyl, C$_{1-6}$ alkyl or —(CH$_2$)$_n$—OH, or R$^a$ represents —(CH$_2$)$_s$—NR$^x$—(CH$_2$)$_s$—SO$_2$R$^y$ wherein R$^x$ and R$^y$ independently represent hydrogen or C$_{1-6}$alkyl;

Y—$C_{3-6}$ cycloalkyl group wherein Y is a direct bond or —$(CR^xR^y)_n$— wherein $R^x$ and $R^y$ represent hydrogen; and Z-heterocyclyl group wherein said heterocyclyl group may be optionally substituted by one or more (e.g. 1, 2 or 3) $R^a$ groups e.g. $C_{1-6}$alkyl, —O—$R^x$, —$(CH_2)_n$—O—$R^x$, —$(CH_2)_s$—$SO_2$—$NR^xR^y$, —$(CH_2)_sNR^xR^y$ or —N—$CNHNH_2$ groups, wherein Z independently represent a direct bond, —$(CR^xR^y)_s$—CO—, —$(CR^xR^y)_s$—$NR^x$ or —$(CR^xR^y)_n$— wherein $R^x$ and $R^y$ independently represent hydrogen, hydroxyl or $C_{1-6}$alkyl.

m and n independently represent an integer from 1-3;
s and t independently represent an integer from 0-3;
wherein when $R^v$ represents hydrogen $R^w$ cannot represent hydrogen or —$CH_3$;
or a pharmaceutically acceptable salt or solvate thereof.

In one embodiment $R^a$ represents —$OR^x$ wherein $R^x$ represents $C_{2-4}$alkyl or $C_{3-4}$ cycloalkyl, for example —$CH(CH_3)_2$.

In one embodiment $R^v$ represents hydrogen, methyl, ethyl, cyclopropyl, cyclobutyl, or —$CH_2$—$C_{3-8}$ cycloalkyl e.g. —$CH_2$-cyclopropyl.

In one embodiment, the compound of formula (I) is a compound selected from Examples 1-1 to 1-63. In a further embodiment, the compound of formula (I) is a compound selected from 1-21 and 1-50, or a pharmaceutically acceptable salt or solvate thereof.

In one embodiment, the compound of formula (I) is a compound selected from Examples 1-1 to 1-67. In a further embodiment, the compound of formula (I) is a compound selected from 1-21 and 1-50, or a pharmaceutically acceptable salt or solvate thereof.

In one embodiment, the compound of formula (I) is a compound selected from:

1-(3-{7-[(3-Morpholin-4-yl-propoxyimino)-methyl]-imidazo[1,2-a]pyridin-3-yl}-phenyl)-3-(2,2,2-trifluoro-ethyl)-urea;

1-[3-(7-{[2-(2-Methoxy-ethoxy)-ethoxyimino]-methyl}-imidazo[1,2-a]pyridin-3-yl)-phenyl]-3-(2,2,2-trifluoro-ethyl)-urea;

1-(3-{7-[(2-Methoxy-ethoxyimino)-methyl]-imidazo[1,2-a]pyridin-3-yl}-phenyl)-3-(2,2,2-trifluoro-ethyl)-urea;

1-(3-{7-[(2-Hydroxy-ethoxyimino)-methyl]-imidazo[1,2-a]pyridin-3-yl}-phenyl)-3-(2,2,2-trifluoro-ethyl)-urea;

1-(3-{7-[(3-Cyclopropylamino-2-hydroxy-propoxyimino)-methyl]-imidazo[1,2-a]pyridin-3-yl}-phenyl)-3-(2,2,2-trifluoro-ethyl)-urea;

1-[3-(7-{[2-Hydroxy-3-(4-hydroxy-piperidin-1-yl)-propoxyimino]-methyl}-imidazo[1,2-a]pyridin-3-yl)-phenyl]-3-(2,2,2-trifluoro-ethyl)-urea;

1-{3-[7-({2-[(2-Methoxy-ethyl)-methyl-amino]-ethoxyimino}-methyl)-imidazo[1,2-a]pyridin-3-yl]-phenyl}-3-(2,2,2-trifluoro-ethyl)-urea;

1-(3-{7-[(Pyridin-4-ylmethoxyimino)-methyl]-imidazo[1,2-a]pyridin-3-yl}-phenyl)-3-(2,2,2-trifluoro-ethyl)-urea;

1-[3-(7-{[2-(2-Hydroxy-ethoxy)-ethoxyimino]-methyl}-imidazo[1,2-a]pyridin-3-yl)-phenyl]-3-(2,2,2-trifluoro-ethyl)-urea;

1-{3-[7-({2-[Benzyl-(2-methoxy-ethyl)-amino]-ethoxyimino}-methyl)-imidazo[1,2-a]pyridin-3-yl]-phenyl}-3-(2,2,2-trifluoro-ethyl)-urea;

1-(3-{7-[(Pyrimidin-2-yloxyimino)-methyl]-imidazo[1,2-a]pyridin-3-yl}-phenyl)-3-(2,2,2-trifluoro-ethyl)-urea;

1-[3-(7-{[3-(4-Methyl-piperazin-1-yl)-propoxyimino]-methyl}-imidazo[1,2-a]pyridin-3-yl)-phenyl]-3-(2,2,2-trifluoro-ethyl)-urea;

1-(3-{7-[(3-Methyl-3H-imidazol-4-ylmethoxyimino)-methyl]-imidazo[1,2-a]pyridin-3-yl}-phenyl)-3-(2,2,2-trifluoro-ethyl)-urea;

1-(3-{7-[(Pyridin-2-ylmethoxyimino)-methyl]-imidazo[1,2-a]pyridin-3-yl}-phenyl)-3-(2,2,2-trifluoro-ethyl)-urea;

1-(3-{7-[(5-Chloro-thiophen-2-ylmethoxyimino)-methyl]-imidazo[1,2-a]pyridin-3-yl}-phenyl)-3-(2,2,2-trifluoro-ethyl)-urea;

1-(3-{7-[(2-Methyl-thiazol-4-ylmethoxyimino)-methyl]-imidazo[1,2-a]pyridin-3-yl}-phenyl)-3-(2,2,2-trifluoro-ethyl)-urea;

1-[3-(7-{[3-(1-Methyl-piperidin-4-ylamino)-propoxyimino]-methyl}-imidazo[1,2-a]pyridin-3-yl)-phenyl]-3-(2,2,2-trifluoro-ethyl)-urea;

1-(3-{7-[(3-Pyrrolidin-1-yl-propoxyimino)-methyl]-imidazo[1,2-a]pyridin-3-yl}-phenyl)-3-(2,2,2-trifluoro-ethyl)-urea;

1-[3-(7-{[3-(4-Methoxy-piperidin-1-yl)-propoxyimino]-methyl}-imidazo[1,2-a]pyridin-3-yl)-phenyl]-3-(2,2,2-trifluoro-ethyl)-urea;

1-[3-(7-{[3-(Tetrahydro-pyran-4-ylamino)-propoxyimino]-methyl}-imidazo[1,2-a]pyridin-3-yl)-phenyl]-3-(2,2,2-trifluoro-ethyl)-urea;

1-{3-[7-({2-[1-(2-Methoxy-ethyl)-piperidin-4-yl]-ethoxyimino}-methyl)-imidazo[1,2-a]pyridin-3-yl]-phenyl}-3-(2,2,2-trifluoro-ethyl)-urea;

1-{3-[7-({2-[1-(2-Hydroxy-ethyl)-piperidin-4-yl]-ethoxyimino}-methyl)-imidazo[1,2-a]pyridin-3-yl]-phenyl}-3-(2,2,2-trifluoro-ethyl)-urea;

1-[3-(7-{1-Hydroxyimino-ethyl}-imidazo[1,2-a]pyridin-3-yl)-phenyl]-3-(2,2,2-trifluoro-ethyl)-urea;

1-[3-(7-{1-Methoxyimino-ethyl}-imidazo[1,2-a]pyridin-3-yl])-phenyl]-3-(2,2,2-trifluoro-ethyl)-urea;

1-[3-(7-{1-2-Hydroxy-ethoxyimino-ethyl}-imidazo[1,2-a]pyridin-3-yl)-phenyl]-3-(2,2,2-trifluoro-ethyl)-urea;

1-[3-(7-{1-3-Morpholin-4-yl-propoxyimino-ethyl}-imidazo[1,2-a]pyridin-3-yl)-phenyl]-3-(2,2,2-trifluoro-ethyl)-urea;

1-(3-{7-[(2-Piperidin-4-yl-ethoxyimino)-methyl]-imidazo[1,2-a]pyridin-3-yl}-phenyl)-3-(2,2,2-trifluoro-ethyl)-urea;

1-(3-{7-[(2-Dimethylamino-ethoxyimino)-methyl]-imidazo[1,2-a]pyridin-3-yl}-phenyl)-3-(2,2,2-trifluoro-ethyl)-urea;

1-{3-[7-({2-[(2-Methanesulfonyl-ethyl)-methyl-amino]-ethoxyimino}-methyl)-imidazo[1,2-a]pyridin-3-yl]-phenyl}-3-(2,2,2-trifluoro-ethyl)-urea;

1-{3-[7-({2-[(2-Hydroxy-ethyl)-methyl-amino]-ethoxyimino}-methyl)-imidazo[1,2-a]pyridin-3-yl]-phenyl}-3-(2,2,2-trifluoro-ethyl)-urea;

1-{3-[7-({3-[4-(2-Hydroxy-ethyl)-piperazin-1-yl]-propoxyimino}-methyl)-imidazo[1,2-a]pyridin-3-yl]-phenyl}-3-(2,2,2-trifluoro-ethyl)-urea;

1-[3-(7-{[3-(3-Hydroxy-pyrrolidin-1-yl)-propoxyimino]-methyl}-imidazo[1,2-a]pyridin-3-yl)-phenyl]-3-(2,2,2-trifluoro-ethyl)-urea;

4-{3-[1-(3-{3-[3-(2,2,2-Trifluoro-ethyl)-ureido]-phenyl}-imidazo[1,2-a]pyridin-7-yl)-meth-(E)-ylideneaminooxy]-propyl}-piperazine-1-sulfonic acid dimethylamide;

1-{3-[7-(Cyclopropylmethoxyimino-methyl)-imidazo[1,2-a]pyridin-3-yl]-phenyl}-3-(2,2,2-trifluoro-ethyl)-urea;

1-(3-{7-[(3,5-Dimethyl-isoxazol-4-ylmethoxyimino)-methyl]-imidazo[1,2-a]pyridin-3-yl}-phenyl)-3-(2,2,2-trifluoro-ethyl)-urea;

1-(3-{7-[(2,5-Dimethyl-2H-pyrazol-3-ylmethoxyimino)-methyl]-imidazo[1,2-a]pyridin-3-yl}-phenyl)-3-(2,2,2-trifluoro-ethyl)-urea;

1-(3-{7-[(5-tert-Butyl-[1,2,4]oxadiazol-3-ylmethoxy-imino)-methyl]-imidazo[1,2-a]pyridin-3-yl}-phenyl)-3-(2,2,2-trifluoro-ethyl)-urea;

1-(3-{7-[(Pyridin-3-ylmethoxyimino)-methyl]-imidazo[1,2-a]pyridin-3-yl}-phenyl)-3-(2,2,2-trifluoro-ethyl)-urea;

1-(3-{7-[(Furan-2-ylmethoxyimino)-methyl]-imidazo[1,2-a]pyridin-3-yl}-phenyl)-3-(2,2,2-trifluoro-ethyl)-urea;

1-[3-(7-{1-[2-Methoxy-ethoxyimino]-ethyl}-imidazo[1,2-a]pyridin-3-yl)-phenyl]-3-(2,2,2-trifluoro-ethyl)-urea;

1-(3-{7-[(1-Methyl-piperidin-4-yloxyimino)-methyl]-imidazo[1,2-a]pyridin-3-yl}-phenyl)-3-(2,2,2-trifluoro-ethyl)-urea;

1-{3-(7-{[2-(2-Methoxy-ethylamino)-ethoxyimino]-methyl}-imidazo[1,2-a]pyridin-3-yl)-phenyl]-3-(2,2,2-trifluoro-ethyl)-urea;

1-[3-(7-{[2-(2-Methanesulfonyl-ethylamino)-ethoxyimino]-methyl}-imidazo[1,2-a]pyridin-3-yl)-phenyl]-3-(2,2,2-trifluoro-ethyl)-urea;

1-(3-{7-{[3-(4-Methyl-piperazin-1-yl)-3-oxo-propoxyimino]-methyl}-imidazo[1,2-a]pyridin-3-yl)-phenyl]-3-(2,2,2-trifluoro-ethyl)-urea;

1-(3-{7-[(2-Amino-thiazol-4-ylmethoxyimino)-methyl]-imidazo[1,2-a]pyridin-3-yl}-phenyl)-3-(2,2,2-trifluoro-ethyl)-urea;

1-[3-(7-{Cyclopropyl-methoxyimino-methyl}-imidazo[1,2-a]pyridin-3-yl)-phenyl]-3-(2,2,2-trifluoro-ethyl)-urea;

1-[3-(7-{Cyclopropyl-hydroxyimino-methyl}-imidazo[1,2-a]pyridin-3-yl)-phenyl]-3-(2,2,2-trifluoro-ethyl)-urea;

1-[3-(7-{1-Methoxyimino-propyl}-imidazo[1,2-a]pyridin-3-yl)-phenyl]-3-(2,2,2-trifluoro-ethyl)-urea;

1-[3-(7-{1-Hydroxyimino-propyl}-imidazo[1,2-a]pyridin-3-yl)-phenyl]-3-(2,2,2-trifluoro-ethyl)-urea;

1-(3-{7-[(5-Methyl-isoxazol-3-ylmethoxyimino)-methyl]-imidazo[1,2-a]pyridin-3-yl}-phenyl)-3-(2,2,2-trifluoro-ethyl)-urea;

1-[3-(7-{1-[2-(2-Hydroxy-ethoxy)-ethoxyimino]-ethyl}-imidazo[1,2-a]pyridin-3-yl)-phenyl]-3-(2,2,2-trifluoro-ethyl)-urea;

1-[3-(7-{1-[3-Hydroxy-propoxyimino]-ethyl}-imidazo[1,2-a]pyridin-3-yl)-phenyl]-3-(2,2,2-trifluoro-ethyl)-urea;

1-(3-{7-[(3-Hydroxy-propoxyimino)-methyl]-imidazo[1,2-a]pyridin-3-yl}-phenyl)-3-(2,2,2-trifluoro-ethyl)-urea;

1-[3-(7-{Cyclobutyl-methoxyimino-methyl}-imidazo[1,2-a]pyridin-3-yl)-phenyl]-3-(2,2,2-trifluoro-ethyl)-urea;

1-[3-(7-{Cyclobutyl-hydroxyimino-methyl}-imidazo[1,2-a]pyridin-3-yl)-phenyl]-3-(2,2,2-trifluoro-ethyl)-urea;

1-[3-(7-{2-Cyclopropyl-1-methoxyimino-ethyl}-imidazo[1,2-a]pyridin-3-yl)-phenyl]-3-(2,2,2-trifluoro-ethyl)-urea;

1-[3-(7-{2-Cyclopropyl-1-hydroxyimino-ethyl}-imidazo[1,2-a]pyridin-3-yl)-phenyl]-3-(2,2,2-trifluoro-ethyl)-urea;

1-(3-{7-[(2-Guanidino-thiazol-4-ylmethoxyimino)-methyl]-imidazo[1,2-a]pyridin-3-yl}-phenyl)-3-(2,2,2-trifluoro-ethyl)-urea;

1-{3-[7-({3-[4-(2-Cyano-ethyl)-piperazin-1-yl]-propoxyimino}-methyl)-imidazo[1,2-a]pyridin-3-yl]-phenyl}-3-(2,2,2-trifluoro-ethyl)-urea;

1-[3-(7-{Cyclopropyl-hydroxyimino-methyl}-imidazo[1,2-a]pyridin-3-yl)-5-isopropoxy-phenyl]-3-(2,2,2-trifluoro-ethyl)-urea;

and

1-[3-(7-{Cyclopropyl-[2-hydroxy-ethoxyimino]-methyl}-imidazo[1,2-a]pyridin-3-yl)-phenyl]-3-(2,2,2-trifluoro-ethyl)-urea.

In one embodiment, the compound of formula (I) is a compound selected from:

1-[3-(7-{Cyclopropyl-[(E)-2-hydroxyethoxyimino]-methyl}-imidazo[1,2-a]pyridin-3-yl)-5-isopropoxy-phenyl]-3-(2,2,2-trifluoro-ethyl)-urea;

1-[3-(7-{Cyclopropyl-[(Z)-2-hydroxyethoxyimino]-methyl}-imidazo[1,2-a]pyridin-3-yl)-5-isopropoxy-phenyl]-3-(2,2,2-trifluoro-ethyl)-urea;

1-[3-(7-{Cyclopropyl-[(Z)-hydroxyimino]-methyl}-imidazo[1,2-a]pyridin-3-yl)-5-isopropoxy-phenyl]-3-(2,2,2-trifluoro-ethyl)-urea;

and

1-[3-(7-{Cyclopropyl-[(E)-hydroxyimino]-methyl}-imidazo[1,2-a]pyridin-3-yl)-5-isopropoxy-phenyl]-3-(2,2,2-trifluoro-ethyl)-urea.

In the specification, references to Formula (I) include formulas such as (Ia), (Ib), (Ic) and (Id) and sub-groups, examples or embodiments of formulae (I), (Ia), (Ib), (Ic) and (Id) unless the context indicates otherwise.

Thus for example, references to inter alia therapeutic uses, pharmaceutical formulations and processes for making compounds, where they refer to formula (I), are also to be taken as referring to formulae (I), (Ia), (Ib), (Ic) and (Id), and sub-groups, examples or embodiments of formulae (I), (Ia), (Ib), (Ic) and (Id).

Similarly, where preferences, embodiments and examples are given for compounds of the formula (I), they are also applicable to formulae (I), (Ia), (Ib), (Ic) and (Id), and sub-groups, examples or embodiments of formulae (I), (Ia), (Ib), (Ic) and (Id), unless the context requires otherwise.

Methods for the Preparation of Compounds of Formula (I)

In this section, as in all other sections of this application unless the context indicates otherwise, references to formula (I) also include all other sub-groups and examples thereof as defined herein.

Compounds of the formula (I) can be prepared in accordance with synthetic methods well known to the skilled person. Oximes can be synthesised from ketones and aldehydes using known reagents. An aldehyde intermediate can be converted to the aldoxime or a ketone intermediate can be converted to the ketoxime using hydroxylamine hydrochloride in a protic solvent, e.g. ethanol, in the presence of a base, e.g. pyridine. The oxime compound can then be alkylated as required using an appropriate electrophile in the presence of a base (e.g. cesium carbonate or potassium hydroxide) and solvent (e.g. DMSO or ethanol). Appropriate electophiles include halides e.g. 2-bromo-ethanol, or using an appropriately activated alcohol (e.g. methanesulfonic acid pyridin-3-ylmethyl ester), or an alpha-beta unsaturated carbonyl compound (e.g. 2-propenoic acid 1,1-dimethylethyl ester). Alternatively the compound can be alkylated with the appropriate linker groups e.g. 1-bromo-2-chloro-ethane using cesium carbonate in DMSO and then reacted to form the desired substituent. Alternatively the compound can be alkylated with the appropriately protected linker groups which can then be converted to the desired $R^2$ group. For example the bromoallkoxysilane protected compound such as (2-bromoethoxy)(tert-butyl)dimethylsilane, a boc protected haloalkylamine or the N-allkoxylbenzylamine compound can be reacted with the hydroxyimino compound in the presence of a base (e.g. cesium carbonate) and solvent (e.g. DMSO). The protecting group is then removed, for example the silane group can be removed with acid e.g. acetic acid. The aldehyde intermediate in dry THF can also be converted to a ketone using Grignard reagent e.g. cyclopropylmagnesium bromide under an inert atmosphere and then oxidation e.g. using manganese oxide. For example, to imidazo[1,2-a]pyridine-7-carboxaldehyde in aprotic solvent THF can be added methylmagnesium bromide in diethylether under an inert atmosphere, and the resulting hydroxyl compound can then be oxidized to the methyl ketone.

In addition compounds of formula (I) are readily prepared by palladium mediated coupling chemistries between aromatic chloro, bromo, iodo, or pseudo-halogens such as a trifluoromethanesulphonate (triflate) or tosylate compounds, and aromatic boronic acids or stannane derivatives. In particular, Suzuki coupling chemistry is broadly applicable to synthesis of these compounds. The Suzuki reaction can be carried out under typical conditions in the presence of a palladium catalyst such as bis(tri-t-butylphosphine)palladium, tetrakis-(triphenylphosphine)palladium or a palladacycle catalyst (e.g. the palladacycle catalyst described in Bedford, R. B. and Cazin, C. S. J. (2001) Chem. Commun., 1540-1541) and a base (e.g. a carbonate such as potassium carbonate) as discussed in more detail below. The reaction may be carried out in polar solvent, for example an aqueous solvent system, including aqueous ethanol, or an ether such as dimethoxyethane or dioxane, and the reaction mixture is typically subjected to heating, for example to a temperature of 80° C. or more, e.g. a temperature in excess of 100° C.

As illustrated in Scheme 1A, the imidazo[1,2-a]pyridine core can be synthesised from commercially available starting materials as outlined below to give a 3,7-disubstituted ring.

Scheme 1A

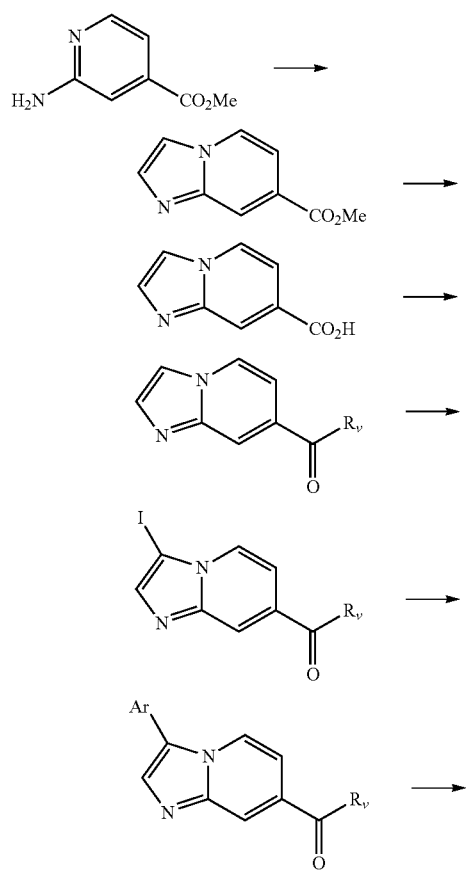

-continued

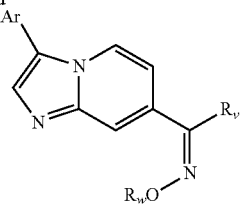

2-amino-isonicotinic acid methyl ester in an appropriate solvent and base can be cyclised under reflux with chloroacetaldehyde to give the imidazopyridine ring.

For synthesis of the $R^2$ group of compounds of formula (I) the carboxylic ester is converted to the ketone. Ketones can be synthesized from the corresponding carboxylic acid via the N,O-dimethylhydroxamic acid (Weinreb Amide) or the N-methyl,O-t-butyl hydroxamic acid (Weinreb type Amide) intermediate and subsequent reaction with the appropriate Grignard reaction (Labeeuw, O. et al Tetrahedron Lett 2004, 45 (38), 7107-7110.). Derivatisation to the corresponding Weinreb Amide uses N,O-dimethylhydroxylamine hydrochloride as described in L. De Luca, G. Giacomelli, M. Taddei, J. Org. Chem., 2001, 66, 2534-2537. Conversion of the standard aromatic Weireb Amide to a methyl ketone requires methylene-triphenyl-lambda*5*-phosphane in a solvent such at tetrahydrofuran as reported in Murphy, J. A. et al Org Lett 2005, 7 (7), 1427-1429 or can be achieved directly using alkylidenetriphenylphosphoranes. Alternatively this can be achieved stepwise by addition of a Grignard reagent (Labeeuw, O. et. al. Tetrahedron Letters 2004, 45(38), 7107-7110) and by oxidation of the resulting alcohol.

Alternatively ketones can be prepared from the chloride using vinylethertin (Stille type) coupling with haloaromatic or haloheteroaromatic compounds. As an example the acetyl ketone can be prepared by heating tributyl-(1-ethoxy-vinyl)-stannane, lithium chloride and tetrakis(triphenylphosphine)-palladium(0) in solvent such as acetonitrile or via a Heck type reaction reported in Mo, J. Angew Chem, Int Ed, 2006, 45(25), 4152.

Ketone compounds can also be prepared using cross-coupling reactions, for example palladium mediated (Tetrahedron Lett., 1997, 38 (11), 1927-1930) or copper mediated (Org. Lett., 2003, 5 (8), 1229-1231) reaction can be performed with the appropriate acid chloride with the appropriate 7-chloroimidazopyridinyl compound.

The imidazo[1,2-a]pyridine-7-derivative, for example the imidazo[1,2-a]pyridine-7-carboxylic acid methyl ester or aldehyde, in an appropriate solvent can then be iodinated, for example using N-iodosuccinimide at room temperature.

Appropriate functionality can then be added at the halogenated position, for example using a range of metal-catalysed reactions. In particular, appropriately functionalised boronic acids, trifluoroboronates, or their boronate esters may react with the aryl halide. This transformation, commonly known as the Suzuki reaction, has been reviewed by Rossi et al (2004), Synthesis 15, 2419.

The Suzuki reaction is often carried out in mixtures of water and organic solvents. Examples of suitable organic solvents include toluene, tetrahydrofuran, 1,4-dioxane, 1,2-dimethoxyethane, acetonitrile, N-methylpyrrolidinone, ethanol, methanol and dimethylformamide. The reaction mixture is typically subjected to heating, for example to a temperature in excess of 100° C. The reaction is carried out in the presence of a base. Examples of suitable bases include sodium carbonate, potassium carbonate, cesium carbonate and potassium phosphate. Examples of suitable catalysts include bis(tri-t-butylphosphine)palladium(0), tris(dibenzylideneacetone)dipalladium(0), bis(triphenylphosphine)palladium(II) chloride, palladium(II) acetate, tetrakis(triphenylphosphine)palladium(0), bis(tricyclohexylphosphine) palladium(0), [1,1'-bis(diphenylphosphino)-ferrocene]dichloropalladium (II), dichlorobis(tri-o-tolylphosphine)palladium(II), 2'-(dimethylamino)-2-biphenylyl-palladium(II) chloride dinorbornylphosphine complex and 2-(dimethylamino)ferrocen-1-yl-palladium(II) chloride dinorbornylphosphine complex. In some cases additional ligands may be added to facilitate the coupling reaction. Examples of suitable ligands include tri-t-butylphosphine, 2,2-bis(diphenylphosphino)-1,1-binaphthyl, triphenylphosphine, 1,2-bis(diphenylphosphino)ethane, 1,1'-bis(diphenylphosphino)ferrocene, tricyclohexylphosphine, 9,9-dimethyl-4,5-bis(diphenylphosphino)xanthene, 1,3-bis(diphenylphosphino)propane, 2-(di-t-butylphosphino)biphenyl, 2-dicyclohexylphosphino-2'-(n,n-dimethylamino)-biphenyl, tri-o-tolylphosphine, 2-(dicyclohexylphosphino)biphenyl, 2-dicyclohexylphosphino-2',4',6'-triisopropylbiphenyl, tri(2-furyl)phosphine, 2-dicyclohexylphosphino-2',6'-dimethoxybiphenyl and 2-di-tert-butylphosphino-2',4',6'-triisopropylbiphenyl.

Other examples of possible metal catalysed functionalisations of the halide are reactions with organo-tin reagents (the Stille reaction), with Grignard reagents and reaction with nitrogen nucleophiles. A general overview, and further leading references, of these transformations is presented in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

In particular, one reaction which can be utilised is the Buchwald-Hartwig type reaction (see Review: J. F. Hartwig (1998), Angew. Chem. Int. Ed. 37, 2046-2067) which provides a means for palladium-catalyzed synthesis of aryl amines. The starting materials are aryl halides or pseudohalides (for example triflates) and primary or secondary amines, in the presence of a strong base such as sodium tert-butoxide and a palladium catalyst such as tris-(dibenzylideneacetone)-di-palladium ($Pd_2$ $(dba)_3$), or 2,2'-bis(diphenylphosphino)-1'1-binaphthyl (BINAP).

In particular, for synthesis compounds of formula (I) the aryl halide can be reacted with 3-aminobenzeneboronic acid using an appropriate metal catalyst e.g. bis(triphenylphosphine)palladium(II) chloride to form the amino precursor for secondary amine bond formations.

This sequence of reactions outlined in Scheme 1A can be alternated as outlined in Scheme 1B or 1C.

Scheme 1B

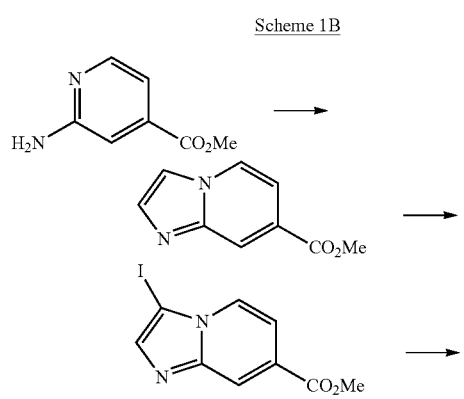

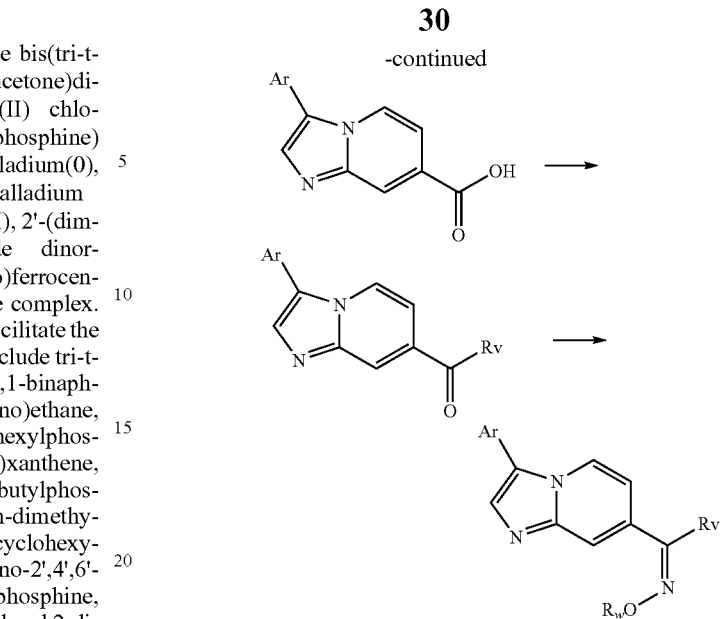

In Scheme 1B, the imidazo[1,2-a]pyridine-7-carboxylic acid methyl ester is iodinated first and the metal-catalysed coupling reaction performed, before conversion of the methyl ester to the aldehyde group.

Scheme 1C

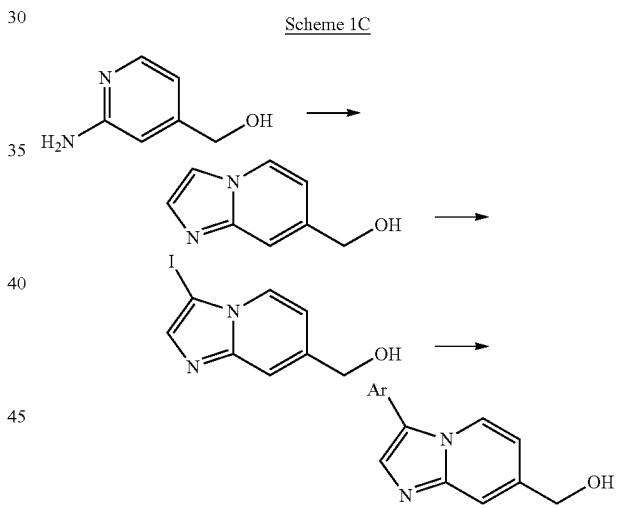

In Scheme 1C, the imidazo[1,2-a]pyridine-7-methanol can be synthesized directly from the 4-hydroxymethyl-pyridin-2-ylamine. Imidazo[1,2-a]pyridine-7-methanol is also commercially available. The methanol compound can be iodinated for example using N-iodosuccinimide, and then oxidized for example using manganese oxide, or vice versa. This iodo compound can then be used in the metal-catalysed coupling reaction.

Alternatively the methanol group can be converted first into the ketone and then replacement of iodine by aromatic group.

Alternatively the 4-chloro-pyridin-2-ylamine or 4-bromo-pyridin-2-ylamine in an appropriate solvent and base can be cyclised under reflux with chloroacetaldehyde to give the 7-halo-imidazopyridine ring (as shown in Scheme 2). The halogen functionality at the 7-position of the imidazo[1,2-a] pyridine can then be converted to an oxime by either of the two routes outlined in Scheme 2.

Scheme 2

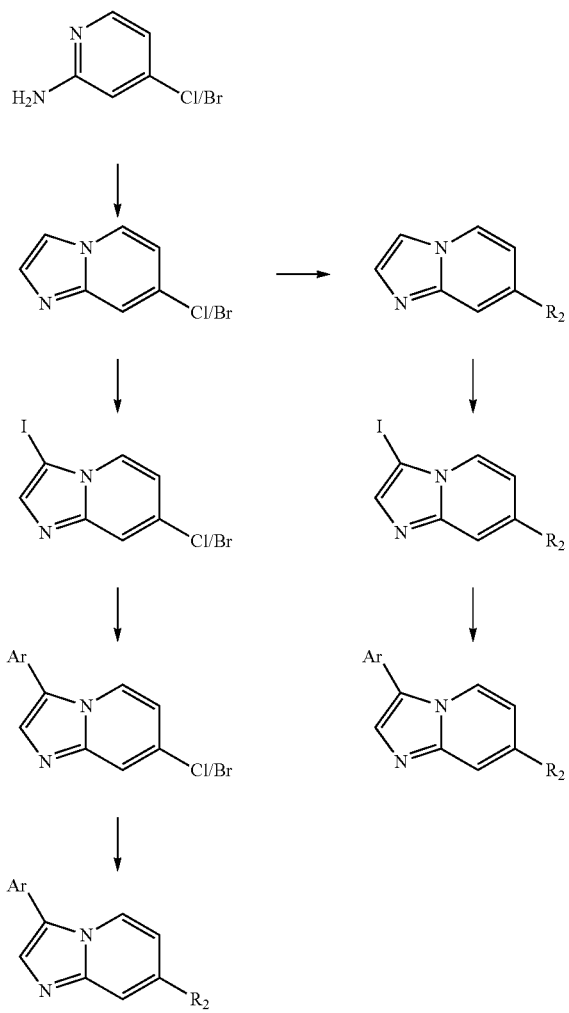

The halide can be converted to the acid using n-butyllithium or magnesium and subsequent reaction of the intermediate with a carbonylating agent such as $CO_2$ produces the carboxylic acid for use as described herein. In addition, the halide can be converted using carbon monoxide and palladium catalyst to the aldehyde. The halide can also be converted directly to the ester using carbon monoxide, palladium catalyst and the appropriate alcohol. This can then converted as described herein.

Other conversions of aromatic bromides to aromatic aldehydes can take place using the Stille carbonyl synthesis (Stille, JACS, 1983, 105, 7175), or the Bodroux-Chichibabinaldehyde synthesis described in Einchorn, J, Tetrahedron Lett., 1983, 27, 1791. The aldehyde can then be oxidised to the acid and converted to an oxime as described herein.

Polyfunctional 2-amino-5-bromopyridines or the aromatic bromides can be converted to aldehyde via Grignard type formation and quenching with DMF (Misra, Bioorg. Med. Chem. Lett., 2004, 14(11), 2973) or they can be converted to ethyl esters via standard palladium carbonylation in the presence of alcohol (Cheung, M. Heterocycles, 2001, 55, 1583).

Alternatively the 4-methyl-pyridin-2-ylamine can be used in the cyclisation reaction to give the 7-methyl-imidazo[1,2-a]pyridine ring, which alternatively is commercially available. The methyl can then be oxidised to the aldehyde using the Étard reaction or to the carboxylic acid using an oxidising agent such as permanganate. The Étard reaction involves the direct oxidation of an aromatic or heterocyclyl bound methyl group to an aldehyde using chromyl chloride.

Alternatively the ethyl imidazo[1,2-a]pyridine-7-carboxylate, which is also commercially available, can be used as the startpoint for the conversion or iodinations and metal-catalysed reactions.

Scheme 3

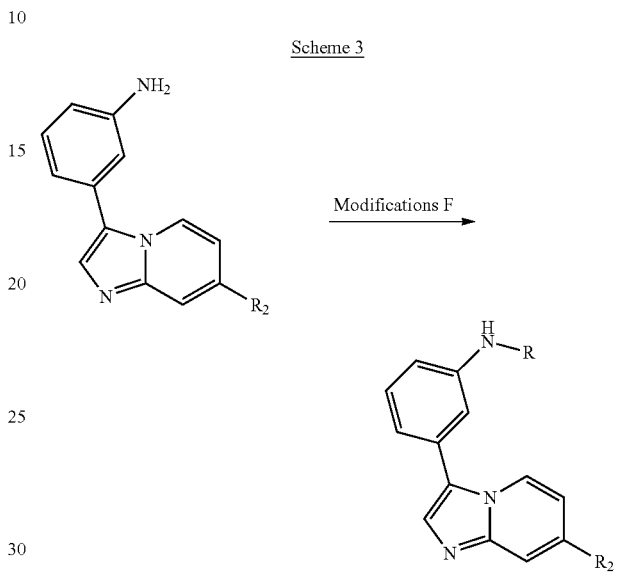

A range of compounds of formula (I) can be accessed by use of 3-aminobenezeboronic acid in the Suzuki reaction and subsequent derivatisation. In particular, as outlined in Scheme 3, the amine functionality introduced can be used to synthesise for example sulfonyl ureas, sulphonamides, ureas, amides, secondary amines and carbamates.

An amide bond can be prepared by the reaction of a carboxylic acid or a reactive derivative thereof and an amine under standard amide forming conditions. The coupling reaction between the carboxylic acid and the amine is preferably carried out in the presence of a reagent of the type commonly used in the formation of peptide linkages. Examples of such reagents include 1,3-dicyclohexylcarbodiimide (DCC) (Sheehan et al, J. Amer. Chem. Soc., 1955, 77, 1067), 1-ethyl-3-(3'-dimethylaminopropyl)-carbodiimide (referred to herein either as EDC or EDAC but also known in the art as EDCI and WSCDI) (Sheehan et al, J. Org. Chem., 1961, 26, 2525), uronium-based coupling agents such as O-(7-azabenzotriazol-1-yl)-N,N,N',N'-tetramethyluronium hexafluorophosphate (HATU) or O-(Benzotriazol-1-yl)-N,N,N',N'-tetramethyluronium tetrafluoroborate (TBTU) and phosphonium-based coupling agents such as 1-benzo-triazolyloxytris-(pyrrolidino)phosphonium hexafluorophosphate (PyBOP) (Castro et al, Tetrahedron Letters, 1990, 31, 205). Carbodiimide-based coupling agents are advantageously used in combination with 1-hydroxy-7-azabenzotriazole (HOAt) (L. A. Carpino, J. Amer. Chem. Soc., 1993, 115, 4397) or 1-hydroxybenzotriazole (HOBt) (Konig et al, Chem. Ber., 103, 708, 2024-2034). Preferred coupling reagents include TBTU, EDC (EDAC) or DCC in combination with HOAt or HOBt.

The coupling reaction is typically carried out in a non-aqueous, non-protic solvent such as acetonitrile, 1,4-dioxane, dimethylsulphoxide, dichloromethane, dimethylformamide or N-methylpyrrolidine, or in an aqueous solvent optionally together with one or more miscible co-solvents. The reaction can be carried out at room temperature or, where the reactants are less reactive (for example in the case of electron-poor anilines bearing electron withdrawing groups such as sulphonamide groups) at an appropriately elevated temperature. The reaction may be carried out in the presence of a non-interfering base, for example a tertiary amine such as triethylamine or N,N-diisopropylethylamine.

As an alternative, a reactive derivative of the carboxylic acid, e.g. an anhydride or acid chloride, may be used. Reaction with a reactive derivative such an anhydride, is typically accomplished by stirring the amine and anhydride at room temperature in the presence of a base such as pyridine.

Amines for use in the reaction can be obtained from commercial sources or can be prepared by any of a large number of standard synthetic methods well known by those skilled in the art, see for example Advanced Organic Chemistry by Jerry March, 4$^{th}$ Edition, John Wiley & Sons, 1992, and Organic Syntheses, Volumes 1-8, John Wiley, edited by Jeremiah P. Freeman (ISBN: 0-471-31192-8), 1995, and see also the methods described in the experimental section below. For example the appropriate nitro-compound may be reduced to give the corresponding amino-compound. The reduction may be carried out by standard methods such as catalytic hydrogenation, for example in the presence of palladium on carbon in a polar solvent such as ethanol or dimethylformamide at room temperature. As an alternative, reduction may be effected using a reducing agent such as tin (II) chloride in ethanol, typically with heating, for example to the reflux temperature of the solvent.

Ureas can also be prepared using standard methods. For example, such compounds can be prepared by reacting an amino compound with a suitably substituted isocyanate in a polar solvent such as DMF. The reaction is conveniently carried out at room temperature.

Alternatively, ureas of the formula (I) can be prepared by reacting an amine with an appropriately substituted amine in the presence of carbonyl diimidazole (CDI). The reaction is typically carried out in a polar solvent such as THF with heating (for example using a microwave heater) to a temperature of up to about 150° C. Instead of using CDI, the coupling of the two amines to form the urea can be effected using triphosgene (bis(trichloromethyl) carbonate) in the presence of a non-interfering base such as triethylamine, in a solvent such as dichloromethane at room temperature or below. As a further alternative to CDI, phosgene may be used instead of triphosgene.

In addition the amide or urea compounds can be synthesised by use of an appropriate substituted boronic acid e.g. 1-methyl-3-[3-(4,4,5,5-tetramethyl-[1,3,2]dioxaborolan-2-yl)-phenyl]-urea or 3-methoxy-5-nitro-phenyl boronic acid pinacol ester in the Suzuki reaction with an appropriately substituted imidazo[1,2-a]pyrimidine. These can be synthesised as described herein.

Compounds of the formula (I) containing a carbamate can be made using standard methods for the synthesis of carbamates, for example by reaction of an amino compound with a chloroformate derivative of the formula $R^1$—O—C(O)—Cl under conditions well known to the skilled person.

Compounds of the formula (I) containing a sulfonamide can be prepared from amino-compounds by standard methods for the formation of sulphonamides. For example, an amine compound can be reacted with sulphonyl chlorides of the formula $R^1SO_2Cl$ or anhydrides of the formula $(R^1SO_2)_2O$. The reaction is typically carried out in an aprotic solvent such as acetonitrile or a chlorinated hydrocarbon (for example dichloromethane) in the presence of a non-interfering base such as a tertiary amine (e.g. triethylamine or diisopropylethyl amine or pyridine). Alternatively, where the base is a liquid, for example pyridine, the base itself may be used as the solvent for the reaction.

Sulfonyl ureas can be prepared from the amine compound by reaction in an appropriate aprotic solvent, such as THF, with a base e.g. triethylamine, and the appropriately substituted sulfamoyl chloride.

Other compounds of formula (I) including alternative examples of $R^1$ such as thioureas, thioamides, thiocarbamates e.g. O-substituted thiocarbamates or S-substituted thiocarbamates, dithiocarbamates, amidines, and guanidines, can be synthesised from the amine intermediate using a range of well known functional group interconversions as described in Advanced Organic Chemistry by Jerry March, 4$^{th}$ Edition, John Wiley & Sons, 1992.

Primary amines can alternatively be prepared by reduction of the corresponding nitro-compound under standard conditions. The reduction may be effected, for example by catalytic hydrogenation in the presence of a catalyst such as palladium on carbon in a polar solvent such as ethanol or dimethylformamide at room temperature.

Appropriate starting material and reagents for these reactions can be obtained commercially or by any of a large number of standard synthetic methods well known to those skilled in the art, for example see Advanced Organic Chemistry by Jerry March, 4$^{th}$ Edition, John Wiley & Sons, 1992, and Organic Syntheses, Volumes 1-8, John Wiley, edited by Jeremiah P. Freeman (ISBN: 0-471-31192-8), 1995, and see also the methods described in the experimental section below. For example a range of appropriate functionalized aniline and amino pyridine starting materials, and metal catalysts are commercially available.

Many boronates, for example boronic acids, esters or trifluoroborates, suitable for use in preparing compounds of the invention are commercially available, for example from Boron Molecular Limited of Noble Park, Australia, or from Combi-Blocks Inc. of San Diego, USA. Where the appropriately substituted boronate is not commercially available, they can be prepared by methods known in the art, for example as described in the review article by Miyaura, N. and Suzuki, A. (1995) Chem. Rev. 95, 2457. Thus, boronates can be prepared by reacting the corresponding bromo-compound with an alkyl lithium such as butyl lithium and then reacting with a borate ester e.g. ($^i$PrO)$_3$B. The reaction is typically carried out in a dry polar solvent such as tetrahydrofuran at a reduced temperature (for example −78° C.). Boronate esters (for example a pinacolatoboronate) can also be prepared from a bromo-compound by reaction with a diboronate ester such as bis(pinacolato)diboron in the presence of a phosphine such as tricyclohexyl-phosphine and a palladium (0) reagent such as tris(dibenzylideneacetone)-dipalladium (0). The formation of the boronate ester is typically carried out in a dry polar aprotic solvent such as dioxane or DMSO with heating to a temperature of up to 100° C., for example around 80° C. The resulting boronate ester derivative can, if desired, be hydrolysed to give the corresponding boronic acid or converted into the trifluoroborate.

All of the reactions described above can be used to functionalise alternative heterocyclyl templates of formula (I), whose synthesis is outlined below.

Once synthesised, a range of functional group conversions can be employed on the substituted imidazopyridine compounds to produce further compounds of formula (I). For example, some of the following reactions can be used hydrogenation, hydrolysis, deprotection, and oxidation, to convert one compound of formula (I) into an alternative compound of formula (I).

Pyrazolo[1,5-a]pyrimidines

The pyrazolo[1,5-a]pyrimidine template can be synthesised from the appropriately substituted aminopyrazole (VI) and fragments (VII) as shown in Scheme 5A, where $R_a$ can be hydrogen or A-R₁. This may occur by a one step or two step process, where $X_a$ and $X_b$ are electrophilic carbons (i.e. carbonyl, masked carbonyl i.e. acetal, enamine, conjugated alkenes or alkynes) (Perkin I, J. C. S. (1979), 3085-3094). $X_o$ is an appropriate substituent, either a group $R_2$ or groups such as halogen or pseudo halogens or methyl, which will allow reaction to introduce $R_2$ as described herein. Cyclisation of the pyrazole (VI) with an appropriately substituted free or masked 1,3-dicarbonyl derivative can be used to prepare substituted pyrazolo[1,5-a]pyrimidines. Cyclisation occurs typically in an alcohol solvent or in toluene or in acetic acid, and may have additives such as piperidine, sodium ethoxide, HCl, AcOH, pTsOH, or ZnCl₂ present (J. Med. Chem. (2001), 44 (3), 350-361; Bull. Korean Chem. Soc. (2002), 23 (4), 610-612; Australian Journal of Chemistry (1985), 38(1), 221-30).

A particular synthetic scheme for the preparation of disubstituted pyrazolo[1,5-a]pyrimidines is outlined in Scheme 5B. The pyrazolopyrimidine ring is formed by reaction of a substituted malonaldehyde as fragment VII with aminopyrazole. The substituted malonaldehyde can be substituted with methyl, or with a latent functionality e.g. a halogen as in 2-bromo-malonaldehyde, which allows further derivatisation at this position as in the scheme shown below using the reactions outlined herein.

Scheme 5B

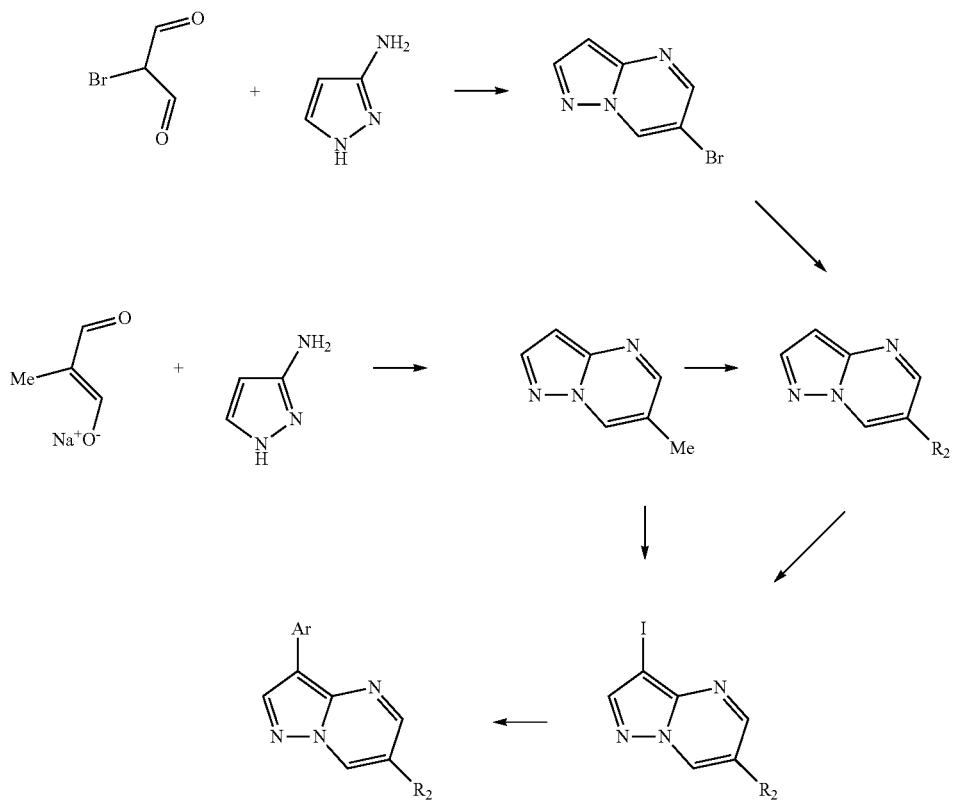

In the cyclisation reaction, the malonaldehyde in solvent is added to 3-aminopyrazole followed by acid e.g. glacial acetic acid. The reagents are then cyclised upon heating under reflux. The compound of formula (I) can then be synthesised using the oxidative and coupling process outlined herein.

Compounds of formula (VI) and (VII) are known compounds or can be prepared by analogy to known methods. Many pyrazoles of formula (VI) are commercially available. Alternatively they can be obtained from known methods e.g. from ketones in a process described in EP308020 (Merck), or the methods discussed by Schmidt in Helv. Chim. Acta. (1956), 39, 986-991 and Helv. Chim. Acta. (1958), 41, 1052-1060 or by conversion of the pyrazoles of formula (VI) or the compound of formula (I) where $R^a$ is hydrogen, halogen, nitro, ester, or amide to the desired $R^1$ functionality by standard methods known to a person skilled in the art. For example, where $R^1$ is halogen, coupling reactions with tin or palladium chemistry could be performed as described herein.

Alternatively the pyrazolo[1,5-a]pyrimidine-6-carboxylic acid or aldehyde are commercially available and can be used in the reactions described herein to synthesise di-substituted pyrazolo[1,5-a]pyrimidines.

Scheme 5A

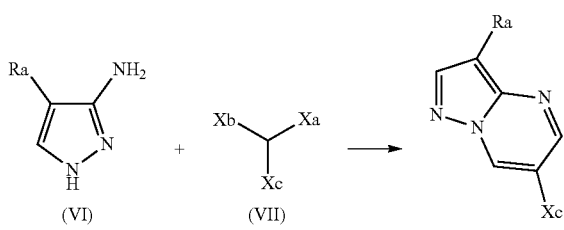

Pyrazolo[1,5-a]pyrazines

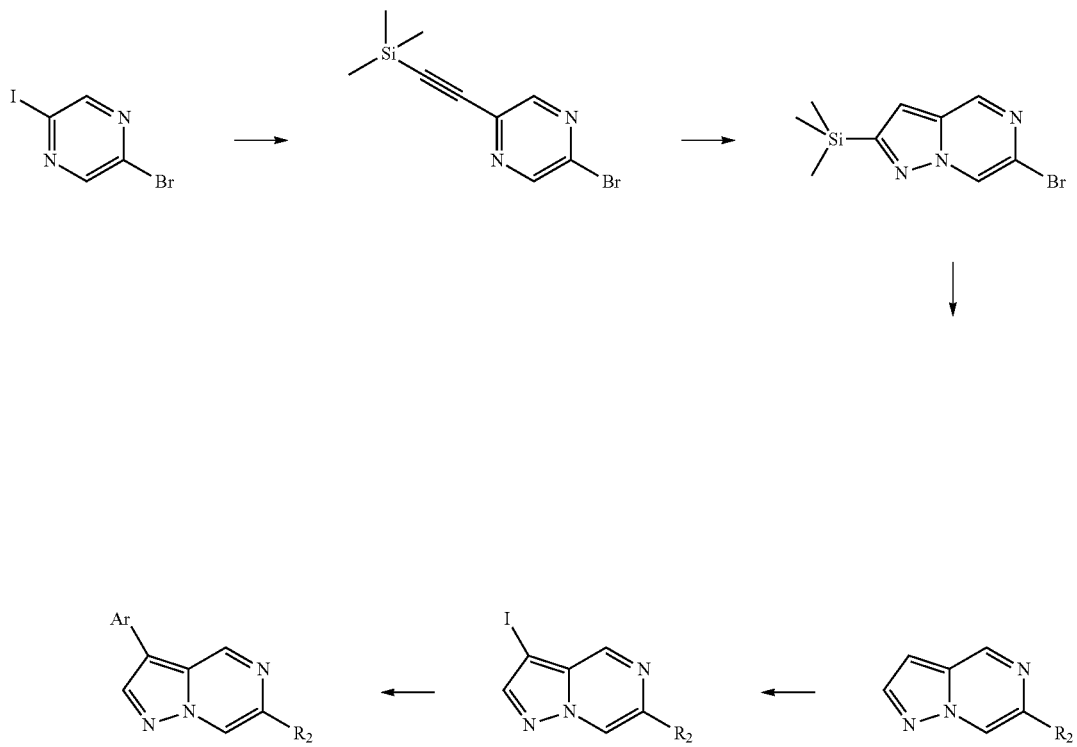

Reaction of a mixture of 2-bromo-5-iodo-pyrazine and copper (1) iodide under inert conditions in an appropriate solvent and base e.g. DMF/Et$_3$N with ethynyl-trimethyl-silane using a palladium catalyst e.g. Pd(PPh$_3$)$_4$ at room temperature gives 2-Bromo-5-trimethylsilanylethynyl-pyrazine. This material can be used without further purification and reacted to form 6-bromo-2-trimethylsilanyl-pyrazolo[1,5-a]pyrazine using O-(mesitylenesulfonyl)hydroxylamine to form the N-amino adduct. This can then be cyclised by reacting with base e.g. K$_2$CO$_3$ to form pyrazolopyrazine core (Scheme 6).

Appropriate groups can then be introduced by halogenation and reaction of the latent functionality in the metal catalysed reactions and the ketone-aldehyde and oxime conversions at the other position as described herein.

Pyrazolo[1,5-a]pyridines

O-(Mesitylenesulfonyl)hydroxylamine is reacted with 3-substituted-pyridine under inert conditions to form the N-aminopyridine which can be used without further purification (Scheme 7). Cyclisation of the N-adduct using base (K$_2$CO$_3$) and 2-benzenesulfonyl-3-dimethylamino-acrylic acid methyl ester in an inert atmosphere gives the 3-carboxylic acid ester pyrazolo[1,5-a]pyridine. The carboxylic ester can be removed for example by saponification using sodium hydroxide to form the acid and then decarboxylation in polyphosphoric acid. The bromide can then be converted to the desired R$^2$ group using the methods described herein.

Scheme 7

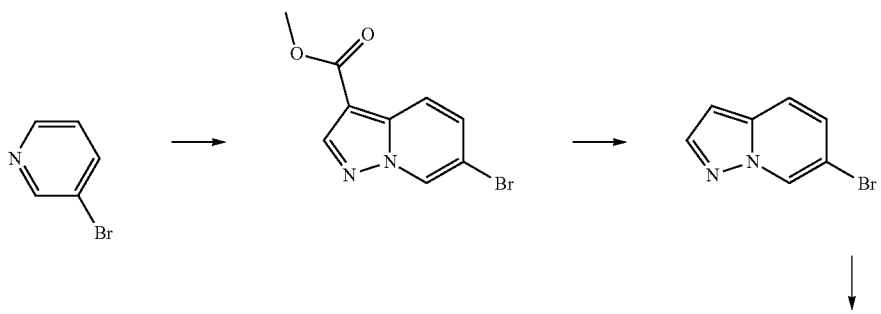

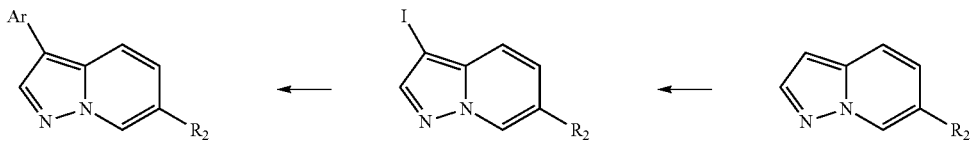

Iodination with N-iodosuccinimide and metal catalysed reaction of aryl halides, can be used to introduced the required functionality as outlined herein.

Imidazo[4,5-b]pyridines

An imidazo[4,5-b]pyridine ring system may be constructed by reaction of an aniline with 2-chloro-3-amino pyridine as described in J. Heterocyclic Chemistry (1983), 20(5), 1339 (Scheme 8).

Scheme 8

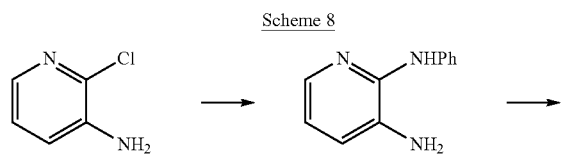

-continued

It will be appreciated that the resultant bicyclic ring in Scheme 8 can be functionalised by halogenation or alkylation and converted to $R^2$ as described herein.

A more functionalized intermediate could be prepared for example as outlined in Scheme 9A based on methods described in U.S. Ser. No. 06/723,735.

Scheme 9A

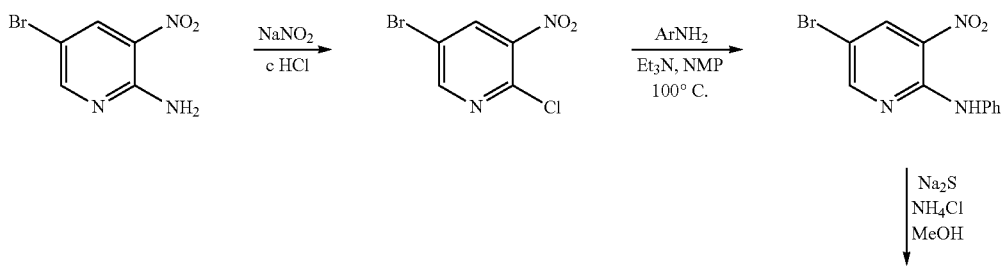

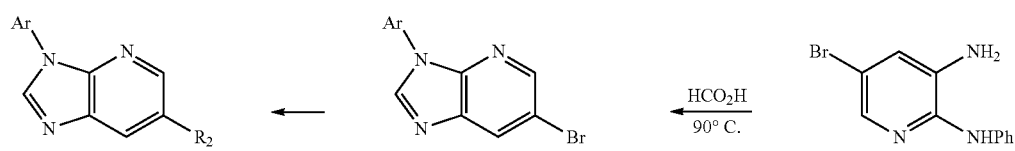

As described herein the aryl halides similar to that shown above may undergo a range of metal catalysed reactions to generate the required compounds of formula (I).

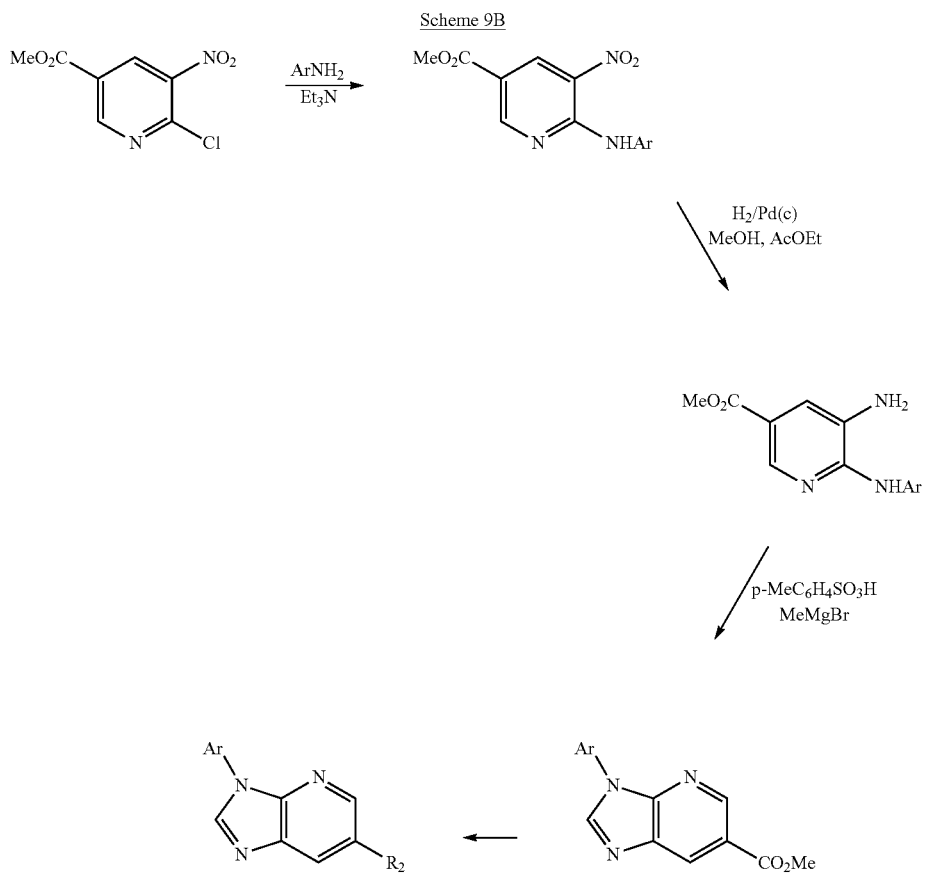

Scheme 9B

Alternatively they could be synthesised as outlined above in Scheme 9B.

Imidazo[4,5-c]pyridines

A 3-aryl-3H-imidazo[4,5-c]pyridine ring system may be constructed by reaction of 3H-imidazo[4,5-c]pyridine with an aryl iodide as discussed in Biorg. Med. Chem. Lett. (2004), 14, 5263 (Scheme 10).

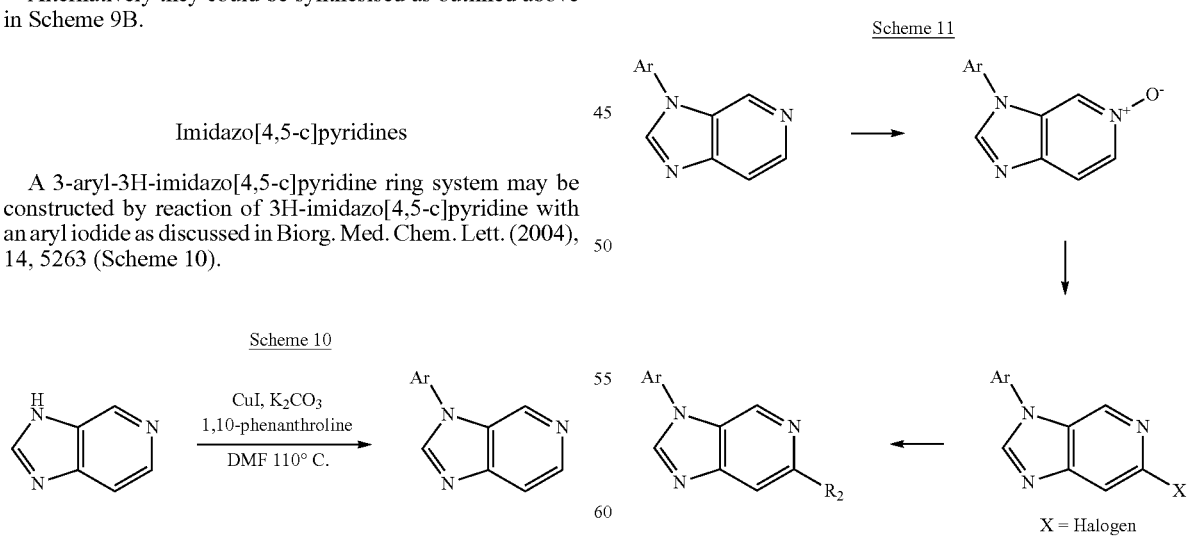

It is reported that the regioisomeric products may be separated by chromatography. A possible way to further elaborate this material to give the desired substitution pattern is illustrated below (Scheme 11).

Reaction with an oxidizing agent, such as 3-chloro perbenzoic acid, could be used to prepare the N-oxide which may be rearranged to the disubstituted 3H-imidazo[4,5-c]pyridine with several reagents e.g. POCl₃, SOCl₂. The regioisomeric products could then be separated by chromatography. Displacement of the halogen with potassium cyanide in DMSO or reaction with palladium and Zn(CN)₂ (Bioorg. Med. Chem. Lett., 2003, 13 (9), 1591), produces the nitrile which can be converted to the acid as outlined previously.

An alternative strategy is shown in Scheme 12. The synthesis of 6-chloro-3H-imidazo[4,5-c]pyridine is described in J. Heterocyclic Chem (1965), 2(2), 196-201. The chloro group may be converted as outline herein. Subsequent elaboration to the N-aryl compounds could then be achieved according to the conditions shown in Scheme 10.

Scheme 12

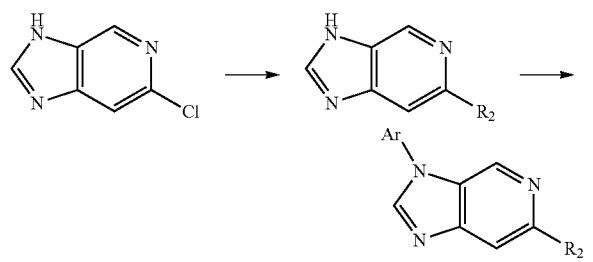

1,5-Diaryl-1H-benzoimidazole

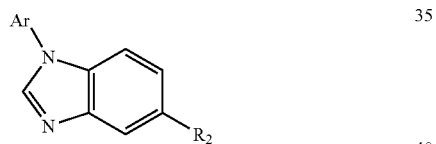

A synthesis of 1,5-diaryl-1H-benzoimidazoles is reported in Bioorg. Med. Chem. Lett. (2003), 13, 2485-2488 (Scheme 13).

Scheme 13

1. ArNH₂, NMP 110° C.
2. Zn/AcOH, 60° C.
3. HC(OEt)₃, 100° C.

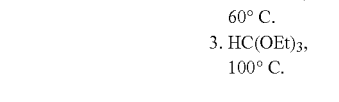

Displacement of fluorine from 4-bromo-1-fluoro-2-nitrobenzene with an appropriate aniline followed by reduction and cyclisation with triethyl orthoformate gives the bromobenzoimidazole with the desired substitution pattern. The product may be further elaborated by reaction of the bromide as described herein to give 1,5-disubstituted benzoimidazoles.

1,5-disubstituted benzoimidazoles maybe synthesised using analogous chemistry to that described in Scheme 11.

Imidazo[1,2-c]pyrimidines

Di-substituted imidazo[1,2-c]pyrimidines can be prepared as outlined in Scheme 14.

Scheme 14

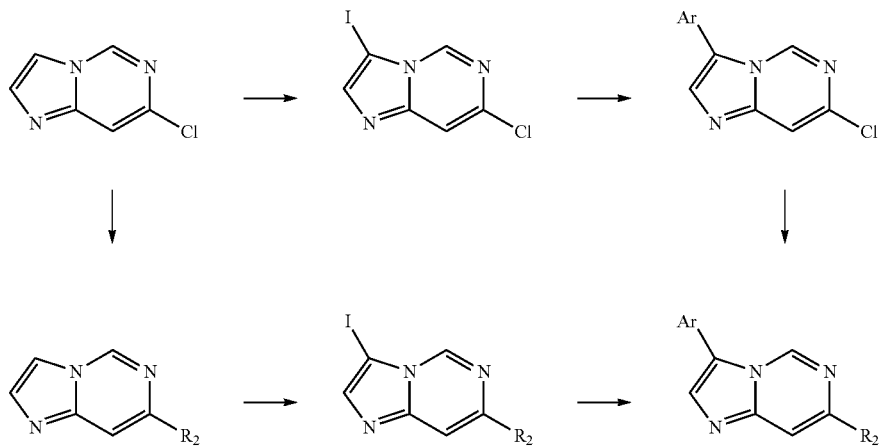

This starts from 7-chloro-imidazo[1,2-c]pyrimidine, whose synthesis has been described in Yanai et al, Heterocyclic compounds. XVIII. Synthesis of imidazo[1,2-c]-pyrimidine derivatives, Yakugaku Zasshi (1974), 94(12), 1503-14. This material can then be further elaborated using any of the reactions described above.

Where the 3-position is an aryl or heteroaryl group the $S_N$ Ar group can be replaced with a standard palladium cross coupling reaction using similar chemistries as described herein (Scheme 16).

Scheme 16

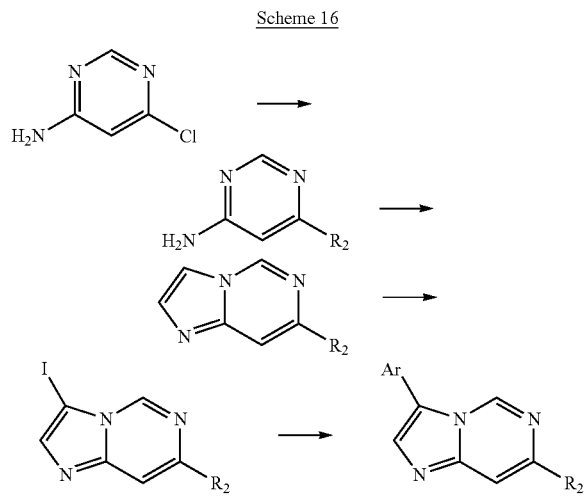

Alternatively the 6-chloropyrimid-4-ylamine can be reacted to form the bicyclic ring system and then convert the chloro to the $R_2$ group.

Alternatively the 6-amino-pyrimidine-4-carboxylic acid can be used as the starting material.

Imidazo[1,2-c]pyrimidin-5-one 3,7-disubstituted imidazo[1,2-c]pyrimidin-5-ones can be prepared from the 7-Chloro-6H-imidazo[1,2-c]pyrimidin-5-one (CAS number 56817-09-5) whose synthesis is described in Maggiali et al (1982), Acta Naturalia de l'Ateneo Parmense, 18(3), 93-101 and Bartholomew et al (1975) Journal of Organic Chemistry, 40(25), 3708-13.

7-Chloro-6H-imidazo[1,2-c]pyrimidin-5-one can be derivatised using nucleophilic substitution reactions such as $S_N$ Ar to add functionality at the 7 position (Scheme 17). The $S_N$ Ar reaction can be performed using potassium cyanide, and then converted to the amide. This compound can then be iodinated as described above before further functionalisation using the Suzuki reaction.

Scheme 17

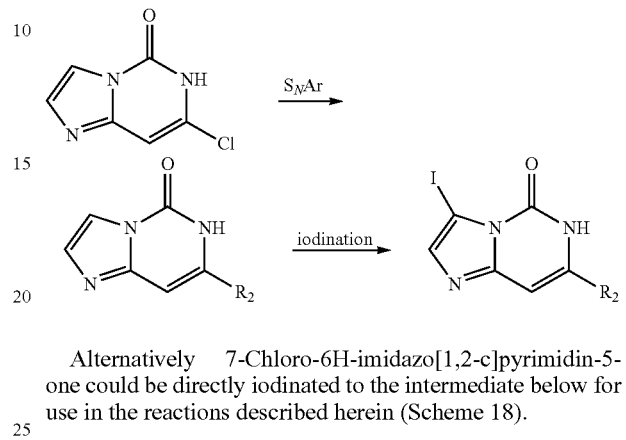

Alternatively 7-Chloro-6H-imidazo[1,2-c]pyrimidin-5-one could be directly iodinated to the intermediate below for use in the reactions described herein (Scheme 18).

Scheme 18

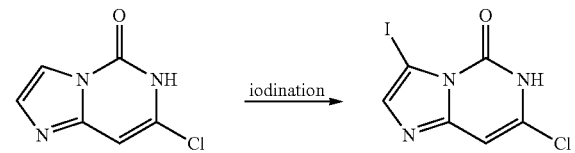

In addition, other oxo-heterocycles could be synthesized from the appropriate chloro derivative by hydrolysis. The protected compound would be subjected to base hydrolysis to afford the pyridone. This could be performed with NaOH (or NaOH/$H_2O_2$) in $H_2O$/MeOH or $H_2O$/dioxane following procedures described in the literature for the hydrolysis of chloropyridines (e.g. Australian J. Chem. (1984), 37(12), 2469-2477).

Imidazo[1,2-b]pyridazine

Scheme 19

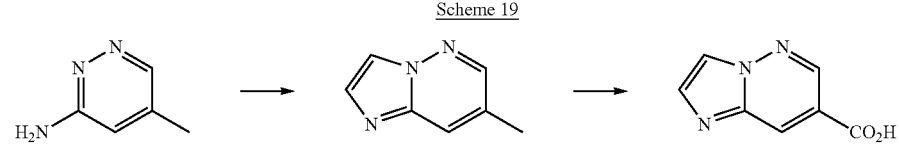

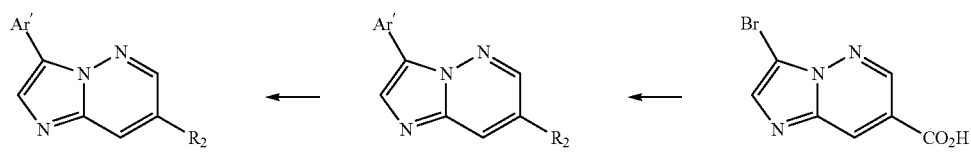

The synthesis of the Imidazo[1,2-b]pyridazine core can be performed as described in Scheme 19 using a pyridazin-3-ylamine derivative.

Many methyl, carboxylic acid, carboxylic ester, or halide substituted bicyclic or monocyclic aromatic compounds are commercially available. Therefore, these and other heterocycles, may be synthesised directly from the methyl, carboxylic acid, carboxylic ester, or halide substituted bicyclic compounds or from the methyl, carboxylic acid, carboxylic ester, or halide substituted monocyclic aromatic compounds using the cyclisation reactions described herein.

Other heterocycles can be synthesised using well known reactions, for example as described in Comprehensive Heterocyclic Chemistry I (Edited by Katritzky, A. R. and Rees, C. W. (1982) Elsevier) and Comprehensive Heterocyclic Chemistry II (Edited by Katritzky, A. R., Rees, C. W. and Scriven, E. F. V. (1996) Elsevier, ISBN 0-08-042072-9).

In many of the reactions described above, it may be necessary to protect one or more groups to prevent reaction from taking place at an undesirable location on the molecule. Examples of protecting groups, and methods of protecting and deprotecting functional groups, can be found in Protective Groups in Organic Synthesis (Green, T. and Wuts, P. (1999); 3rd Edition; John Wiley and Sons).

A hydroxy group may be protected, for example, as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc). An aldehyde or ketone group may be protected, for example, as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid. An amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), or as a 2(-phenylsulphonyl)ethyloxy amide (—NH-Psec). Other protecting groups for amines, such as cyclic amines and heterocyclic N—H groups, include toluenesulphonyl (tosyl) and methanesulphonyl (mesyl) groups and benzyl groups such as a para-methoxybenzyl (PMB) group. A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g., a benzyl ester; a nitrobenzyl ester); or as an amide, for example, as a methyl amide. A thiol group may be protected, for example, as a thioether (—SR), for example, as: a benzyl thioether; an acetamidomethyl ether (—S—CH$_2$NHC(=O)CH$_3$).

In one embodiment an intermediate can be a compound of formula (I) with a protecting groups attached e.g. benzyl, nosyl, tosyl, or fmoc (fluorenylmethyloxycarbonyl), in particular benzyl. The protecting group may be attached to or in place of one or more of R$^x$, R$^y$ or R$^z$.

Key intermediates in the preparation of the compounds of formula (I) are the compounds of formula (II) and (III) Novel chemical intermediates of the formula (II) and (III) and protected forms thereof form a further aspect of the invention.

A further aspect of the invention is a process for the preparation of a compound of formula (I) as defined herein, which process comprises:

(i) the reaction of a compound of the formula (II):

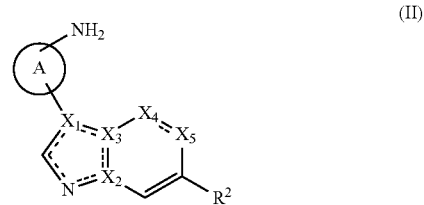

(II)

or a protected form thereof, with an appropriately substituted isocyanate or an appropriately substituted amine in the presence of carbonyl diimidazole (CDI); or (ii) the reaction of a compound of the formula (II):

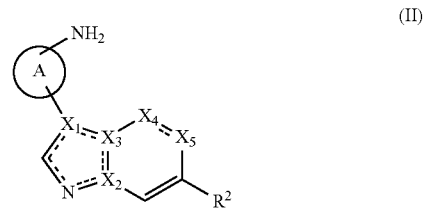

(II)

or a protected form thereof, with an appropriately substituted carboxylic acid or a reactive derivative; or (iii) the reaction of a compound of the formula (II):

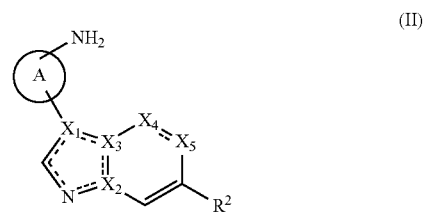

(II)

or a protected form thereof, with an appropriately substituted aldehyde or ketone; or (iv) the reaction of a compound of the formula (III):

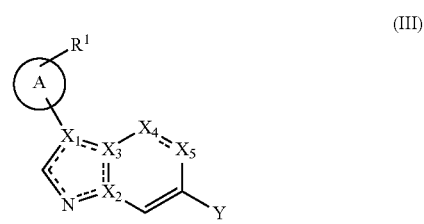

(III)

or a protected form thereof, wherein Y is a group which can be converted to an oxime of formula —CR$^v$=N—OR$^w$ e.g. ketone or aldehyde;

and then converting to an oxime of formula —CR$^v$=N—OR$^w$;

and thereafter removing any protecting group present;

wherein $X_{1-5}$, A, and $R^1$ are as defined herein; and optionally thereafter converting one compound of the formula (I) into another compound of the formula (I).

In a further embodiment the invention provides a novel intermediate of formula (IV):

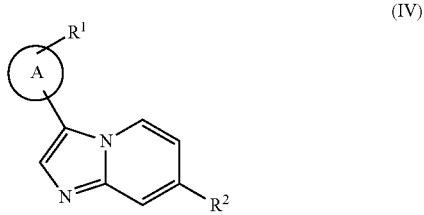

(IV)

wherein
A represents a phenyl group which may be optionally substituted by one $R^a$ groups wherein $R^a$ represents $C_{2-4}$alkyloxy, halo$C_{2-4}$alkyloxy, $C_{1-4}$alkoxy$C_{1-4}$alkyl, cyclobutoxy, cyclopropoxy, —NH—$C_{1-4}$ alkyl, —N($C_{1-4}$ alkyl)$_2$, —$C_{1-4}$ alkyl-NH($C_{1-4}$ alkyl), —$C_{1-4}$ alkyl-N($C_{1-4}$alkyl)$_2$, or —S(=O)$_2$—$C_{1-4}$alkyl. $R^1$ represents —NHCONR$^4$R$^5$;
$R^4$ represents hydrogen;
$R^5$ represents halo$C_{1-6}$alkyl;
$R^2$ represents a —COR$^g$ group or a CH=N—OR$^h$;
$R^h$ represents halo$C_{2-4}$ alkyl, —(CH$_2$)$_n$—COOR$^z$, —(CH$_2$)$_n$—NR$^x$R$^y$ or —Z'-heterocyclyl group wherein said heterocyclyl groups may be optionally substituted by one or more (e.g. 1, 2 or 3) of $C_{1-6}$alkyl or C(=O)—O—$C_{1-6}$ alkyl;
$R^z$ is hydrogen or $C_{1-6}$alkyl;
n is an integer from 1-4
$R^x$ is as defined for a compound of formula (I);
$R^y$ represents a —Y'-aryl and Y' represents (CH$_2$)$_n$;
Z' represents —(CH$_2$)$_n$;
when A is substituted by a —O—$C_{2-6}$ alkyl group, $R^g$ represents $C_{1-6}$ alkyl, $C_{3-8}$ cycloalkyl or —(CH$_2$)—$C_{3-8}$cycloalkyl;
when A is unsubstituted, $R^g$ represents $C_{2-6}$ alkyl or —(CH$_2$)—$C_{3-8}$cycloalkyl.

In one embodiment $R^2$ represents a —COR$^g$ group.
In one embodiment $R^a$ represents $C_{2-4}$ alkyloxy.
In one embodiment $R^x$ represents —(CH$_2$)$_n$—O—$C_{1-6}$alkyl.
In one embodiment when A is substituted by $C_{2-4}$alkyloxy, $R^g$ represents $C_{1-4}$ alkyl, $C_{3-6}$ cycloalkyl or —(CH$_2$)—$C_{3-6}$cycloalkyl. In another embodiment when A is unsubstituted; $R^g$ represents $C_{2-4}$ alkyl or —(CH$_2$)—$C_{3-6}$cycloalkyl.

In one embodiment the novel intermediate is selected from:
1-[3-(7-Propionyl-imidazo[1,2-a]pyridin-3-yl)-phenyl]-3-(2,2,2-trifluoro-ethyl)-urea;
1-{3-[7-(2-Cyclopropyl-acetyl)-imidazo[1,2-a]pyridin-3-yl]-phenyl}-3-(2,2,2-trifluoro-ethyl)-urea;
and
1-[3-(7-Cyclopropanecarbonyl-imidazo[1,2-a]pyridin-3-yl)-5-isopropoxy-phenyl]-3-(2,2,2-trifluoro-ethyl)-urea.

In one embodiment $R^2$ represents a CH=N—OR$^h$ wherein $R^h$ represents halo$C_{2-4}$alkyl, —(CH$_2$)$_n$—COOR$^z$, or —Z-heterocyclyl group wherein said heterocyclyl groups may be optionally substituted by one or more (e.g. 1, 2 or 3) of $C_{1-6}$alkyl or C(=O)—O—$C_{1-6}$alkyl and wherein Z represents —(CH$_2$)$_n$—, wherein $R^z$ is hydrogen or $C_{1-6}$alkyl and n is 1-4, or —(CH$_2$)$_n$—NR$^x$R$^y$, wherein $R^x$ represents —(CH$_2$)$_n$—O—$C_{1-6}$alkyl and $R^y$ represents a —Y-carbocyclyl and Y represents —(CH$_2$)$_n$.

In one embodiment the novel intermediate is:
1-(3-{7-[(3-Chloro-propoxyimino)-methyl]-imidazo[1,2-a]pyridin-3-yl}-phenyl)-3-(2,2,2-trifluoro-ethyl)-urea.

Pharmaceutically Acceptable Salts, Solvates or Derivatives Thereof.

In this section, as in all other sections of this application, unless the context indicates otherwise, references to formula (I) include references to all other sub-groups, preferences and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. In one embodiment, references to compounds of the formula (I) includes compounds of the formula (I) or pharmaceutically acceptable salt or solvate thereof.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

The compounds of the invention may exist as mono- or di-salts depending upon the pKa of the acid from which the salt is formed.

If the compound is anionic, or has a functional group which may be anionic (e.g., —COOH may be —COO—), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds on the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR(SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation using crystallisation conditions that include an amount of the solvent required for the particular solvate. Thereafter the standard methods described above, can be used to establish whether solvates had formed.

Furthermore, the compounds of the present invention may have one or more polymorph, amorphous or crystalline forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

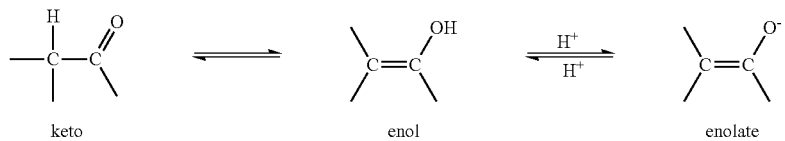

keto      enol      enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Where compounds of the formula (I) contain one or more double bonds, and can exist in the form of two geometric isomers, references to compounds of the formula (I) include both stereoisomeric forms thereof (i.e. cis-trans isomerism or (E) and (Z) isomerism), either as individual isomers, or mixtures of two isomers, unless the context requires otherwise.

The term "geometric isomer" means isomers that differ in the orientation of substituent atoms in relationship to a carbon-carbon double bond, to a carbon-nitrogen double bond, to a cycloalkyl ring, or to a bridged bicyclic system. Substituent atoms (other than hydrogen) on each side of a carbon-carbon or carbon-nitrogen double bond may be in an E or Z configuration. Whether a molecular configuration is designated E or Z is determined by the Cahn-Ingold-Prelog priority rules (higher atomic numbers are given higher priority). For each of the two atoms in the double bond, it is necessary to determine which of the two substituents is of a higher priority. In the "E" configuration, both of the substituents of higher priority are on opposite sides in relationship to the carbon-nitrogen double bond. In the "Z" configuration, both of the substituents of higher priority are on the same side in relationship to the carbon-nitrogen double bond.

As illustrated by crossed double bond between the carbon and nitrogen atom for certain compounds of the present invention is intended to represent that the orientation of the O—R$^w$ substituent atoms in relationship to the carbon-nitrogen double bond are not designated either E or Z. Accordingly, structures including a cross double bond indicate the compound has been prepared as a mixture of isomers. Where a compound is drawn or indicated as a specific isomer, the alternative isomer and mixtures of the isomers are also within the scope of the application.

The isomeric descriptors ("R," "S," "E," and "Z") indicate atom configurations and are intended to be used as defined in the literature.

Aldoximes, except for aromatic aldoximes, normally exist only as the E isomer, while ketoximes can be separated almost completely and obtained as a E and Z isomer.

Synthetic processes can result in a mixture of geometric isomers and then chirally stable isomers can be separated by a number of techniques including chromatography and such techniques well known to the person skilled in the art. Some of the oximes are not chirally stable and thus cannot be separated. Alternatively various synthetic processes can be used to influence whether the E or Z geometric isomer was produced.

In cases where the compounds of the invention exist as the E and Z isomers, the invention includes individual isomers as well as mixtures thereof. Where compounds of the formula (I) exist as two or more stereoisomeric forms, one stereoisomer in a pair may exhibit advantages over the other, for example, in terms of biological activity. Thus, in certain circumstances, it may be desirable to use as a therapeutic agent only one of a pair of stereoisomers. Accordingly, the invention provides compositions containing a compound of the formula (I) having one or more double bonds, wherein at least 55% (e.g. at least 60%, 65%, 70%, 75%, 80%, 85%, 90% or 95%) of the compound of the formula (I) is present as a single isomer (e.g. (E) or (Z) isomer). In one general embodiment, 99% or more (e.g. substantially all) of the total amount of the compound of the formula (I) may be present as a single stereoisomer. The compounds of the invention include compounds with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and prodrugs of the compounds. By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$ alkyl (e.g., -Me, -Et, -nPr, -iPr, -nBu, -sBu, -iBu, -tBu);
$C_{1-7}$-aminoalkyl (e.g., aminoethyl; 2-(N,N-diethylamino) ethyl; 2-(4-morpholino)ethyl); and
acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof.

According to a further aspect of the invention there is provided a compound as defined herein or a salt or solvate thereof.

References to compounds of the formula (I), (Ia), (Ib), (Ic) and (Id) and sub-groups thereof as defined herein include within their scope the salts or solvates or tautomers or N-oxides of the compounds.

Protein Tyrosine Kinases (PTK)

The compounds of the invention described herein inhibit or modulate the activity of certain tyrosine kinases, and thus the compounds will be useful in the treatment or prophylaxis of disease states or conditions mediated by those tyrosine kinases in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state (Powers, et al. (2000) Endocr. Relat. Cancer, 7, 165-197).

FGFs and their receptors are expressed at increased levels in several tissues and cell lines and overexpression is believed to contribute to the malignant phenotype.

Furthermore, a number of oncogenes are homologues of genes encoding growth factor receptors, and there is a potential for aberrant activation of FGF-dependent signalling in human pancreatic cancer (Ozawa, et al. (2001), Teratog. Carcinog. Mutagen., 21, 27-44).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Upon ligand binding, the receptors dimerize and auto- or transphosphorylate specific cytoplasmic tyrosine residues to transmit an intracellular signal that ultimately regulates nuclear transcription factor effectors.

Disruption of the FGFR1 pathway should affect tumor cell proliferation since this kinase is activated in many tumor types in addition to proliferating endothelial cells. The overexpression and activation of FGFR1 in tumor-associated vasculature has suggested a role for these molecules in tumor angiogenesis.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2 (Lemonnier, et al. (2001), J. Bone Miner. Res., 16, 832-845). In addition, mutation screening in patients with syndromic craniosynostoses indicates that a number of recurrent FGFR2 mutations accounts for severe forms of Pfeiffer syndrome (Lajeunie et al, *European Journal of Human Genetics* (2006) 14, 289-298). Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene (Meyers, et al. (1996) Am. J. Hum. Genet., 58, 491-498; Plomp, et al. (1998) Am. J. Med. Genet., 75, 245-251), and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2 (Yu, et al. (2000), Proc. Natl. Acad. Sci. U.S.A., 97, 14536-14541).

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas (Powers, C. J. (2000), et al., Endocr. Rel. Cancer, 7, 165; Qiu, W. et. al. (2005), World Journal Gastroenterol, 11(34)). Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC) (Journal of Pathology (2007), 213 (1), 91-98). Increased expression was associated with mutation (85% of mutant tumors showed high-level expression) but also 42% of tumors with no detectable mutation showed over-expression, including many muscle-invasive tumors.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Over expression of FGFR4 has been linked to poor prognosis in both prostate and thyroid carcinomas (Ezzat, S., et al. (2002) The Journal of Clinical Investigation, 109, 1; Wang et al. (2004) Clinical Cancer Research, 10). In addition a germline polymorphism (Gly388Arg) is associated with increased incidence of lung, breast, colon and prostate cancers (Wang et al. (2004) Clinical Cancer Research, 10). In addition, a truncated form of FGFR4 (including the kinase domain) has also been found to present in 40% of pituitary tumours but not present in normal tissue. FGFR4 overexpression has been observed in liver, colon and lung tumours (Desnoyers et al. (2008) Oncogene, 27; Ho et al. (2009) Journal of Hepatology, 50). These studies described targeting of either FGFR4 kinase activity or its ligand FGF 19 with an antibody antagonist inhibited proliferation and induced apoptosis in cell line models. Ho et al showed that one third of patients with a common polymorphism in the FGFR4 gene expressed high levels of mRNA and these tumours were associated with high secreted levels of the hepatocellular carcinoma marker alpha-fetoprotein.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006) Clin Cancer Res. 12(22): 6652-6662.

Rhabdomyosarcoma (RMS), the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes (Genes, Chromosomes & Cancer (2007), 46(11), 1028-1038).

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGF3) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis (Inoue, et al. (1997 & 2002); Barrios, et al. (1997)). TGFβ1 and PDGF have been reported to be involved in the fibrogenic process (reviewed by Atamas & White, 2003) and further published work suggests the elevation of FGF's and consequent increase in fibroblast proliferation, may be in response to elevated TGFβ1 (Khalil, et al., 2005). The potential therapeutic relevance of this pathway in fibrotic conditions is suggested by the reported clinical effect of Pirfenidone (Arata, et al., 2005) in idiopathic pulmonary fibrosis (IPF).

Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels. (Folkman (1997), 79, 1-81; Folkman (1995), *Nature Medicine*, 1, 27-31; Folkman and Shing (1992) J. Biol. Chem., 267, 10931).

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott (1992), *Ann. Rhum. Dis.*, 51, 919). In diabetes (and in many different eye diseases), new vessels invade the macula or retina or other ocular structures, and may cause blindness (Brooks, et al. (1994) *Cell*, 79, 1157). The process of atherosclerosis has been linked to angiogenesis (Kahlon, et al. (1992) *Can. J. Cardiol.*, 8, 60). Tumor growth and metastasis have been found to be angiogenesis-dependent (Folkman (1992), *Cancer Biol*, 3, 65; Denekamp, (1993) *Br. J. Rad.*, 66, 181; Fidler and Ellis (1994), *Cell*, 79, 185).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly, et al. (1994) Cell, 79, 315; Ingber, et al. (1990) Nature, 348, 555), ocular diseases (Friedlander, et al. (1995) Science, 270, 1500), arthritis (Peacock, et al. (1992), J. Exp. Med., 175, 1135; Peacock et al. (1995), Cell. Immun., 160, 178) and hemangioma (Taraboletti, et al. (1995) J. Natl. Cancer Inst., 87, 293).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified.

Vascular endothelial growth factor (VEGF), a polypeptide, is mitogenic for endothelial cells in vitro and stimulates angiogenic responses in vivo. VEGF has also been linked to inappropriate angiogenesis (Pinedo, H. M., et al. (2000), The Oncologist, 5(90001), 1-2). VEGFR(s) are protein tyrosine kinases (PTKs). PTKs catalyze the phosphorylation of specific tyrosine residues in proteins involved in cell function thus regulating cell growth, survival and differentiation. (Wilks, A. F. (1990), Progress in Growth Factor Research, 2, 97-111; Courtneidge, S. A. (1993) Dev. Supp.l, 57-64; Cooper, J. A. (1994), Semin. Cell Biol., 5(6), 377-387; Paulson, R. F. (1995), Semin. Immunol., 7(4), 267-277; Chan, A. C. (1996), Curr. Opin. Immunol., 8(3), 394-401). Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction (Mustonen, T. (1995), et al., J. Cell Biol., 129, 895-898).

Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis (McMahon, G. (2000), The Oncologist, 5(90001), 3-10).

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-I), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition. Inhibition of VEGFR2 but not VEGFR1 markedly disrupted angiogenic switching, persistent angiogenesis, and initial tumor growth. In late-stage tumours, phenotypic resistance to VEGFR2 blockade emerged, as tumours regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

A FGF-trap adenovirus has been previously reported to bind and block various ligands of the FGF family, including FGF1, FGF3, FGF7, and FGF10, thereby effectively inhibiting angiogenesis in vitro and in vivo. Indeed, adding the FGF-trap treatment in the regrowth phase of a mouse model produced a significant decrease in tumor growth compared to anti-VEGFR2 alone. This decrease in tumor burden was accompanied by a decrease in angiogenesis that was observed as decreased intratumoral vessel density.

Batchelor et al. (Batchelor et al., 2007, *Cancer Cell*, 11(1), 83-95) provide evidence for normalization of glioblastoma blood vessels in patients treated with a pan-VEGF receptor tyrosine kinase inhibitor, AZD2171, in a phase 2 study. The rationale for using AZD2171 was based partially on results showing a decrease in perfusion and vessel density in an in vivo breast cancer model (Miller et al., 2006, *Clin. Cancer Res.* 12, 281-288). Furthermore, using an orthotopic glioma model, it had previously been identified that the optimal window of time to deliver anti-VEGFR2 antibody to achieve a synergistic effect with radiation. During the window of normalization, there was improved oxygenation, increased pericyte coverage, and upregulation of angiopoietin-1 leading to a decrease in interstitial pressure and permeability within the tumour (Winkler et al., 2004, *Cancer Cell* 6, 553-563). The window of normalization can be quantified using magnetic resonance imaging (MRI) using MRI gradient echo, spin echo, and contrast enhancement to measure blood volume, relative vessel size, and vascular permeability.

The authors showed that progression on treatment with AZD2171 was associated with an increase in CECs, SDF1, and FGF2, while progression after drug interruptions correlated with increases in circulating progenitor cells (CPCs) and plasma FGF2 levels. The increase in plasma levels of SDF1 and FGF2 correlated with MRI measurements, demonstrated an increase in the relative vessel density and size. Thus, MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation. PDGF expression has been demonstrated in a number of different solid tumours including glioblastomas and prostate carcinomas. The tyrosine kinase inhibitor imatinib mesylate, which has the chemical name 4-[(4-methyl-1-piperazinyl)methyl]-N-[4-methyl-3-[[4-(3-pyridinyl)-2-ylpyridinyl]amino]-phenyl]benzamide methanesulfonate, blocks activity of the Bcr-Abl oncoprotein and the cell surface tyrosine kinase receptor c-Kit, and as such is approved for the treatment of chronic myeloid leukemia and gastrointestinal stromal tumours. Imatinib mesylate is also a potent inhibitor of PDGFR kinase and is currently being evaluated for the treatment of chronic myelomonocytic leukemia and glioblastoma multiforme, based upon evidence in these diseases of activating mutations in PDGFR. In addition, sorafenib (BAY 43-9006) which has the chemical name 4-(4-(3-(4-chloro-3 (trifluoromethyl)phenyl)ureido)phenoxy)-N2-methylpyridine-2-carboxamide, targets both the Raf signalling pathway to inhibit cell proliferation and the VEGFR/PDGFR signalling cascades to inhibit tumour angiogenesis. Sorafenib is being investigated for the treatment of a number of cancers including liver and kidney cancer.

There are conditions which are dependent on activation of PDGFR such as hypereosinophilic syndrome. PDGFR activation is also associated with other malignancies, which include chronic myelomonocytic leukemia (CMML). In another disorder, dermatofibrosarcoma protuberans, an infiltrative skin tumor, a reciprocal translocation involving the gene encoding the PDGF-B ligand results in constitutive secretion of the chimeric ligand and receptor activation. Imatinib has which is a known inhibitor of PDGFR has activity against all three of these diseases.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, it is envisaged that the compounds of the invention will be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3.

Preferred compounds are compounds that inhibit one or more FGFR selected from FGFR1, FGFR2 and FGFR3, and also FGFR4. Preferred compounds of the invention are those having $IC_{50}$ values of less than 0.1 µM.

Compounds of the invention also have activity against VEGFR.

Compounds of the invention also have activity against PDGFR kinases. In particular, the compounds are inhibitors of PDGFR and, for example, inhibit PDGFR A and/or PDGFR B.

In addition many of the compounds of the invention exhibit selectivity for the FGFR 1, 2, and/or 3 kinase, and/or FGFR4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or FGFR4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, VEGFR and/or PDGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukemia, acute lymphocytic leukemia, chronic lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, myeloproliferative syndrome, myelodysplastic syndrome, or promyelocytic leukemia; multiple myeloma; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis.

Thus, in the pharmaceutical compositions, uses or methods of this invention for treating a disease or condition comprising abnormal cell growth, the disease or condition comprising abnormal cell growth in one embodiment is a cancer.

Further T-cell lymphoproliferative diseases include those derived from natural Killer cells. The term B-cell lymphoma includes diffuse large B-cell lymphoma.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

A further example of a tumour of mesenchymal origin is Ewing's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

It is further envisaged that the compound of the invention having FGFR such as FGFR1 inhibitory activity, will be particularly useful in the treatment or prevention of breast cancer in particular Classic Lobular Carcinomas (CLC).

As the compounds of the invention have FGFR4 activity they will also be useful in the treatment of prostate or pituitary cancers.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are in the treatment of multiple myeloma (in particular multiple myeloma with t(4;14) translocation or overexpressing FGFR3), prostate cancer (hormone refractory prostate carcinomas), endometrial cancer (in particular endometrial tumours with activating mutations in FGFR2) and breast cancer (in particular lobular breast cancer).

In particular the compounds are useful for the treatment of lobular carcinomas such as CLC(Classic lobular carcinoma).

As the compounds have activity against FGFR3 they will be useful in the treatment of multiple myeloma and bladder.

In particular the compounds are useful for the treatment of t(4;14) translocation positive multiple myeloma.

As the compounds have activity against FGFR2 they will be useful in the treatment of endometrial, ovarian, gastric and colorectal cancers. FGFR2 is also overexpressed in epithelial ovarian cancer, therefore the compounds of the invention may be specifically useful in treating ovarian cancer such as epithelial ovarian cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR, VEGFR or PDGFR signalling may be determined by means of a cell growth assay as set out below or by a method as set out in the section headed "Methods of Diagnosis".

It is further envisaged that the compounds of the invention, and in particular those compounds having FGFR, VEGFR or PDGFR inhibitory activity, will be particularly useful in the treatment or prevention of cancers of a type associated with or characterised by the presence of elevated levels of FGFR, VEGFR or PDGFR, for example the cancers referred to in this context in the introductory section of this application.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

It is also envisaged that the compounds of the invention will be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions where it is envisaged that the compounds of the invention will be useful consists of inflammatory diseases, cardiovascular diseases and wound healing.

FGFR, VEGFR and PDGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

It is further envisaged that the compound of the invention having FGFR such as FGFR2 or FGFR3 inhibitory activity, will be particularly useful in the treatment or prevention of the skeletal diseases. Particular skeletal diseases are achondroplasia or thanatophoric dwarfism (also known as thanatophoric dysplasia).

It is further envisaged that the compound of the invention having FGFR such as FGFR1, FGFR2 or FGFR3 inhibitory activity, will be particularly useful in the treatment or prevention in pathologies in which progressive fibrosis is a symptom. Fibrotic conditions in which the compounds of the inventions may be useful in the treatment of in include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

Since compounds of the invention inhibit PDGFR they may also be useful in the treatment of a number of tumour and leukemia types including glioblastomas such as glioblastoma multiforme, prostate carcinomas, gastrointestinal stromal tumours, liver cancer, kidney cancer, chronic myeloid leukemia, chronic myelomonocytic leukemia (CMML) as well as hypereosinophilic syndrome, a rare proliferative hematological disorder and dermatofibrosarcoma protuberans, an infiltrative skin tumour.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

The invention provides compounds that have FGFR inhibiting or modulating activity, and which it is envisaged will be useful in preventing or treating disease states or conditions mediated by FGFR kinases.

In one embodiment, there is provided a compound as defined herein for use in therapy. In a further embodiment, there is provided a compound as defined herein for use in the prophylaxis or treatment of a disease state or condition mediated by a FGFR kinase.

Thus, for example, it is envisaged that the compounds of the invention will be useful in alleviating or reducing the incidence of cancer. Therefore, in a further embodiment, there is provided a compound as defined herein for use in the prophylaxis or treatment of cancer.

Accordingly, in one aspect, the invention provides the use of a compound for the manufacture of a medicament for the prophylaxis or treatment of a disease state or condition mediated by a FGFR kinase, the compound having the formula (I) as defined herein.

In one embodiment, there is provided the use of a compound as defined herein for the manufacture of a medicament for the prophylaxis or treatment of a disease state or condition as described herein.

In a further embodiment, there is provided the use of a compound as defined herein for the manufacture of a medicament for the prophylaxis or treatment of cancer.

Accordingly, the invention provides inter alia:

A method for the prophylaxis or treatment of a disease state or condition mediated by a FGFR kinase, which method comprises administering to a subject in need thereof a compound of the formula (I) as defined herein.

In one embodiment, there is provided a method for the prophylaxis or treatment of a disease state or condition as described herein, which method comprises administering to a subject in need thereof a compound of the formula (I) as defined herein.

In a further embodiment, there is provided a method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use as a modulator (e.g. inhibitor) of FGFR.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme (Carter et al (2005), PNAS, 102(31), 11011-110116).

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group (Jang et. al. (2001) Cancer Research 61 3541-3543.

There are mutations that have been observed in PDGFR in imatinib-treated patients, in particular the T674I mutation. The clinical importance of these mutations may grow considerably, as to date it appears to represent the primary mechanism of resistance to src/Abl inhibitors in patients.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR or PDGFR including PDGFR-beta and PDGFR-alpha in particular the T674I mutation of PDGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1V561M showed that this mutation conferred resistance to a tyrosine kinase inhibitor compared to that of the wild type.

Advantages of the Compositions of the Invention

The compounds of the formula (I) have a number of advantages over prior art compounds.

For example compounds may have increased potency for FGFR3 and increased selectivity over VEGFR2.

For example, the compounds of formula (I) have advantageous ADMET and physiochemical properties over prior art compounds. In particular compounds may have good solubility.

Pharmaceutical Formulations

While it is possible for the active compound to be administered alone, it is preferable to present it as a pharmaceutical composition (e.g. formulation) comprising at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

Accordingly, in a further aspect, the invention provides compounds of the formula (I) and sub-groups thereof as defined herein in the form of pharmaceutical compositions. The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly (2004), Solubilizing Excipients in oral and injectable formulations, Pharmaceutical Research, Vol 21(2), p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman (1971), J. Pharm. Sci., 60, 1281-1300) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

The skilled person will have the expertise to select the appropriate amounts of ingredients for use in the formulations. For example tablets and capsules typically contain 0-20% disintegrants, 0-5% lubricants, 0-5% flow aids and/or 0-100% fillers/or bulking agents (depending on drug dose). They may also contain 0-10% polymer binders, 0-5% antioxidants, 0-5% Pigments. Slow release tablets would in addition contain 0-100% polymers (depending on dose). The film coats of the tablet or capsule typically contain 0-10% polymers, 0-3% pigments, and/or 0-2% plasticizers.

Parenteral formulations typically contain 0-20% buffers, 0-50% cosolvents, and/or 0-100% Water for Injection (WFI) (depending on dose and if freeze dried). Formulations for intramuscular depots may also contain 0-100% oils.

Examples of Pharmaceutical Formulations (i) Tablet Formulation

A tablet composition containing a compound of the formula (I) is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (I) with 100 mg lactose and filling the resulting mixture into standard opaque hard gelatin capsules.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (I) with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

Methods of Treatment

It is envisaged that the compounds of the formula (I) and sub-groups thereof as defined herein will be useful in the prophylaxis or treatment of a range of disease states or conditions mediated by FGFR. Examples of such disease states and conditions are set out above.

The compounds are generally administered to a subject in need of such administration, for example a human or animal patient, preferably a human. The compounds will typically be administered in amounts that are therapeutically or prophylactically useful and which generally are non-toxic.

However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compounds as defined herein can be administered as the sole therapeutic agent or they can be administered in combination therapy with one of more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and, Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethazone, prednisone, and prednisolone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromoembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). The compounds of the invention may also be administered in conjunction with non-chemotherapeutic treatments such as radiotherapy, photodynamic therapy, gene therapy; surgery and controlled diets.

For use in combination therapy with another chemotherapeutic agent, the compound of the formula (I) and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a compound of the formula (I), a patient may be screened to determine whether a disease or condition from which the patient is or may be suffering is one which would be susceptible to treatment with a compound having activity against FGFR, VEGFR and/or PDGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, VEGFR and/or PDGFR or to sensitisation of a pathway to normal FGFR, VEGFR and/or PDGFR activity, or to upregulation of these growth factor signalling pathways such as growth factor ligand levels or growth factor ligand activity or to upregulation of a biochemical pathway downstream of FGFR, VEGFR and/or PDGFR activation.

Examples of such abnormalities that result in activation or sensitisation of the FGFR, VEGFR and/or PDGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions (Lemonnier, et al. (2001), J. Bone Miner. Res., 16, 832-845). In particular activating mutations in FGFR2 have been identified in 10% of endometrial tumours (Pollock et al, Oncogene, 2007, 26, 7158-7162).

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas (Powers, C. J., et al. (2000), Endocr. Rel. Cancer, 7, 165). A particular mutation T674I of the PDGF receptor has been identified in imatinib-treated patients.

In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway (Reis-Filho et al. (2006), Clin Cancer Res. 12(22), 6652-6662).

Alternatively, a biological sample taken from a patient may be analysed for loss of a negative regulator or suppressor of FGFR, VEGFR or PDGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, VEGFR and/or PDGFR. The term diagnosis includes screening. By marker we include genetic markers including, for example, the measurement of DNA composition to identify mutations of FGFR, VEGFR and/or PDGFR. The term marker also includes markers which are characteristic of up regulation of FGFR, VEGFR and/or PDGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, VEGFR and/or PDGFR may mean that the patient would be particularly suitable for treatment with a FGFR, VEGFR and/or PDGFR inhibitor. Tumours may preferentially be screened for presence of a FGFR, VEGFR and/or PDGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, VEGFR and/or PDGFR, or detection of FGFR, VEGFR and/or PDGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105 (Mineo et al. (2004) J Clin Pathol. 57(6), 591-7).

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung and breast cancer.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, $K_{652}Q$ mutations in FGFR3 and Gly388Arg polymorphism in FGFR4.

In another aspect of the inventions includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

General Synthetic Routes

The following examples illustrate the present invention but are examples only and are not intended to limit the scope of the claims in any way.

Hereinafter, "DCM" is defined as dichloromethane, "DIPE" is defined as diisopropyl ether, "DMA" is defined as dimethylacetamide, "DMF" is defined as N,N-dimethylformamide, 'DMSO' is defined as dimethylsulfoxide, "MeOH" is defined as methanol and "THF" is defined as tetrahydrofuran.

Preparation of the Compounds

EXAMPLE1.1.a 1.1.a(1) Preparation of Intermediate

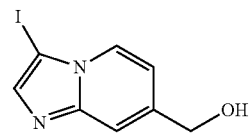 [SMILES: OCc1ccn2c(I)cnc2c1]

A solution of imidazo[1,2-a]pyridine-7-methanol [342613-80-3] (2.025 mmol) in DMF (5 ml) was stirred at 0° C. under $N_2$-flow. A solution of N-iodosuccinimide (2.126 mmol) in DMF (1 ml) was added dropwise at 0° C. and after addition, the reaction mixture was stirred for 1 hour. The mixture was allowed to reach ambient temperature and stirring was continued for 2 hours. The solution was treated with water and the product was extracted with DCM. The organic layer was washed with water, 20% sodium thiosulfate, water and brine. The organic layer was dried (MgSO$_4$), filtered and evaporated to dryness. The crude residue was purified by flash column chromatography (eluent: DCM-DCM/MeOH 95/5). The desired fractions were collected and evaporated to dryness, yielding 390 mg of the intermediate shown.

1.1.a(2) Preparation of Intermediate

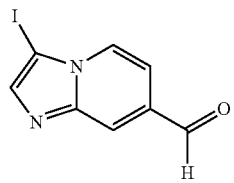 [SMILES: O=Cc1ccn2c(I)cnc2c1]

To a suspension of intermediate of example 1.1.a(1) above (1.387 mmol) in DCM (15 ml) was added portion wise manganese oxide (4.16 mmol). Extra manganese oxide (1 equivalent, 121 mg) was added and the reaction was left for 48 hours. The mixture was filtered over celite and washed with DCM. The solvent was evaporated under reduced pressure, yielding 320 mg of the intermediate shown.

1.1.a(3) Preparation of Intermediate

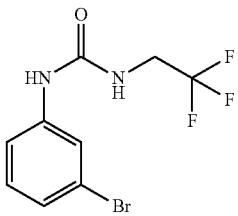 [SMILES: O=C(NCC(F)(F)F)Nc1cccc(Br)c1]

3-Bromophenyl isocyanate (0.112 mol) was added dropwise at 5° C. to a solution of 2,2,2-trifluoroethylamine (0.167 mmol) in THF (120 ml) over a 15 minutes periode. The mixture was stirred at 5° C. for 1 hour and then at room temperature for 4 hours. The mixture was evaporated to dryness and the crude product was used without further purification in the next step, yielding 33.1 g of the intermediate shown.

1.1.a(4) Preparation of Intermediate

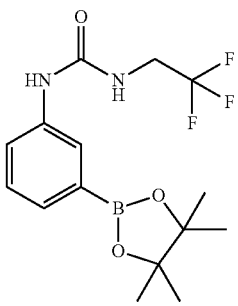 [SMILES: CC1(C)OB(c2cccc(NC(=O)NCC(F)(F)F)c2)OC1(C)C]

Intermediate of example 1.1.a(3) (16.831 mmol), Bis(pinacolato)diboron (18.514 mmol), and potassium acetate (50.492 mmol) were dissolved in DMSO (15 ml) and nitrogen was bubbled in the stirring mixture.

Dichloro(diphenylphosphinoferrocene)palladium [72287-26-4](0.505 mmol) was added and the nitrogen bubbling was continued for 10 minutes. The reaction mixture was heated at 100° C. overnight. The reaction was diluted with ethyl acetate/water. The aqueous phase was again washed with ethyl acetate. The combined organic phases were washed with water, brine, dried with sodium sulfate, filtered and concentrated under reduced pressure. The residue was triturated with a minimum of DCM and n-heptane with vigorous stirring. The precipitate was filtered and washed with n-heptane, yielding 5.07 g of intermediate shown.

1.1.a(5) Preparation of Intermediate

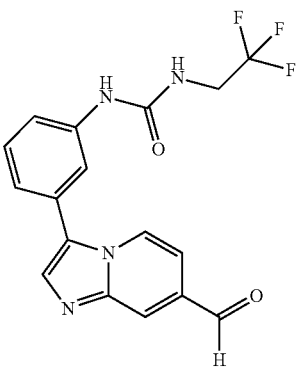 [SMILES: O=Cc1ccn2c(-c3cccc(NC(=O)NCC(F)(F)F)c3)cnc2c1]

Intermediate of example 1.1.a(2) (10.921 mmol) and intermediate of example 1.1.a(4) (13.105 mmol) in dioxane (60 ml) were charged in a round bottom flask. Nitrogen was bubbled in the reaction mixture under stirring. Phosphoric acid, potassium salt (1:3) (21.842 mmol) in water (15 ml) was added followed by dichloro(diphenylphosphinoferrocene) palladium [72287-26-4](0.546 mmol) and the stirring under bubbling nitrogen was continued for 10 minutes. The reaction mixture was heated to 80° C. overnight. The reaction was cooled to room temperature, diluted with water and extracted with ethyl acetate. The combined organic phases were washed with brine, dried over sodium sulfate, filtered and concentrated under reduced pressure. The residu was precipitated in DCM/n-heptane, filtered, washed with DCM/n-heptane and dried at 50° C. under reduced pressure, yielding 4.168 g of intermediate shown.

1.1.a(6) Preparation of Intermediate

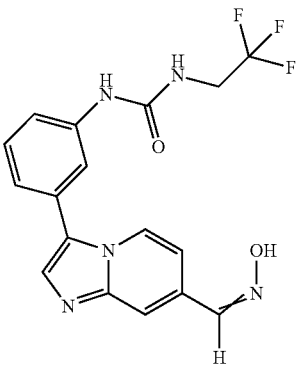 [SMILES: O=C(NCC(F)(F)F)Nc1cccc(-c2cnc3cc(C=NO)ccn23)c1]

To a stirring suspension of intermediate of example 1.1.a (5) (11.399 mmol) in ethanol (80 ml) and pyridine (20 ml) was added hydroxylamine, hydrochloride (1:1) (22.798 mmol). The solution was poured in water (1 L) and the precipitate was filtered, washed with water and dried at 50° C. under reduced pressure. The residue was stirred in diethyl ether for 10 minutes and filtered. The precipitate was heated in methanol and slowly added to a stirring solution of diethyl ether. The newly formed precipitate was filtered and dried at 50° C. under reduced pressure, yielding 2.79 g of intermediate shown.

1.1.a(7) Preparation of Final Compound

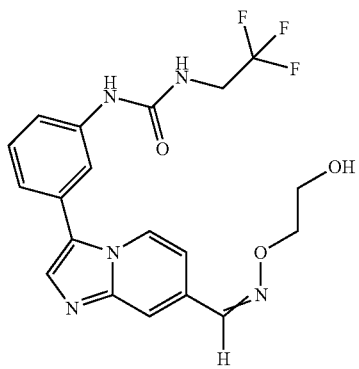 [SMILES: O=C(NCC(F)(F)F)Nc1cccc(-c2cnc3cc(C=NOCCO)ccn23)c1]

Intermediate of example 1.1.a(6) (1.325 mmol), 2-bromoethanol (7.951 mmol), and cesium carbonate (6.626 mmol) in DMSO (15 ml) were placed in a sealed tube and stirred at room temperature for 20 hours. The solution was poured into water and extracted 2 times with ethyl acetate. The combined organic phases were dried over $MgSO_4$, filtered and evaporated under reduced pressure. The crude residual fraction was purified by high-performance liquid chromatography (RP-18) (eluent:(0.25% $NH_4HCO_3$ in $H_2O$)/$CH_3CN$ 90/10-0/100 v/v). The desired fractions were collected and evaporated to dryness. The product was repurified by high-performance liquid chromatography (RP-18) (eluent:(0.25% $NH_4HCO_3$ in $H_2O$)/MeOH 30/70 v/v). The product was coevaporated with toluene and the residual fraction was dried under vacuo at 50° C., yielding 46 mg of compound shown.

EXAMPLE1.1.b

Preparation of Compound

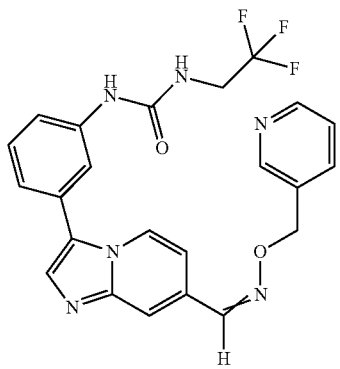 [SMILES: O=C(NCC(F)(F)F)Nc1cccc(-c2cnc3cc(C=NOCc4cccnc4)ccn23)c1]

To a mixture of intermediate of example 1.1.a(6) (1.06 mmol) and 3-pyridinemethanol, 3-methanesulfonate (1.166 mmol) in DMSO (10 ml) was added cesium carbonate (4.24 mmol). The reaction mixture was stirred at room temperature for 1 hour. The reaction mixture was dropped into distilled water. The slurry was filtered and washed with distilled water. The residue was purified by reverse-phase chromatography using a Hyperprep C18 HS BDS 100 Å 8 μm (Shandon) column (50 mm diameter, 16.5 cm length) and acetonitrile-water mixture as eluent. The desired fractions were collected, yielding 259 mg of compound shown.

EXAMPLE1.2

1.2(1) Preparation of Intermediate

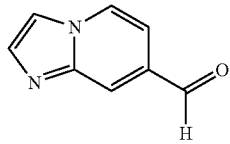 [SMILES: O=Cc1ccn2ccnc2c1]

To a suspension of imidazo[1,2-a]pyridine-7-methanol (409.815 mmol) in DCM (2 L) was added manganese oxide (819.631 mmol) under vigourous stirring. After 2 hours 2 more eq of manganese oxide (71.3 g) were added and the reaction was left overnight. 1 more eq of manganese oxide (36 g) was added and the reaction was left for 4 hours. The reaction was stopped. The reaction mixture was filtered over dicalite and the filtrate was evaporated under reduced pressure at 40° C. and dried in vacuo at 50° C. overnight, yielding 45 g of intermediate shown.

1.2(2) Preparation of Intermediate

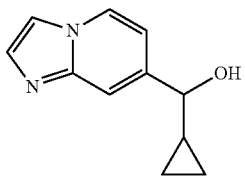 [SMILES: OC(c1ccn2ccnc2c1)C1CC1]

To a solution of intermediate of example 1.2(1). (27.369 mmol) in THF dry (120 ml) was added at 0° C. cyclopropylmagnesium bromide in THF 0.5 M (41.053 mmol) under nitrogen atmosphere. The reaction was stirred at 0° C. for 2 hours. Then the reaction mixture was concentrated to dryness. The residue was diluted with ethyl acetate (80 ml) and a aqueous solution of ammonium chloride (40 ml). An extraction was performed with brine (40 ml). The water layer was again extracted with EtOAc (80 ml). The organic layers were collected, dried over Na2SO4, filtered and concentrated to dryness, yielding 5.5 g of intermediate shown, used crude in the next step.

1.2(3) Preparation of Intermediate

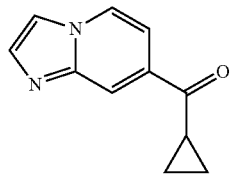 [SMILES: O=C(c1ccn2ccnc2c1)C1CC1]

To a suspension of intermediate of example 1.2(2) (27.36 mmol) in DCM (132 ml) was added manganese oxide (54.721 mmol) under vigourous stirring. After 2 hours, 4 hours and 6 hours 2 eq of manganese oxide (3×4.8 g) were added and the reaction was left overnight. 2 more eq of manganese oxide (4.8 g) were added and the reaction was left for 4 hours. The reaction was stopped. The reaction mixture was filtered over dicalite and the filtrate was evaporated under reduced pressure at 40° C. and dried in vacuo at 50° C., yielding 3.7 g of intermediate shown.

The product was used as such in the next reaction.

1.2(4) Preparation of Intermediate

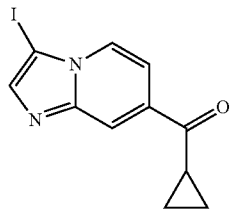 [SMILES: O=C(c1ccn2c(I)cnc2c1)C1CC1]

To a mixture of intermediate of example 1.2(3) (23.057 mmol) in DMF (25 ml), 0.6 eq (3.1 g) of N-iodosuccinimide was added and the reaction mixture was stirred at room temperature for 1 hour. 0.7 eq (3.6 g) of N-iodosuccinimide was added and the reaction was left 1 hour. The reaction was stopped. The solution was slowly dropped into 200 ml of distilled water and 20 ml of a 20% solution of sodium bisulfite. After stirring for 10 minutes at room temperature, the slurry was filtered, washed with diethyl ether and the resulting solid was dried in vacuo at 50° C., yielding 3.14 g of intermediate shown.

1.2(5) Preparation of Intermediate

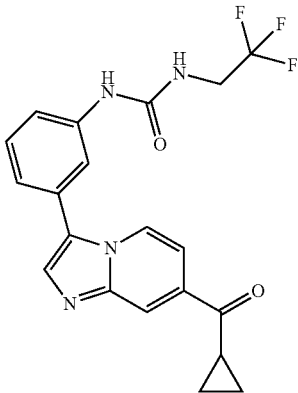 [SMILES: O=C(NCC(F)(F)F)Nc1cccc(-c2cnc3cc(C(=O)C4CC4)ccn23)c1]

Intermediate of example 1.2(4) (14.738 mmol) and intermediate of example 1.1.a(4) (15.475 mmol) in dioxane (150 ml) were charged in a large vial. Nitrogen was bubbled in the reaction mixture under stirring. Phosphoric acid, potassium salt (1:3) (29.477 mmol) in water (50 ml) was added followed by dichloro(diphenylphosphinoferrocene)palladium (0.737 mmol) and the stirring under bubbling nitrogen was continued for 10 minutes.

The reaction mixture was left at 95° C. (reflux) for 4 hours and then diluted with 20 ml water and extracted with ethyl acetate (100 ml). The aqueous phase was extracted twice with ethyl acetate (50 ml). The combined organic phases were again washed with water, dried over sodium sulfate, filtered and concentrated under reduced pressure. The residue was triturated with MeOH/DCM 5/95 solution and filtered off, washed with DIPE (5 ml), dried in vacuo at 40° C. overnight, yielding 2,678 g of intermediate shown.

The filtrate was left overnight and the formed precipitate was filtered off, washed with DIPE, dried in vacuo at 50° C. for 4 hours, yielding 1,237 g of intermediate shown. The filtrate was evaporated under reduced pressure, triturated in 20 ml 2/98 MeOH/DCM and poured in 300 ml DIPE under vigourous stirring. The precipitate was filtered off, washed with DIPE and dried in vacuo at 50° C. for 4 hours. The residue (1.71 g) was crystallized in acetonitrile, filtered and washed with DIPE, yielding 1.1 g of intermediate shown.

1.2(6) Preparation of Compound

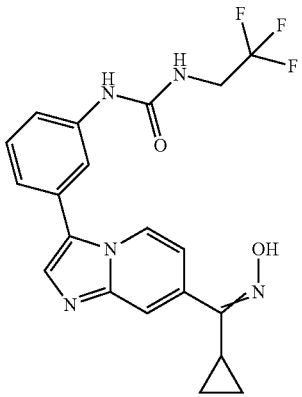 [SMILES: O=C(NCC(F)(F)F)Nc1cccc(-c2cnc3cc(C(=NO)C4CC4)ccn23)c1]

To a stirring suspension of intermediate of example 1.2(5) (6.636 mmol) in ethanol (30 ml) and pyridine (2 ml) was added hydroxylamine, hydrochloride (1:1) (13.271 mmol) and the reaction was stirred at 50° C. for 1 hour. Ethanol and pyridine were added until solution (30 ml ethanol, 6 ml pyridine) and the reaction was left overnight at 50° C. under stirring. The solvents were evaporated under reduced pressure at 40° C. until 3 mbar (2 hours). The sticky fraction was triturated ultrasonicly with a minimum of water, filtrated, washed with Ediethyl ether and dried in vacuo at 50° C. overnight. The residue (2.33 g) was crystallized in acetonitrile. The crystals were washed with acetonitrile and diethyl ether and dried in vacuo at 50° C. for 4 hours, yielding 1.1 g of compound shown.

EXAMPLE1.3.a

1.3.a(1) Preparation of Intermediate

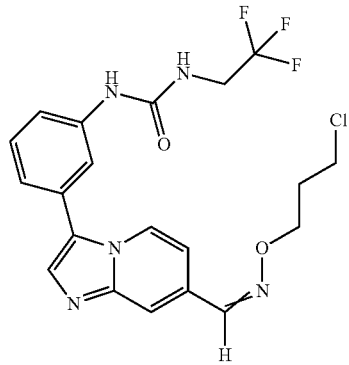

To a mixture of intermediate of example 1.1.a(6) (5.3 mmol) and 1,3-bromochloropropane (10.601 mmol) in DMSO (25 ml) was added cesium carbonate (10.601 mmol). The reaction mixture was stirred at room temperature for 1 hour. The reaction mixture was dropped into distilled water, then the product was extracted with ethyl acete and NaOH 1M. The organic layers were collected, dried over Na$_2$SO$_4$, filtered and concentrated to dryness. The residue was purified by chromatography (DCM/MeOH). The pure fractions were collected and the solvent was evaporated, yielding 1.505 g of intermediate shown.

1.3.a(2) Preparation of Final Compound

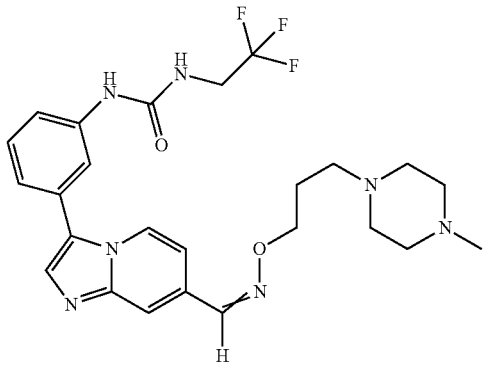 [SMILES: CN1CCN(CCCON=Cc2ccn3c(-c4cccc(NC(=O)NCC(F)(F)F)c4)cnc3c2)CC1]

Intermediate of example 1.3.a(1) (0.881 mmol) in 1-methyl-piperazine (1.5 ml) was stirred at 70° C. for 20 hours. The crude sample was submitted to preparative purification (Gemini C18 120 A 10 microm (Phenomenex), 50 mm by 16.5 cm) (gradient: (A: 0.25% ammonium bicarbonate in water; B: acetonitrile from 90/10 to 65/35 in 44 minutes and then 0/100 for 8 minutes). The desired fractions were collected and worked up, yielding 224 mg of compound shown

EXAMPLE1.3.b

1.3.b(1) Preparation of Intermediate

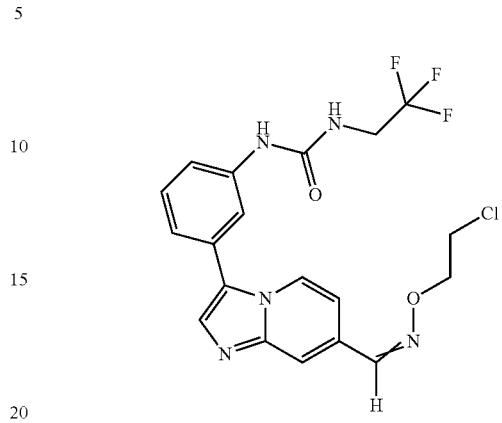

Intermediate of example 1.1.a(6) (5.3 mmol), 1-bromo-2-chloro-ethane (26.502 mmol), and cesium carbonate (26.502 mmol) in DMSO (50 ml) were placed in a sealed tube and stirred at room temperature for 1 hour. The solution was poured into water and extracted 2 times with ethyl acetate. The combined organic phases were dried over sodium sulfate, filtered and evaporated under reduced pressure, yielding 2.3 g of intermediate shown. The crude product was used as such in the next step,

1.3.b(2) Preparation of Compound

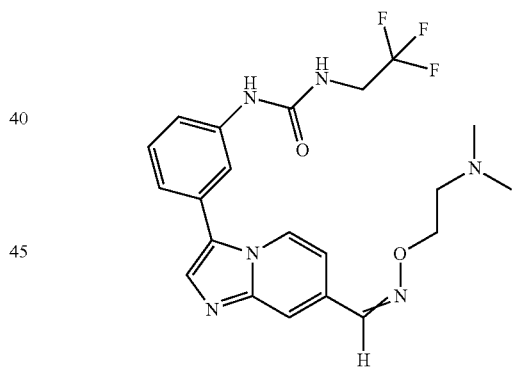

A solution of intermediate of example 1.3.b(1) (0.909 mmol) and potassium iodide (0.136 mmol) in DMF (15 ml) was treated with 2-(methylsulfonyl)-ethanamine, hydrochloride (1:1) (2.728 mmol) at ambient temperature. The reaction mixture was heated up to 100° C. and stirred for 18 hours. The reaction was completed and the solvent was removed under reduced pressure. The residual fraction was treated with ice-water and the product was extracted with ethyl acetate (3×). The organic layer was dried (MgSO$_4$), filtered and evaporated to dryness. The crude residual fraction was purified by high-performance liquid chromatography (RP-18) (eluent:(0.25% NH$_4$HCO$_3$ in H$_2$O)/CH$_3$CN/MeOH//80/10/10; 20/40/40; 0/50/50 v/v). The desired fractions were collected and evaporated to dryness. The product was coevaporated with toluene and the residual fraction was dried under N2-flow at 30° C., yielding 141 mg of compound shown.

EXAMPLE1.3.c

Preparation of Compound

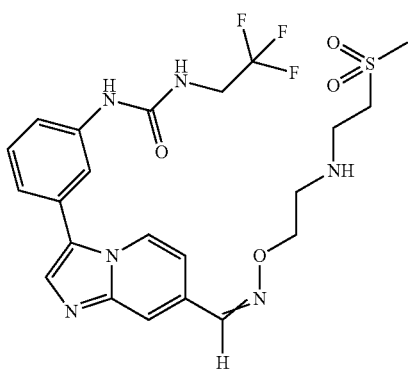 [SMILES: CS(=O)(=O)CCNCCON=Cc1ccn2c(-c3cccc(NC(=O)NCC(F)(F)F)c3)cnc2c1]

A solution of intermediate of example 1.3.b(1) (0.909 mmol), potassium iodide (0.136 mmol) and N-ethyldiisopropylamine (3.638 mmol) in DMA (15 ml) was treated with 2-(methylsulfonyl)-ethanamine, hydrochloride (1:1) (1.819 mmol) at ambient temperature. The reaction mixture was heated up to 100° C. and stirred for 18 hours. The reaction was completed and allowed to reach room temperature. The solution was poured out into ice-water and the product was extracted with ethyl acetate (3×). The organic layer was dried (MgSO$_4$), filtered and evaporated to dryness. The crude residual fraction was purified by high-performance liquid chromatography (RP-18) (eluent:(0.25% NH$_4$HCO$_3$ in water)/CH$_3$CN/100/0-65/35-0/100 v/v) The desired fractions were collected and evaporated to dryness. The residual fraction was repurified under the same conditions. The product was coevaporated with toluene and the residual fraction was dried under vacuo at 30° C., yielding 30 mg of compound shown.

EXAMPLE1.3.d

Preparation of Compound

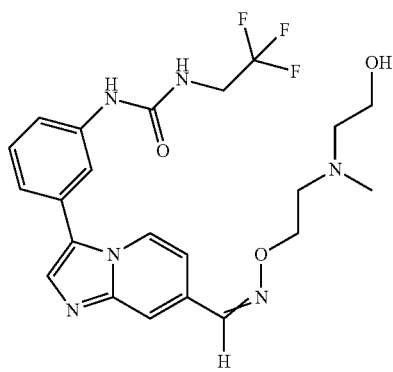 [SMILES: CN(CCO)CCON=Cc1ccn2c(-c3cccc(NC(=O)NCC(F)(F)F)c3)cnc2c1]

Intermediate of example 1.3.b(1) (0.909 mmol) and 2-(methylamino)-ethanol (4.547 mmol) in DMA (10 ml) were placed in a sealed tube and stirred at room temperature for 18 hours. The mixture was poured into water and the formed precipitate was filtered off, washed with water. The residue was dissolved in ethyl acetate, dried (MgSO$_4$) and filtered. The filtrated was concentrated under reduced pressure. A yellow solid was formed. The crude residual fraction was purified by high-performance liquid chromatography (RP-18) (eluent:(0.25% NH$_4$HCO$_3$ in water)/CH$_3$CN//90/10; 40/60; 0/100 v/v). The desired fractions were collected and evaporated to dryness. The product was co-evaporated with toluene and the residual fraction was dried under N$_2$-flow at 30° C., yielding 232 mg of compound shown.

EXAMPLE1.4.a 1.4.a(1) Preparation of Intermediate

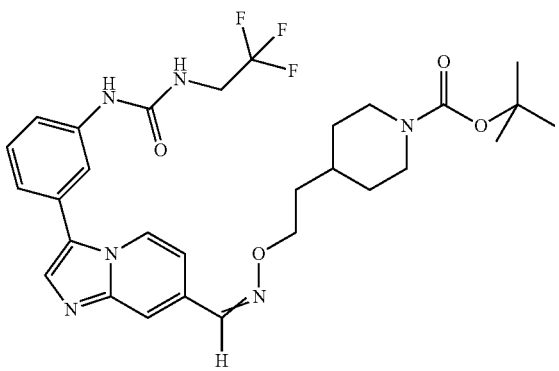 [SMILES: CC(C)(C)OC(=O)N1CCC(CCON=Cc2ccn3c(-c4cccc(NC(=O)NCC(F)(F)F)c4)cnc3c2)CC1]

Intermediate of example 1.1.a(6) (2.65 mmol), 4-(2-chloroethyl)-1-piperidinecarboxylic acid (CAS 184042-53-3), 1,1-dimethylethyl ester (5.3 mmol), and cesium carbonate (7.951 mmol) in DMSO (30 ml) were placed in a sealed tube and stirred at room temperature for 20 hours. The solution was poured into water and extracted 3 times with ethyl acetate.

The combined organic phases were dried over MgSO$_4$, filtered and evaporated under reduced pressure, yielding 1.5 g of intermediate shown. The crude residual fraction was used as such in the next step.

1.4.a(2) Preparation of Compound

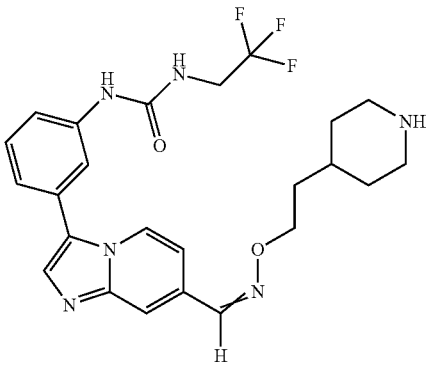 [SMILES: O=C(NCC(F)(F)F)Nc1cccc(-c2cnc3cc(C=NOCCC4CCNCC4)ccn23)c1]

A solution of intermediate 1.4.a(1) (2.548 mmol), trifluoro-acetic acid (2.548 mmol) and DCM (20 ml) was stirred at room temperature for 1 hour. The solution was concentrated under reduced pressure and the residue was dissolved in DCM and washed with a saturated aqueous NaHCO$_3$ solution. The organic layer was dried (MgSO$_4$), filtered and evaporated to dryness, yielding 1.2 g of compound shown.

EXAMPLE1.4.b 1.4.b(1) Preparation of Intermediate

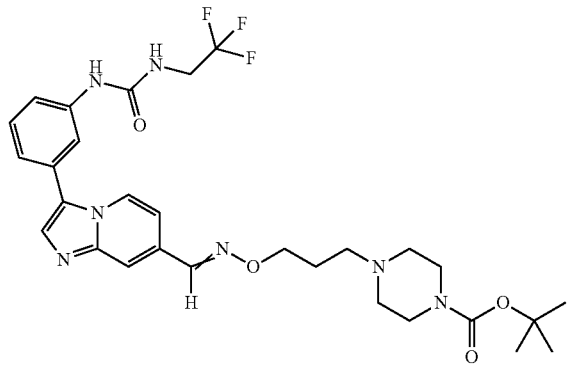 [SMILES: CC(C)(C)OC(=O)N1CCN(CCCON=Cc2ccn3c(-c4cccc(NC(=O)NCC(F)(F)F)c4)cnc3c2)CC1]

Intermediate of example 1.3.a(1) (5.31 mmol) and 4-t-butyloxy-piperazine (53.101 mmol) were heated at 70° C. in a round bottom flask for 20 hours. Extra 4-t-butyloxy-piperazine was added and the stirring at 70° C. was continued for additional 50 hours. The mixture was dissolved in DCM (250 ml) and washed with a saturated solution of NaHCO$_3$. The organic phase was dried over sodium sulfate, filtered and evaporated under reduced pressure. The crude sample was purified by flash chromatography using a gradient of DCM/MeOH from 98/2 to 95/5, yielding 7.8 g of intermediate shown. This intermediate was used in the next step without further purification.

1.4.b(2) Preparation of Compound (A)

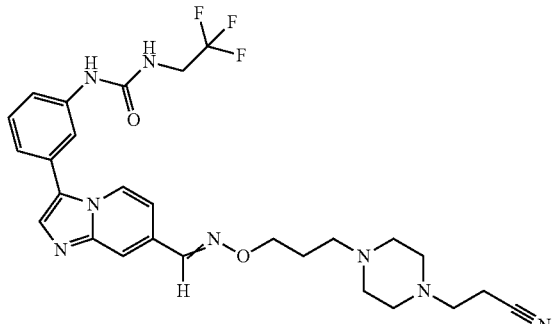

(B)

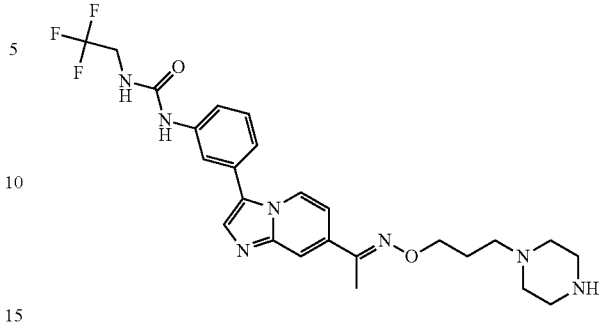

To a solution of intermediate 1.4.b(1) (12.922 mmol) in DCM (300 ml) was added trifluoro-acetic acid (30 ml). After 5 hours, the reaction mixture was basified with a saturated solution of ammonia in methanol. The solvent was evaporated under reduced pressure. The residue was purified by reverse-phase chromatography using a Hyperprep C18 HS BDS 100 Å 8 μm (Shandon) column (50 mm diameter, 16.5 cm length) and ammoniumbicarbonate in water 0.25%-acetonitrile-methanol mixture as eluent. The product purified reacted with the solvents used in the purification step and yielded compound 1.4.b(2)A and compound 1.4.b(2)B as shown.

EXAMPLE1.5

1.5(1) Preparation of Intermediate

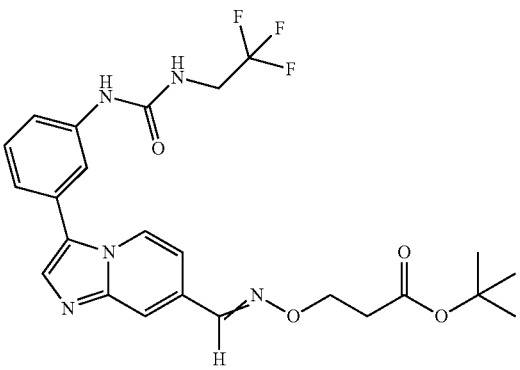 [SMILES: CC(C)(C)OC(=O)CCON=Cc1ccn2c(-c3cccc(NC(=O)NCC(F)(F)F)c3)cnc2c1]

Intermediate of example 1.1.a(6) (2.65 mmol), 2-propenoic acid, 1,1-dimethylethyl ester (18.022 mmol), and potassium hydroxide (1.855 mmol) in ethanol (10 ml) were placed in a sealed tube and stirred for days at 45° C. for 2 days. Then, over a period of days, each day 1 equivalent of 2-propenoic acid, 1,1-dimethylethyl ester was added to the reaction mixture. The reaction was completed for about 70% and the work-up of the reaction was started. The solvent was removed under reduced pressure and the residual fraction was dissolved in DCM and washed with a 10% NaOH solution and water. The unsoluble fraction was removed by filtration. The organic layer was dried with MgSO$_4$, filtered and concentrated under reduced pressure, yielding 1.3 g of intermediate shown. The crude product was used as such in the next step,

1.5(2) Preparation of Intermediate

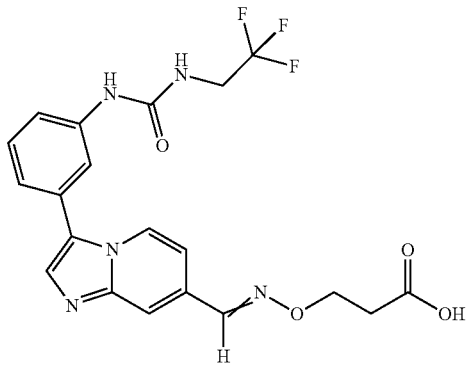 [SMILES: O=C(O)CCON=Cc1ccn2c(-c3cccc(NC(=O)NCC(F)(F)F)c3)cnc2c1]

A solution of intermediate of example 1.5(1) (1.978 mmol) in DCM (40 ml) was stirred at room temperature and trifluoro-acetic acid (15 ml) was added. The reaction mixture was stirred for 2 hours at room temperature. The solvent was removed under reduced pressure and co-evaporated with toluene to dryness. The crude residual fraction was purified by high-performance liquid chromatography (RP-180) (eluent:(0.25% $NH_4HCO_3$ in water)/$CH_3CN$ 90/10-70/30-0/100-90/10 v/v). The desired fractions were collected and evaporated to dryness. The product was co-evaporated with toluene and the residual fraction was dried under vacuo at 30° C., yielding 880 mg of intermediate shown.

1.5(3) Preparation of Compound

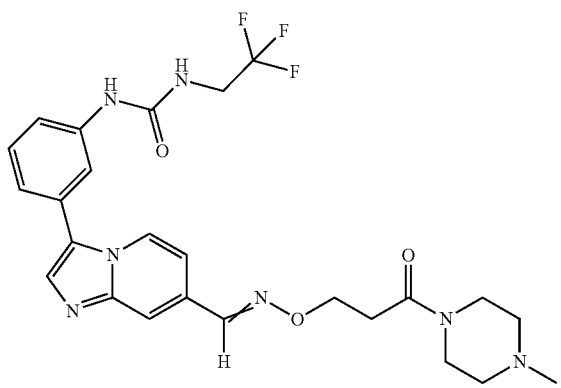 [SMILES: CN1CCN(C(=O)CCON=Cc2ccn3c(-c4cccc(NC(=O)NCC(F)(F)F)c4)cnc3c2)CC1]

A solution of intermediate 1.5(2) (0.668 mol), 1-hydroxy-1H-benzotriazole, hydrate (2.103 mmol) and N-(3-Dimethylaminopropyl)-N'-ethylcarbodiimide hydrochloride (2.203 mmol) in DMF (15 ml) was stirred at room temperature for 30 minutes, then 1-methyl-piperazine (3.338 mmol) was added and the entire reaction mixture was stirred for 18 hours. The starting material was consumed and the solvent was removed under reduced pressure. The crude residual fraction was purified by high-performance liquid chromatography (RP-18) (eluent:(0.25% $NH_4HCO_3$ in water)/MeOH/$CH_3CN$/40/60/0-0/50/50-40/60/0 v/v). The desired fractions were collected and evaporated to dryness. The product was co-evaporated with toluene and the residual fraction was dried under vacuo at 30° C., yielding 150 mg of compound shown.

EXAMPLE 1.6

1.6(1) Preparation of Intermediate

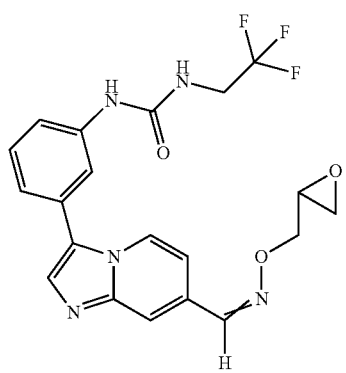 [SMILES: O=C(NCC(F)(F)F)Nc1cccc(-c2cnc3cc(C=NOCC4CO4)ccn23)c1]

Intermediate of example 1.1.a(6) (0.265 mmol), 2-(chloromethyl)-oxirane (0.53 mmol), and cesium carbonate (0.795 mmol) in DMSO (15 ml) were placed in a sealed tube and stirred at room temperature for 20 hours. The solution was poured into ice-water and the formed precipitate was filtered off. The residual fraction was desolved in DCM/MeOH (95/5), dried with $MgSO_4$, filtered and evaporated to dryness, yielding 100 mg of intermediate shown.

1.6(2) Preparation of Compound

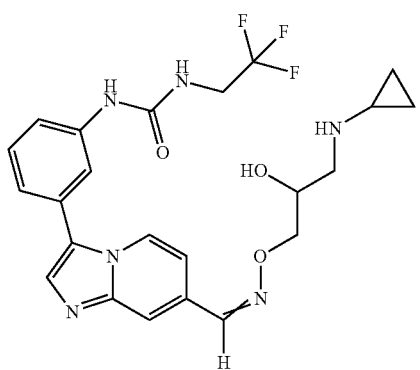 [SMILES: O=C(NCC(F)(F)F)Nc1cccc(-c2cnc3cc(C=NOCC(O)CNC4CC4)ccn23)c1]

A solution of intermediate of example 1.6(1) (0.923 mmol) and cyclopropanamine (3.692 mmol) in ethanol (10 ml) was stirred at 130° C. for 20 minutes (microwave). The reaction was completed and the solvent was removed under reduced pressure. The crude residual fraction was purified by high-performance liquid chromatography (RP-18) (eluent:(0.25% $NH_4HCO_3$ in $H_2O$)/$CH_3CN$) The desired fractions were collected and evaporated to dryness. The product was co-evaporated with toluene and the residual fraction was dried under vacuo at 50° C., yielding 108 mg of compound shown.

EXAMPLE1.7.a

1.7.a(1) Preparation of Intermediate

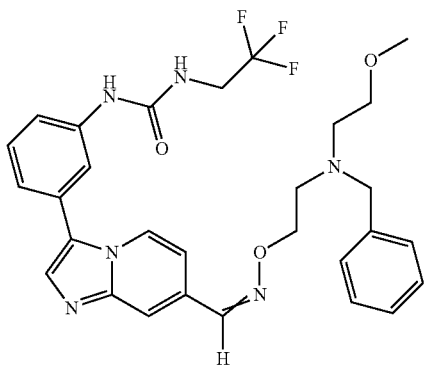 [SMILES: COCCN(CCON=Cc1ccn2c(-c3cccc(NC(=O)NCC(F)(F)F)c3)cnc2c1)Cc1ccccc1]

A solution of intermediate of example 1.3.b(1) (0.909 mmol) and potassium iodide (0.136 mmol) in DMF (15 ml) was treated with N-(2-methoxyethyl)-benzenemethanamine (5.457 mmol) at ambient temperature. The reaction mixture was heated up to 100° C. and stirred for 18 hours. The reaction was completed and allowed to reach room temperature. The solution was poured out into ice-water and the product was extracted with ethyl acetate (3×). The organic layer was dried (MgSO$_4$), filtered and evaporated to dryness. The crude residual fraction was purified by high-performance liquid chromatography (RP-18) (eluent:(0.25% NH$_4$HCO$_3$ in water)/CH$_3$CN/v/v). The desired fractions were collected and evaporated to dryness. The product was co-evaporated with toluene and the residual fraction was dried under vacuo at 50° C., yielding 215 mg of intermediate shown.

1.7.a(2) Preparation of Compound

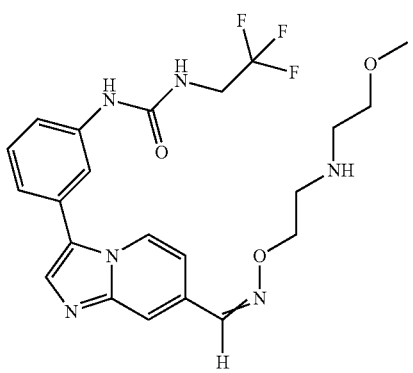 [SMILES: COCCNCCON=Cc1ccn2c(-c3cccc(NC(=O)NCC(F)(F)F)c3)cnc2c1]

Methanol (50 ml) was added to catalyst Pd/C 10% (50 mg) under nitrogen atmosphere. Intermediate of example 1.7.a(1) was added. The reaction mixture was stirred at 25° C. under hydrogen atmosphere (0.352 mmol) until 1 eq. hydrogen was absorbed. The catalyst was removed by filtration over dicalite. HPLC was performed on crude product, yielding 1 mg of compound shown.

This product was alternatively prepared by placing intermediate of example 1.1.a(1), CH$_3$—O—CH$_2$—CH$_2$—NH$_2$ and DMA in a sealed tube and stirred at room temperature for 18 hours. The mixture was poured into water and the formed precipitate was filtered off, washed with water. The residue was dissolved in AcOEt, dried (MgSO$_4$) and filtered. The filtrated was concentrated under reduced pressure. A yellow solid was formed. The crude residual fraction was purified by high-performance liquid chromatography (RP-18) (eluent: (0.25% NH$_4$HCO$_3$ in H$_2$O)/CH$_3$CN//90/10-75/25-0/100 v/v). The desired fractions were collected and evaporated to dryness. The product was coevaporated with toluene and the residual fraction was dried under N$_2$-flow at 30° C. The product was repurified under the same conditions, yielding 27.6% of compound shown.

EXAMPLE1.7.b

1.7.b(1) Preparation of Intermediate

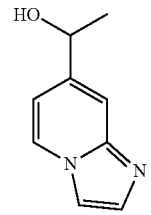

To a solution of imidazo[1,2-a]pyridine-7-carboxaldehyde [136117-73-2](13.685 mmol) in THF (150 ml) was added at 0° C. bromomethyl-magnesium in diethylether (3M) (20.527 mmol) under nitrogen atmosphere. The reaction was stirred at 0° C. for 2 hours. Then the reaction mixture was concentrated to dryness. The residue was diluted with a solution of ammonium chloride and ethyl acetate. An extraction was performed with brine. The organic layers were collected, dried over Na$_2$SO$_4$, filtered and concentrated to dryness. The crude product was purified by chromatography (DCM/MeOH mixture). The pure fractions were collected and the solvent was evaporated, yielding 1902 mg of intermediate shown.

1.7.b(2) Preparation of Intermediate

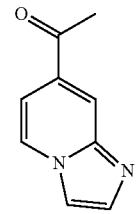

To a solution of intermediate of 1.7.b(2) (11.252 mmol) in DCM (50 ml) was added manganese oxide (activated 56.261 mmol). The reaction mixture was stirred at room temperature for 12 hours. Then the reaction mixture was filtered over a celite cake and washed with DCM. The organic layer was concentrated to dryness, yielding 1180 mg of intermediate shown. The residue was directly used into the next step.

1.7.b(3) Preparation of Intermediate

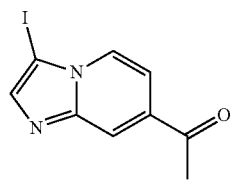

A mixture of intermediate of example 1.7.b(2) (7.367 mmol) and N-iodosuccinimide (7.735 mmol) in DMF (30 ml) was stirred at room temperature for 5 hours. The solution was slowly dropped into 300 ml of distilled water and 10 ml of a 10% solution of sodium bisulfite. After stirring for 10 minutes at room temperature, the slurry was filtered and the resulting solid was dried under vacuum, yielding 1524 mg of intermediate shown. The water layer was extracted with ethyl acetate and NaOH 1M. The organic layers were collected, dried over $Na_2SO_4$, filtered and concentrated to dryness. The residue was suspended in diethyl ether and filtered, yielding 649 mg of intermediate shown.

1.7.b(4) Preparation of Intermediate

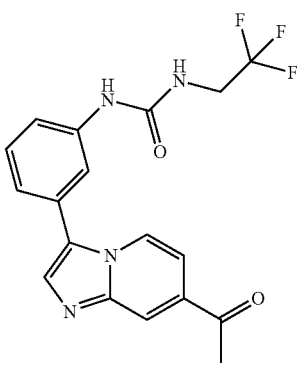 [SMILES: CC(=O)c1ccn2c(-c3cccc(NC(=O)NCC(F)(F)F)c3)cnc2c1]

A solution of intermediate of example 1.7.b(3) (6.991 mmol), intermediate of example 1.1.a(4) (8.39 mmol), dichloro(diphenylphosphinoferrocene)palladium (0.35 mmol) and phosphoric acid, potassium salt (1:3) (13.983 mmol) in dioxane (50 ml) and water (10 ml) was degassed for few minutes with nitrogen. The reaction mixture was warmed to 80° C. for 5 hours. Then the reaction mixture was filtered over a celite cake and washed with ethyl acetate. The solvent volume was reduced to half under vacuum then dropped into 400 ml of distilled water. An extraction was performed with water and brine after filtration of the resulting slurry. The organic layers were collected, dried over $Na_2SO_4$, filtered and concentrated to dryness. The residue was triturated in MeOH and filtered, yielding 2.16 g of intermediate shown.

1.7.b(5) Preparation of Final Compound

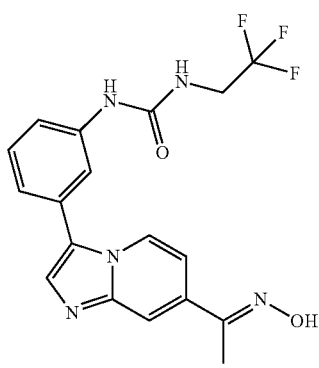 [SMILES: C/C(=N\O)c1ccn2c(-c3cccc(NC(=O)NCC(F)(F)F)c3)cnc2c1]

To a stirring suspension of intermediate of example 1.7.b (4). (4.677 mmol) in pyridine (9.353 mmol) and ethanol (25 ml) was added hydroxylamine, hydrochloride (1:1) (9.353 mmol). The solution was concentrated to dryness. The residue was crystallized in a mixture of DCM/MeOH, yielding 867 mg of compound shown. The liquid layer was concentrated and purified by chromatography (DCM/MeOH). The pure fractions were collected and the solvent was evaporated, yielding 331 mg of compound shown.

1.7.b(6) Preparation of Final Compound

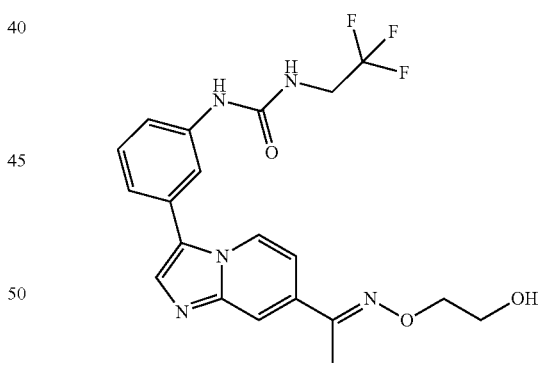

To a mixture of compound of example 1.7.b(5) (0.958 mmol) and 2-bromo-ethanol (9.582 mmol) in DMSO (10 ml) was added cesium carbonate (3.833 mmol). The reaction mixture was stirred at room temperature for 12 hours. The reaction mixture was slowly dropped into 100 ml of distilled water. After stirring for a few minutes, the slurry was filtered and dried under vacuum. The crude product was triturated in acetonitrile then filtered. The product was purified by chromatography (DCM/MeOH mixture) and further purified by reverse-phase chromatography using a Hyperprep C18 HS BDS 100 Å 8 μm (Shandon) column (50 mm diameter, 16.5 cm length) and acetonitrile-water mixture as eluent, yielding 211 mg of compound shown.

EXAMPLE1.7.c

Preparation of Final Compound

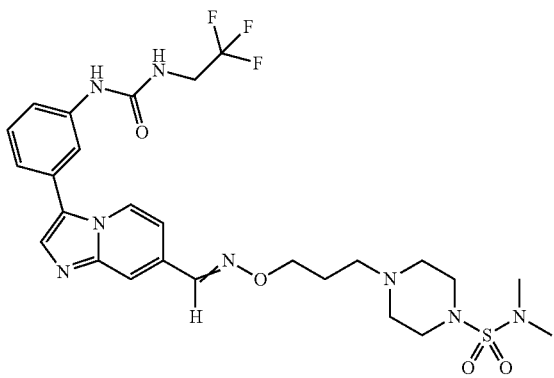 [SMILES: CN(C)S(=O)(=O)N1CCN(CCCON=Cc2ccn3c(-c4cccc(NC(=O)NCC(F)(F)F)c4)cnc3c2)CC1]

To a solution of compound of example 1.4.b(2)B (1.704 mmol) and N,N-diethyl-ethanamine (1.022 mmol) in acetonitrile (5 ml) was added dimethylsulfamoyl chloride (0.852 mmol) at room temperature. After 3 hours, 0.1 eq of dimethylsulfamoyl chloride (18 uL) was added. Dimethylsulfamoyl chloride and N,N-diethyl-ethanamine were added again and the suspension was stirred for 48 hours. Acetonitrile (10 ml) was added and the precipitate was filtered and washed with acetonitrile. The filtrate was evaporated under nitrogen flow at 50° C. The crude sample (result of the evaporation of the filtrate) was submitted to preparative purification (Hyperprep C18 HS BDS 100 A 8 μm, 50 mm by 16.5 cm) (gradient: (A: 0.25% ammonium bicarbonate in water; B: acetonitrile from 80/20 to 20/80 in 45 minutes and then 0/100 for 8 minutes and finally 80/20 for an additional 10 minutes). The desired fractions were collected and worked up, yielding 78 mg of compound shown.

EXAMPLE1.8

1.8(1) Preparation of Intermediate

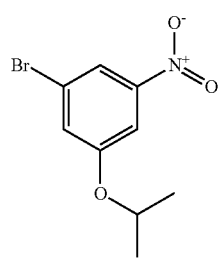

A solution of 3-bromo-5-nitrophenol (CAS 116632-23-6) (16 g, 73.39 mmol), 2-iodopropane (14.68 ml, 146.79 mmol) and K2CO3 (20.29 g, 146.79 mmol) in DMF (80 ml) was stirred overnight at room temperature. The reaction mixture was poured into water and AcOEt. The organic layer was washed with water then brine, dried over MgSO₄, filtered and the solvent was evaporated to give 18.3 g (95.9%) of intermediate shown

1.8(2) Preparation of Intermediate

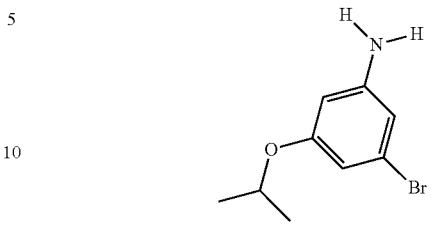

TiCl₃ (474.53 ml, 553.66 mmol) was added dropwise to a solution of intermediate of example 1.8(1) (16 g, 61.52 mmol) in THF (240 ml) at room temperature. The mixture was stirred at room temperature for 2 days. Water and AcOEt were added. K₂CO₃ powder was added until basic pH. The mixture was filtered over celite. Celite was washed with AcOEt. The organic layer was separated, dried over MgSO₄, filtered and evaporated, yielding 14 g (98.9%) of intermediate shown.

1.8(3) Preparation of Intermediate

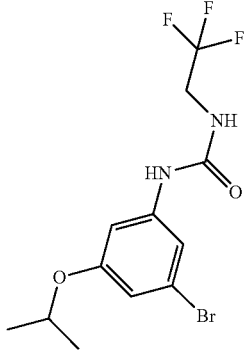 [SMILES: CC(C)Oc1cc(Br)cc(NC(=O)NCC(F)(F)F)c1]

A mixture of intermediate of example 1.8(2) (16 g, 69.53 mmol) and 4-nitrophenyl carbonochloridic acid, ester (15.42 g, 76.49 mmol) in THF (400 ml) was heated at 60° C. for 1 hour, then allowed to cool down to room temperature. N,N-Diethylethanamine (9.68 m, 69.53 mmol) then 2,2,2-trifluoroethanamine 5% (6.11 ml, 76.49 mmol) were added dropwise at room temperature. The mixture was heated at 60° C. for 12 hours. After cooling down to room temperature, THF was evaporated. The mixture was poured out into ice/water and AcOEt was added. The organic layer was washed successively with 10% K₂CO₃ aqueous solution, 3N HCl aqueous solution and water. The organic layer was separated, dried (MgSO₄), filtered and the solvent was evaporated. The residue was taken up into diethyl ether, filtered and dried to give 11.6 g of fraction 1.

The filtrate was evaporated and taken up into Et₂O. The precipitate was filtered off and dried to afford 5.5 g of fraction 2.

The fraction 1 and fraction 2 were combined to give 17.1 g (69.2%) of intermediate shown.

1.8(4) Preparation of Intermediate

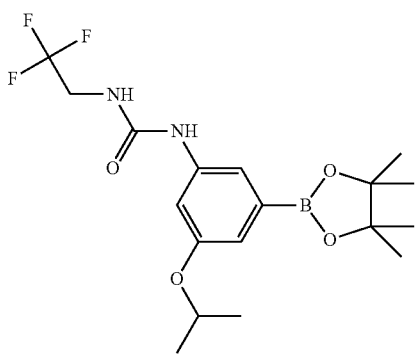 [SMILES: CC(C)Oc1cc(NC(=O)NCC(F)(F)F)cc(B2OC(C)(C)C(C)(C)O2)c1]

A mixture of intermediate of example 1.8(3) (6.5 g, 18.30 mmol), 4,4,4',4',5,5,5',5'-octamethyl-2,2'-bi-1,3,2-dioxaborolane, (6.3 g, 24.7 mmol) and potassium acetate (5.39 g, 54.91 mmol) in dimethyl sulfoxide (100 ml) was stirred and degassed with $N_2$ for 15 minutes. 1,1'bis(diphenylphosphino) ferrocenedichloro palladium (401.75 mg, 0.55 mmol) was added. The mixture was heated at 100° C. for 6 hours. More 4,4,4',4',5,5,5',5'-octamethyl-2,2'-bi-1,3,2-dioxaborolane (900 mg, 3.55 mmol) was added and the mixture was stirred at 100° C. for another 4 hours.

The mixture was poured into water, AcOEt was added and the mixture was filtered through a layer of celite. The organic layer was separated, the organic layer was washed with water then brine, dried over $MgSO_4$, filtered and evaporated to dryness. The crude product was taken-up into DIPE, stirred at room temperature for one hour, the precipitated was filtered, washed with DIPE and the filtrate was evaporated to give 5.6 g (76.0%) of intermediate shown.

1.8(5) This intermediate was used to prepare final compound 1-31 from Table 1 according to Example 1.2(6).

EXAMPLE 1.9

1.9(1) Preparation of Intermediate

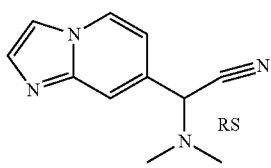

Intermediate of example 1.2(1) in a minimum of methanol was added slowly (45 minutes) to a solution of dimethylamine hydrochloride and Sodium cyanide in Water. The solution was stirred for 5 hours under $N_2$ flow at room temperature. The reaction was left over night. The reaction mixture was quenched with water (100 ml), evaporated under reduced pressure to water, and extracted with DCM (3×100 ml) and once with brine (50 ml). The reaction mixture was then evaporated until 10 ml water and again extracted with DCM (100 ml). The combined green organic layers were washed with a saturated aqueous solution of sodium metabisulphite (3×50 ml), again with water (2×50 ml), dried over $Na_2SO_4$ anhydric and filtered.

The filtrate was evaporated under reduced pressure at 40° C. until 10 mbar for 3 hours to yield 13.3 g of intermediate shown.

1.9(2) Preparation of Intermediate

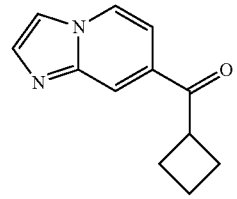 [SMILES: O=C(c1ccn2ccnc2c1)C1CCC1]

To a NaH suspension in oil, washed with hexane and suspended in dry DMF (2 ml) under $N_2$ flow, was added a solution of intermediate of example 1.9(1) in 4 ml dry DMF. The resulting red suspension was stirred under $N_2$ at room temperature for 1 hour. Cyclobuthylbromide was added slowly (10 minutes) and the reaction was left for 6 hours. The reaction was for 48 hours. The reaction mixture was added to a 5N HCl aqueous solution (200 ml) under vigourous stirring and extracted with AcOEt (2×200 ml). The water layer was made basic with a NaOH solution 25% and extracted with DCM (2×200 ml). The combined organic layers were washed with water (3×30 ml), dried with Na2SO4 anhydric, filtered and the filtrate was evaporated under reduced pressure. The resulting oil was brought into emulsion by adding 3×30 ml water and the emulsion was extracted with DCM (3×30 ml). The combined organic layers were dried with $Na_2SO_4$ anhydric, filtered and the filtrate was evaporated under reduced pressure and dried in vacuo at 50° C. for 1 hour to yield 5.99 g of intermediate shown.

1.9(3) The intermediate was used as such in the reaction protocol to prepare compound 1-28 detailed below in Table A1.

1.9(4) The intermediate was used as such in the reaction protocol to prepare compound 1-27 detailed below in Table A1.

EXAMPLE 1-10

1.10(1) Preparation of Intermediate

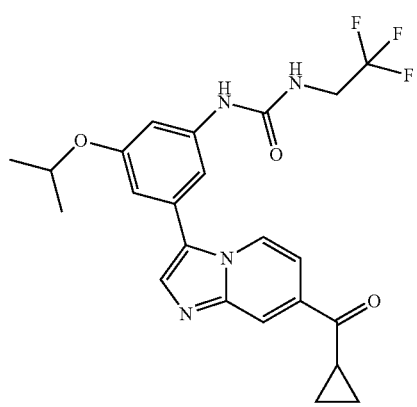 [SMILES: CC(C)Oc1cc(NC(=O)NCC(F)(F)F)cc(-c2cnc3cc(C(=O)C4CC4)ccn23)c1]

A mixture of intermediate of example 1.2(4) (750 mg, 2.07 mmol), intermediate of example 1.8(4) (962.5 mg, 2.27 mmol), PdCl$_2$ (dppf) (84.3 mg, 0.1 mmol, 0.05 eq) and K$_3$PO$_4$.H$_2$O (952 mg, 4.1 mmol) in dioxane (30 mL) and water (5 mL) was stirred under N$_2$-flow at reflux for 6 hours. The reaction mixture was diluted with water (150 mL), extracted with ethyl acetate and the organic layer washed with H$_2$O. The aqueous layer was extracted with ethylacetate, the organic layers were combined, dried (MgSO$_4$), filtered and evaporated to dryness. The residue was purified by Chromatography over silica gel (eluent: 96% DCM/4% MeOH). The desired fractions were collected and evaporated to dryness to yield 830 mg (84%) of the intermediate shown, melting point=192° C.

1.10 (2) Preparation of Final Compound 1-64 and 1-65

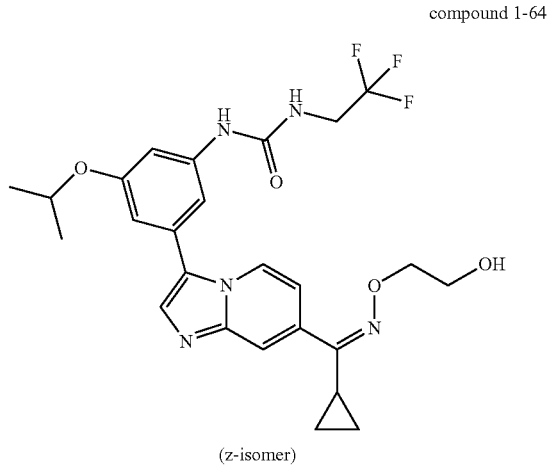

compound 1-64

(z-isomer)

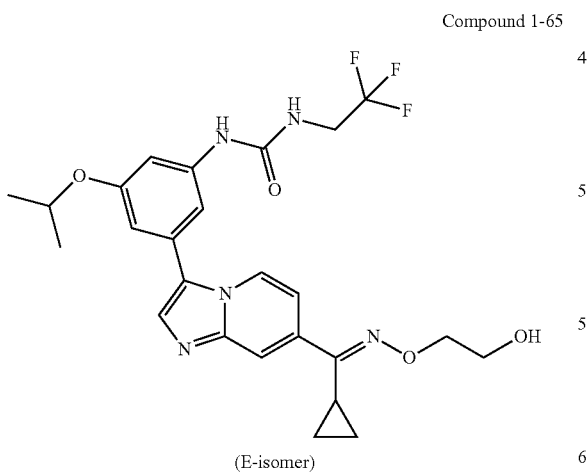

Compound 1-65

(E-isomer)

A mixture of intermediate of example 1.10(1) (350 mg, 0.76 mmol), 2-aminooxy-ethanol (CAS No. 1025727-45-0) (292. mg, 3.801 mmol) and pyridine (10 mL) in ethanol (25 mL) was stirred at 70° C. for 5 days. The solvent was removed under reduced pressure. The crude residual fraction was purified by high-performance liquid chromatography (RP-18) (eluent: Gradient:[0.25% NH$_4$HCO$_3$ in H$_2$O]/CH$_3$CN 90/10-20/80-0/100 v/v). The desired fractions were collected and evaporated to dryness. This product was further purified by HPLC on Hyperprep C18 HS BDS 100 A 8 mu (Shandon) (eluent: 60%[0.25% NH$_4$HCO$_3$ in H$_2$O]/40% CH$_3$CN, then the column was rinsed with 100% CH$_3$CN), yielding 168 mg (42%) of compound 1-65 (the E isomer) and 57 mg (14%) of compound 1-64 (the Z isomer).

1.10 (3) Preparation of Final Compound 1-66 and 1-67

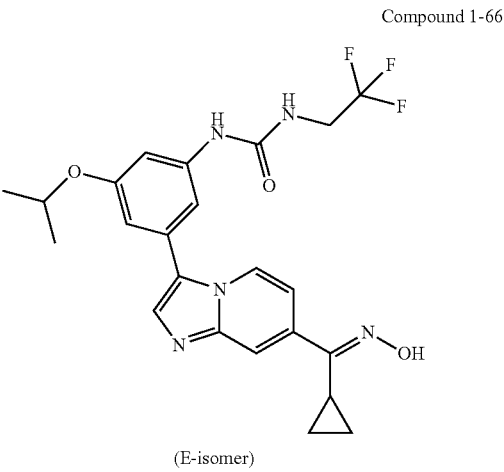

Compound 1-66

(E-isomer)

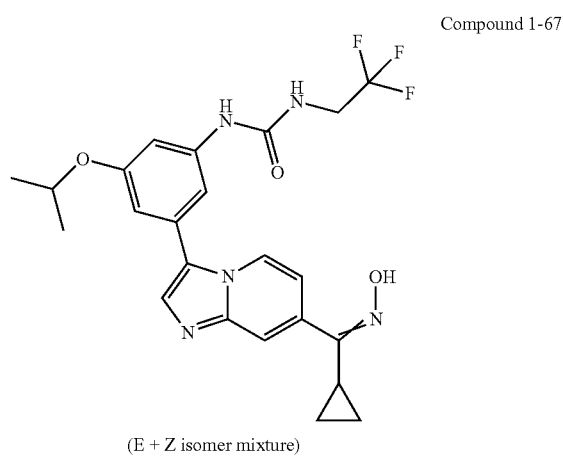

Compound 1-67

(E + Z isomer mixture)

To a stirring suspension of the intermediate of example 1.10 (1) (8.54 g, 14.096 mmol) in ethanol (80 mL) and pyridine (10 mL) was added hydroxylamine.HCl (1.959 g, 28.191 mmol). The reaction was stirred at 50° C. overnight. The solvent was evaporated under reduced pressure (4 mbar) at 45° C. The residue was purified over silicagel (Irregular SiOH, gradient 95% DCM/5% MeOH to 90% DCM/10% MeOH). The desired product fractions were collected and evaporated under reduced pressure to yield compound 1-66 as a white solid (2.0 g) (93% (E)/7% (Z) by NMR, melting point=222-223° C.). Other product fractions were collected and re-purified over 200 g of Silicagel (60A 25-40 μm, Merck; art. 9390; gradient 96% DCM/4% MeOH to 90% DCM/10% MeOH). The collection and evaporation of the remaining fractions yielded compound 1-67 as a white solid (80 mg) and a brown residue (860 mg) which both represent a mixture of the E and Z isomers.

1.10(4) Preparation of Intermediate

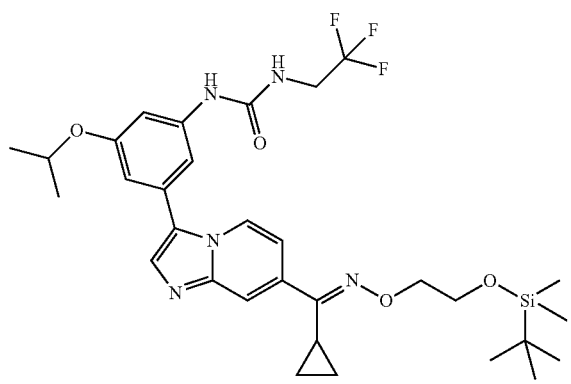 [SMILES: CC(C)Oc1cc(NC(=O)NCC(F)(F)F)cc(-c2cnc3cc(/C(=N/OCCO[Si](C)(C)C(C)(C)C)C4CC4)ccn23)c1]

To a mixture of the compound 1-66 from example 1.10 (3) (1 g, 2.1 mmol) and cesium carbonate (1370 mg, 4.2 mmol) in DMSO (35.4 mL; 496.2 mmol) at room temperature was added (2-bromoethoxy)(tert-butyl)dimethylsilane (CAS no. 86864-60-0) (2.5 mL, 11.6 mmol). The reaction was left for 1 hour. The reaction mixture was poured into 10 mL water under vigourous stirring. Ethyl acetate (20 mL) was added under stirring. Both layers were separated and the water layer was extracted with ethyl acetate (20 mL). The organic layers were combined, washed with water (2×5 ml) and dried over anhydrous $Na_2SO_4$ and evaporated under reduced pressure at 28° C. til dry. This residue (1.334 g) was used as such in the next reaction(s).

1.10 (5) Preparation of Final Compound 1-65

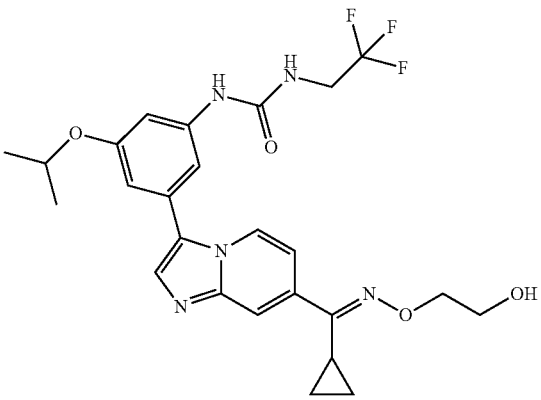 [SMILES: CC(C)Oc1cc(NC(=O)NCC(F)(F)F)cc(-c2cnc3cc(/C(=N/OCCO)C4CC4)ccn23)c1]

Compound 1-65 was alternatively prepared as follows:

To the intermediate of example 1.10 (4) (1.332 g, 2.1 mmol) in THF (5.2 mL) and water (5.2 mL) was added acetic acid (100%, 15.6 mL) and the reaction was stirred at room temperature for 48 hours. Reaction was quenched with 50 mL saturated aqueous sodium bicarbonate solution. After stirring for 30 minutes DCM (100 mL) was added and the layers were separated. The water layer was extracted with DCM (2×100 mL) The organic layers were combined, washed with water (2×20 mL), dried ($Na_2SO_4$) and evaporated under reduced pressure to yield an orange residue (1.78 g). The residue was purified by chromatography on silica gel (Hyperprep C18 HS BDS 100 A 8 mu (Shandon); eluent: 75% [0.25% $NH_4HCO_3$ in $H_2O$]/25% $CH_3CN$, then the column was rinsed with 100% acetonitrile to yield 777 mg (70% yield) of compound 1-65.

Table A1 lists compounds that were prepared according to reaction protocols of one of the above Examples using alternative starting materials as appropriate. In Table A1, compounds are indicated as a specific isomer (e.g. E isomer) or as a mixture of E and Z isomer (these compounds are indicated in the Table by a crossed double bond (see e.g. compound 1-1).

TABLE A1

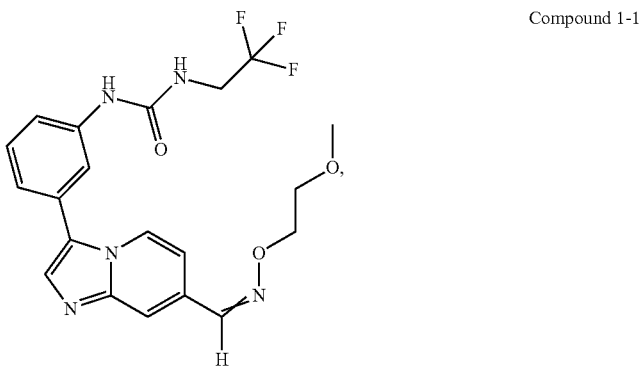

Compound 1-1

Example 1.1.a(7)

TABLE A1-continued
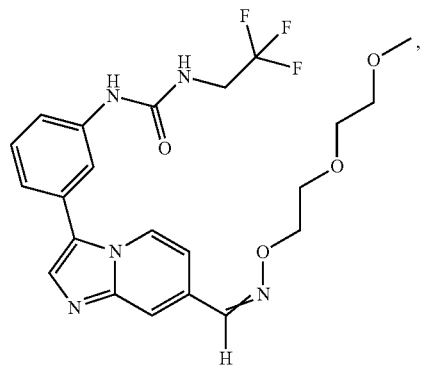 [SMILES: COCCOCCON=Cc1ccn2c(-c3cccc(NC(=O)NCC(F)(F)F)c3)cnc2c1]
Compound 1-2
Example 1.1.a(7)
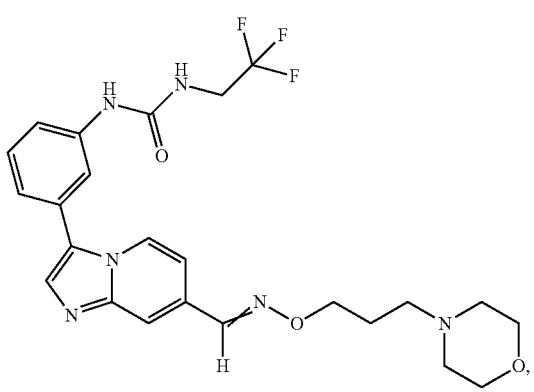 [SMILES: O=C(NCC(F)(F)F)Nc1cccc(-c2cnc3cc(C=NOCCCN4CCOCC4)ccn23)c1]
Compound 1-3
Example 1.1.a(7)
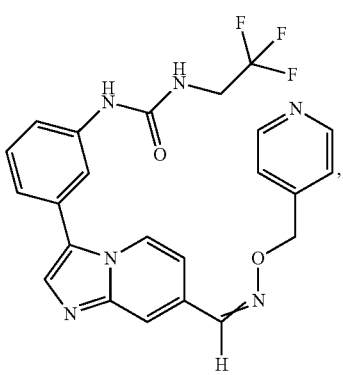 [SMILES: O=C(NCC(F)(F)F)Nc1cccc(-c2cnc3cc(C=NOCc4ccncc4)ccn23)c1]
Compound 1-4
Example 1.1.a(7)
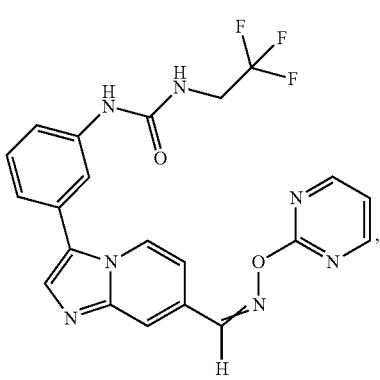 [SMILES: O=C(NCC(F)(F)F)Nc1cccc(-c2cnc3cc(C=NOc4ncccn4)ccn23)c1]
Compound 1-5
Example 1.1.a(7)

TABLE A1-continued
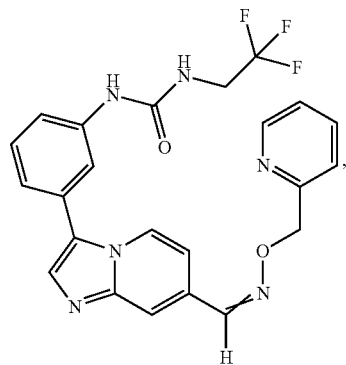 [SMILES: O=C(NCC(F)(F)F)Nc1cccc(-c2cnc3cc(C=NOCc4ccccn4)ccn23)c1]
Compound 1-6
Example 1.1.a(7)
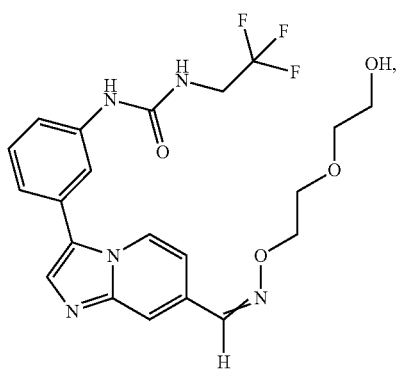 [SMILES: O=C(NCC(F)(F)F)Nc1cccc(-c2cnc3cc(C=NOCCOCCO)ccn23)c1]
Compound 1-7
Example 1.1.a(7)
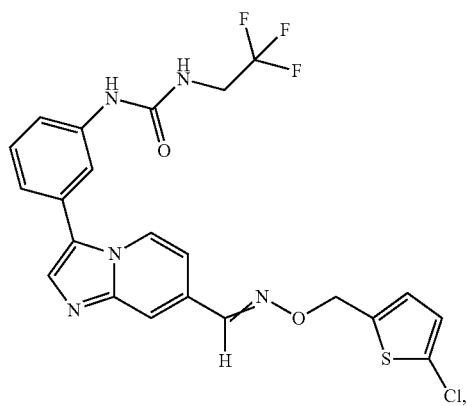 [SMILES: O=C(NCC(F)(F)F)Nc1cccc(-c2cnc3cc(C=NOCc4ccc(Cl)s4)ccn23)c1]
Compound 1-8
Example 1.1.a(7)

TABLE A1-continued
| | |
|---|---|
| 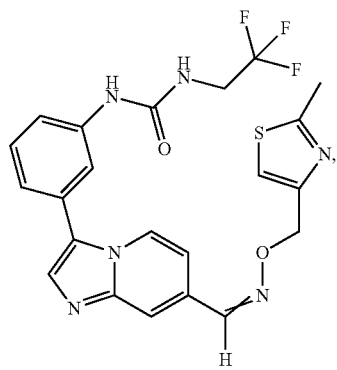 [SMILES: Cc1nc(CON=Cc2ccn3c(-c4cccc(NC(=O)NCC(F)(F)F)c4)cnc3c2)cs1]<br>Example 1.1.a(7) | Compound 1-9 |
| 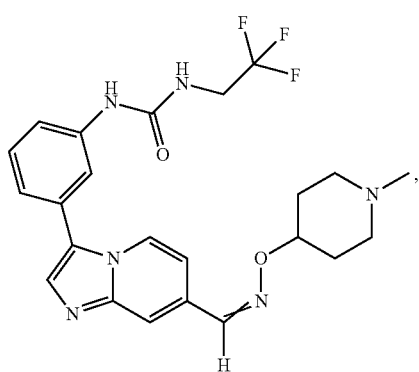 [SMILES: CN1CCC(ON=Cc2ccn3c(-c4cccc(NC(=O)NCC(F)(F)F)c4)cnc3c2)CC1]<br>Example 1.1.a(7) | Compound 1-10 |
| 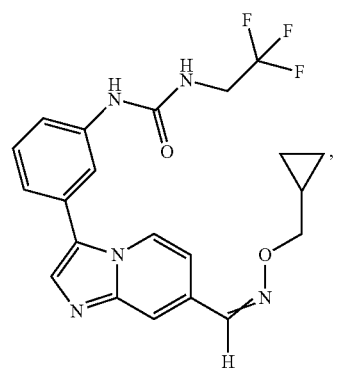 [SMILES: O=C(NCC(F)(F)F)Nc1cccc(-c2cnc3cc(C=NOCC4CC4)ccn23)c1]<br>Example 1.1.a(7) | Compound 1-11 |
| 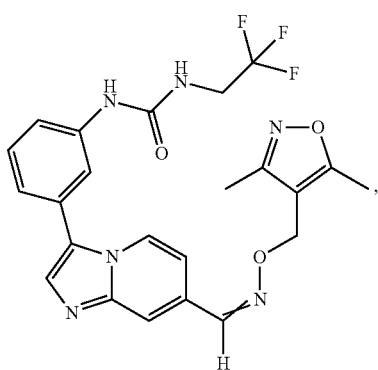 [SMILES: Cc1noc(C)c1CON=Cc1ccn2c(-c3cccc(NC(=O)NCC(F)(F)F)c3)cnc2c1]<br>Example 1.1.a(7) | Compound 1-12 |

TABLE A1-continued
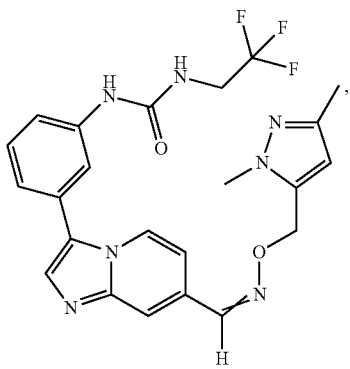 [SMILES: Cc1cc(CON=Cc2ccn3c(-c4cccc(NC(=O)NCC(F)(F)F)c4)cnc3c2)n(C)n1]
Compound 1-13
Example 1.1.a(7)
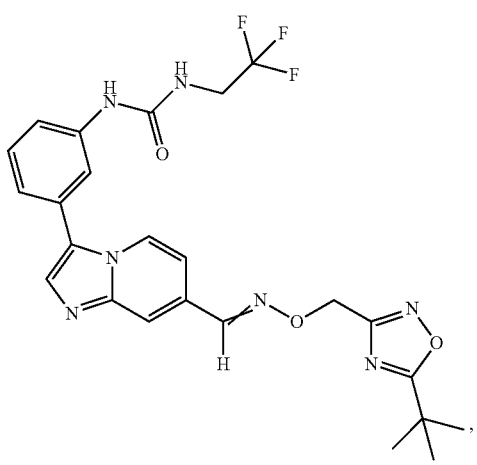 [SMILES: CC(C)(C)c1nc(CON=Cc2ccn3c(-c4cccc(NC(=O)NCC(F)(F)F)c4)cnc3c2)no1]
Compound 1-14
Example 1.1.a(7)
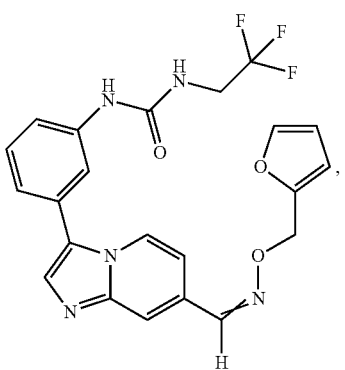 [SMILES: O=C(NCC(F)(F)F)Nc1cccc(-c2cnc3cc(C=NOCc4ccco4)ccn23)c1]
Compound 1-15
Example 1.1.a(7)

TABLE A1-continued
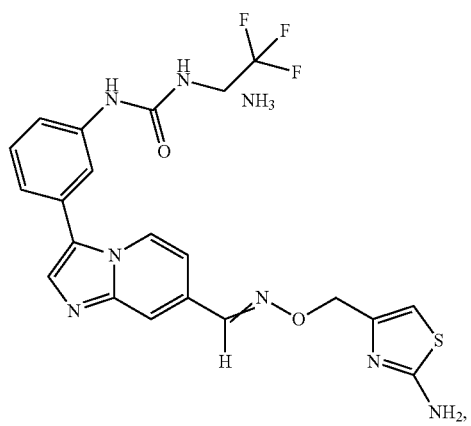
Compound 1-16
Example 1.1.a(7)
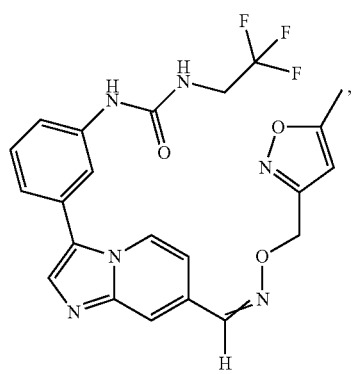 [SMILES: Cc1cc(CON=Cc2ccn3c(-c4cccc(NC(=O)NCC(F)(F)F)c4)cnc3c2)no1]
Compound 1-17
Example 1.1.a(7)
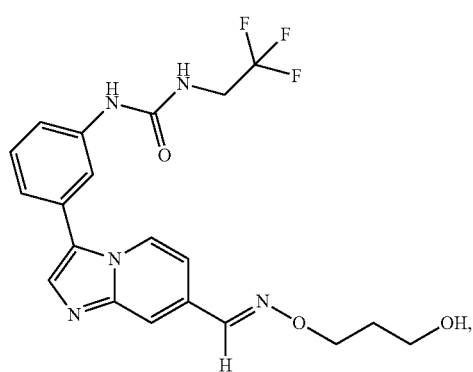 [SMILES: O=C(NCC(F)(F)F)Nc1cccc(-c2cnc3cc(/C=N/OCCCO)ccn23)c1]
Compound 1-18
Example 1.1.a(7) (E)

TABLE A1-continued
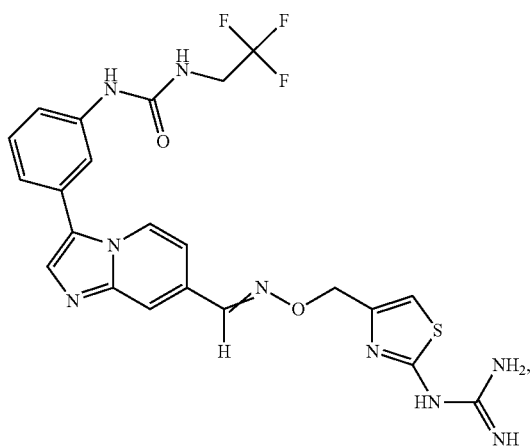 [SMILES: N=C(N)Nc1nc(CON=Cc2ccn3c(-c4cccc(NC(=O)NCC(F)(F)F)c4)cnc3c2)cs1]
Compound 1-19
Example 1.1.a(7)
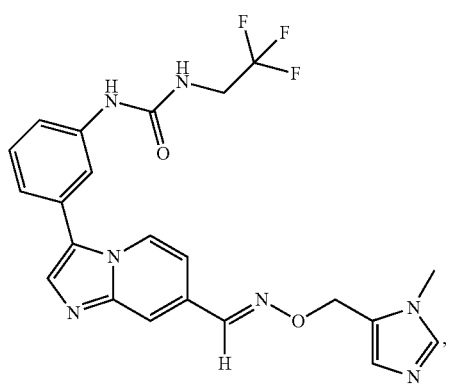 [SMILES: Cn1cncc1CO/N=C/c1ccn2c(-c3cccc(NC(=O)NCC(F)(F)F)c3)cnc2c1]
Compound 1-20
Example 1.2(6) (E)
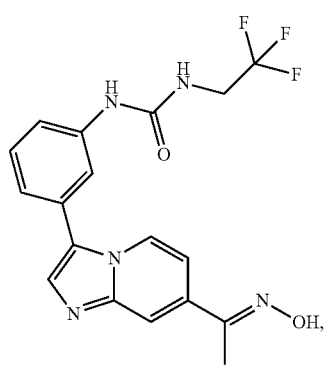 [SMILES: C/C(=N\O)c1ccn2c(-c3cccc(NC(=O)NCC(F)(F)F)c3)cnc2c1]
Compound 1-21
Example 1.2(6)-1.7.b(5) (E)

TABLE A1-continued
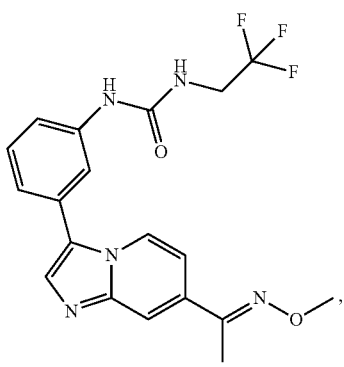 [SMILES: CO/N=C(\C)c1ccn2c(-c3cccc(NC(=O)NCC(F)(F)F)c3)cnc2c1]
Compound 1-22
Example 1.2(6) (E)
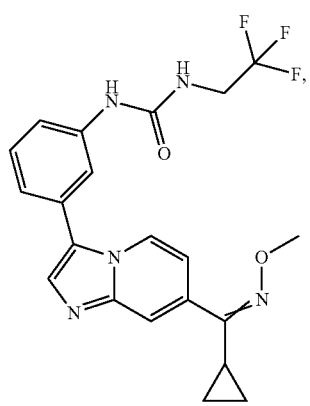 [SMILES: CON=C(c1ccn2c(-c3cccc(NC(=O)NCC(F)(F)F)c3)cnc2c1)C1CC1]
Compound 1-24
Example 1.2(6) m.p. 195° C.
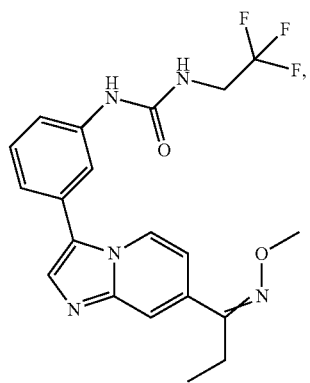 [SMILES: CCC(=NOC)c1ccn2c(-c3cccc(NC(=O)NCC(F)(F)F)c3)cnc2c1]
Compound 1-25
Example 1.2(6) m.p. 203° C.

TABLE A1-continued
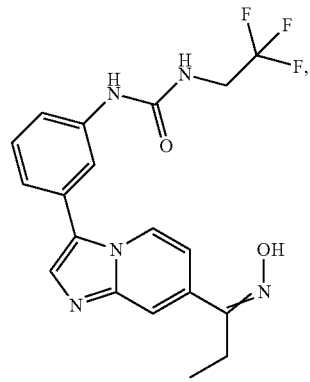 [SMILES: CCC(=NO)c1ccn2c(-c3cccc(NC(=O)NCC(F)(F)F)c3)cnc2c1]
Compound 1-26
Example 1.2(6) m.p. 232° C.
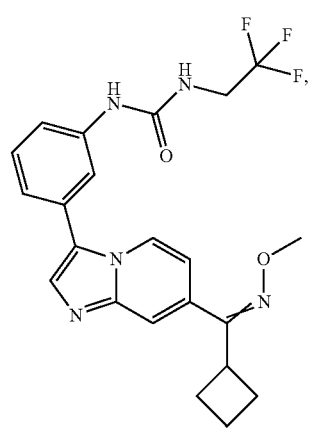 [SMILES: CON=C(c1ccn2c(-c3cccc(NC(=O)NCC(F)(F)F)c3)cnc2c1)C1CCC1]
Compound 1-27
Example 1.2(6)
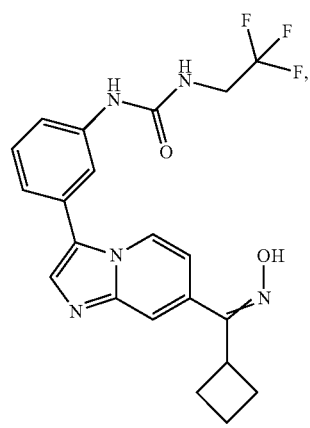 [SMILES: O=C(NCC(F)(F)F)Nc1cccc(-c2cnc3cc(C(=NO)C4CCC4)ccn23)c1]
Compound 1-28
Example 1.2(6)

TABLE A1-continued
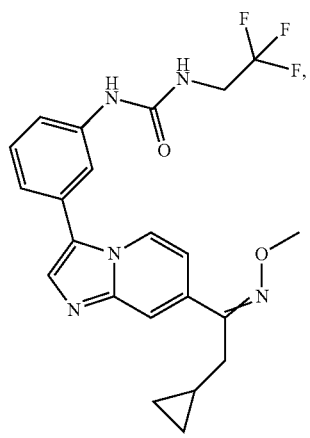 [SMILES: CON=C(CC1CC1)c1ccn2c(-c3cccc(NC(=O)NCC(F)(F)F)c3)cnc2c1]
Compound 1-29
Example 1.2(6) m.p. 234° C.
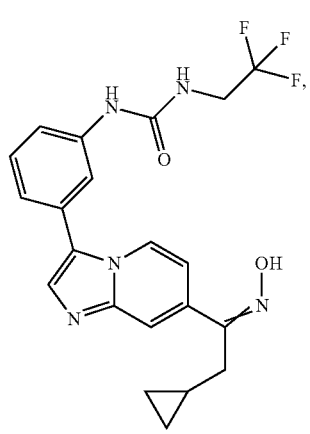 [SMILES: O=C(NCC(F)(F)F)Nc1cccc(-c2cnc3cc(C(CC4CC4)=NO)ccn23)c1]
Compound 1-30
Example 1.2(6)
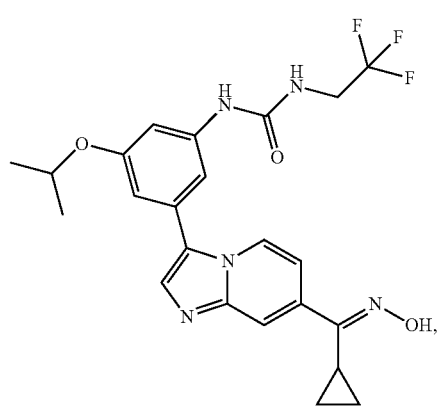 [SMILES: CC(C)Oc1cc(NC(=O)NCC(F)(F)F)cc(-c2cnc3cc(/C(=N/O)C4CC4)ccn23)c1]
Compound 1-31
Example 1.2(6) m.p. 222° C. 90:10 E:Z mixture

TABLE A1-continued
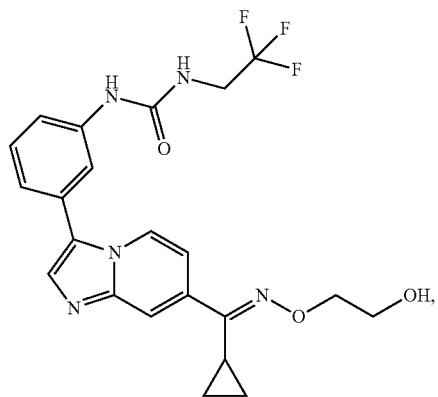 [SMILES: O=C(NCC(F)(F)F)Nc1cccc(-c2cnc3cc(/C(=N/OCCO)C4CC4)ccn23)c1]
Compound 1-32
Example 1.2(6), (E)
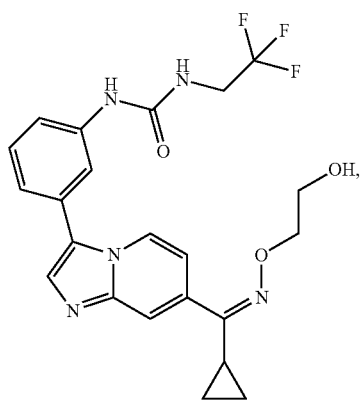 [SMILES: O=C(NCC(F)(F)F)Nc1cccc(-c2cnc3cc(/C(=N\OCCO)C4CC4)ccn23)c1]
Compound 1-33
Example 1.2(6) (Z)
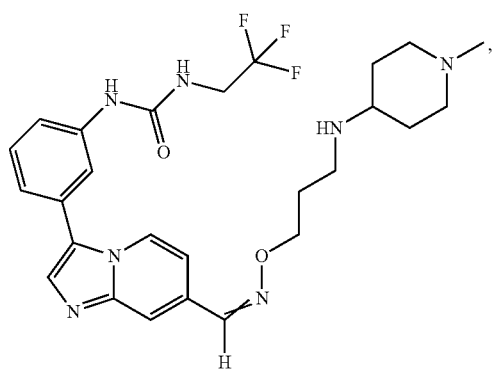 [SMILES: CN1CCC(NCCCON=Cc2ccn3c(-c4cccc(NC(=O)NCC(F)(F)F)c4)cnc3c2)CC1]
Compound 1-34
Example 1.3.a(2)

TABLE A1-continued
Compound 1-35
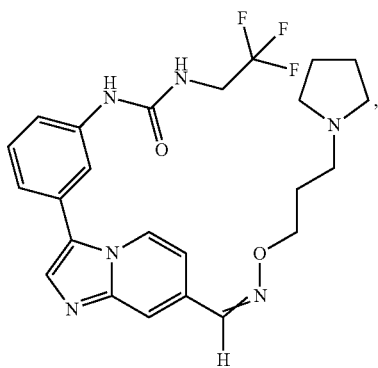 [SMILES: O=C(NCC(F)(F)F)Nc1cccc(-c2cnc3cc(C=NOCCCN4CCCC4)ccn23)c1]
Example 1.3.a(2)
Compound 1-36
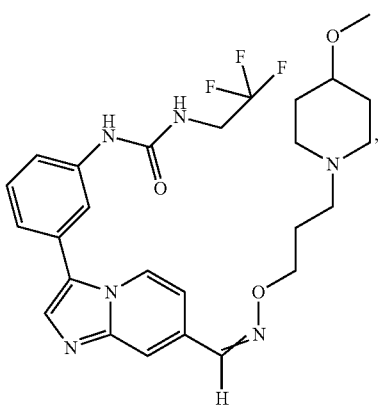 [SMILES: COC1CCN(CCCON=Cc2ccn3c(-c4cccc(NC(=O)NCC(F)(F)F)c4)cnc3c2)CC1]
Example 1.3.a(2)]
Compound 1-37
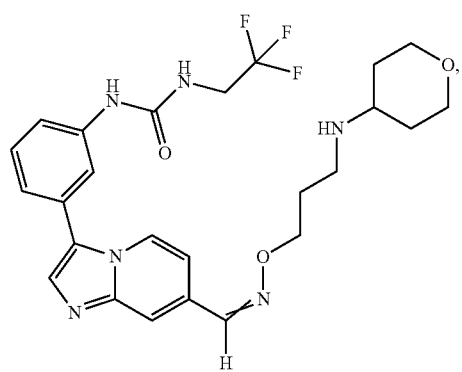 [SMILES: O=C(NCC(F)(F)F)Nc1cccc(-c2cnc3cc(C=NOCCCNC4CCOCC4)ccn23)c1]
Example 1.3.a(2)

TABLE A1-continued
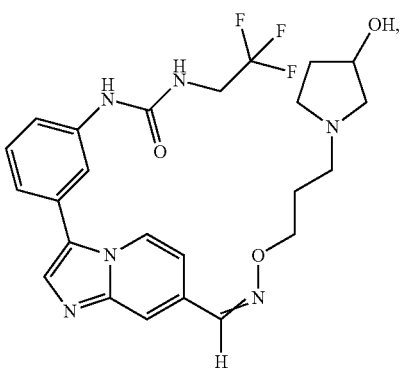 [SMILES: O=C(NCC(F)(F)F)Nc1cccc(-c2cnc3cc(C=NOCCCN4CCC(O)C4)ccn23)c1]
Compound 1-38
Example 1.3.a(2)
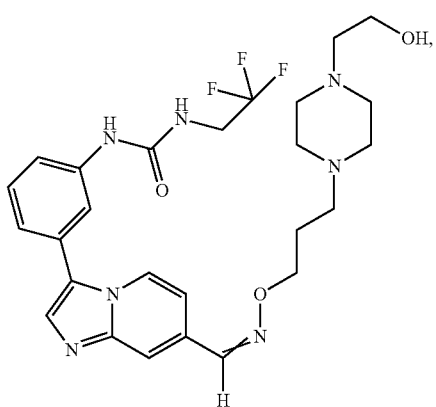 [SMILES: O=C(NCC(F)(F)F)Nc1cccc(-c2cnc3cc(C=NOCCCN4CCN(CCO)CC4)ccn23)c1]
Compound 1-39
Example 1.3.a(2)
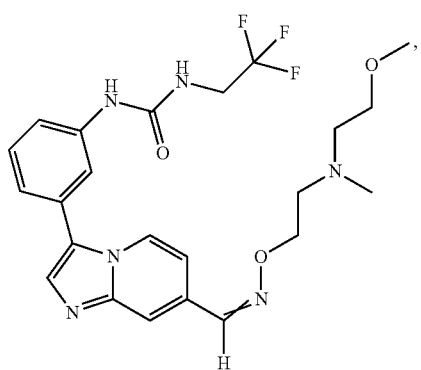 [SMILES: COCCN(C)CCON=Cc1ccn2c(-c3cccc(NC(=O)NCC(F)(F)F)c3)cnc2c1]
Compound 1-40
Example 1.3.b(2)

TABLE A1-continued
Compound 1-41
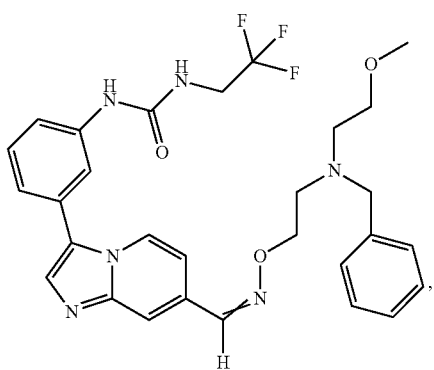 [SMILES: COCCN(CCON=Cc1ccn2c(-c3cccc(NC(=O)NCC(F)(F)F)c3)cnc2c1)Cc1ccccc1]
Example 1.3.b(2)
Compound 1-42
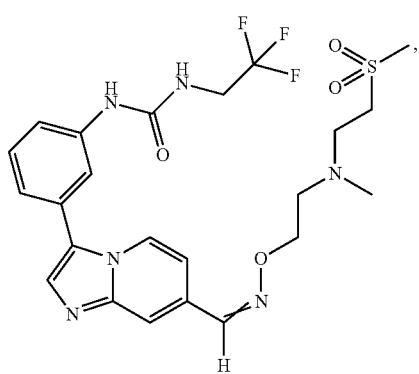 [SMILES: CN(CCON=Cc1ccn2c(-c3cccc(NC(=O)NCC(F)(F)F)c3)cnc2c1)CCS(C)(=O)=O]
Example 1.3.b(2) m.p. 193° C.
Compound 1-43
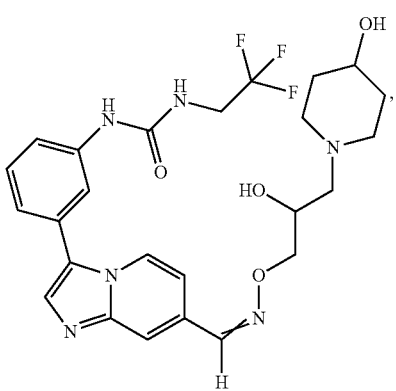 [SMILES: O=C(NCC(F)(F)F)Nc1cccc(-c2cnc3cc(C=NOCC(O)CN4CCC(O)CC4)ccn23)c1]
Example 1.6(2)

TABLE A1-continued
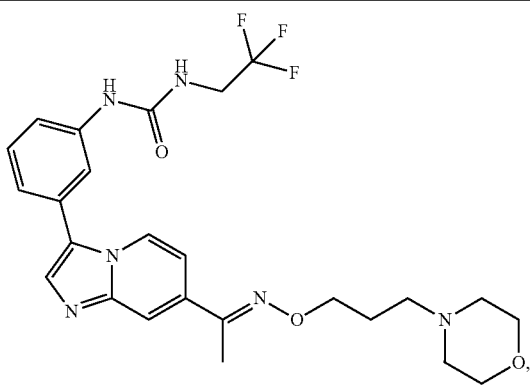
Compound 1-44
Example 1.7.b(6) (E)
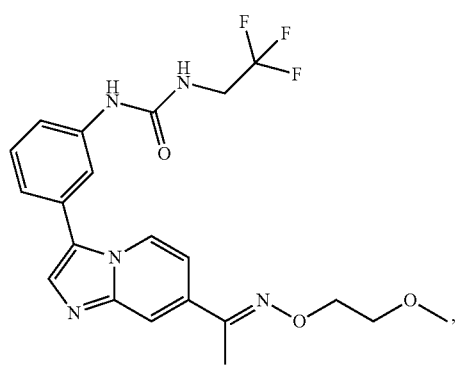 [SMILES: COCCO/N=C(\C)c1ccn2c(-c3cccc(NC(=O)NCC(F)(F)F)c3)cnc2c1]
Compound 1-45
Example 1.7.b(6) (E)
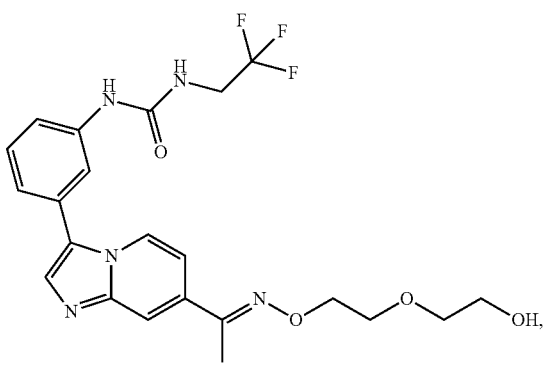 [SMILES: C/C(=N\OCCOCCO)c1ccn2c(-c3cccc(NC(=O)NCC(F)(F)F)c3)cnc2c1]
Compound 1-46
Example 1.7.b(6) (E)
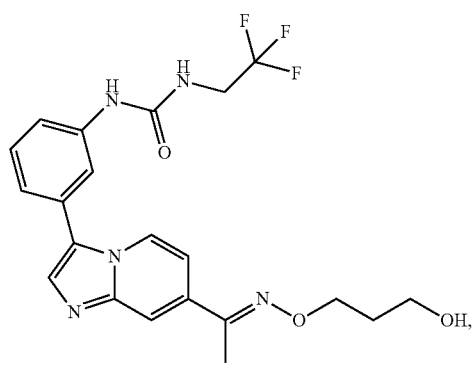 [SMILES: C/C(=N\OCCCO)c1ccn2c(-c3cccc(NC(=O)NCC(F)(F)F)c3)cnc2c1]
Compound 1-47
Example 1.7.b(6) (E)

TABLE A1-continued
Compound 1-48
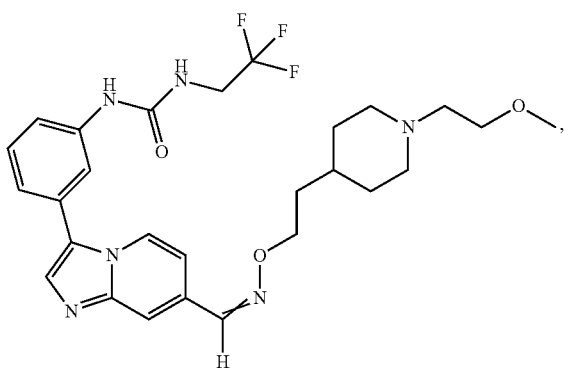 [SMILES: COCCN1CCC(CCON=Cc2ccn3c(-c4cccc(NC(=O)NCC(F)(F)F)c4)cnc3c2)CC1]
Example 1.7.c m.p. 180° C.
Compound 1-49
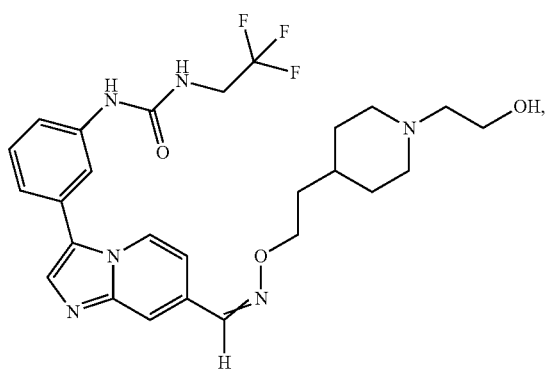 [SMILES: O=C(NCC(F)(F)F)Nc1cccc(-c2cnc3cc(C=NOCCC4CCN(CCO)CC4)ccn23)c1]
Example 1.7.c m.p. 178° C.
Compound 1-50
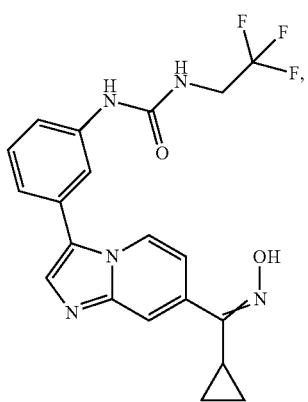 [SMILES: O=C(NCC(F)(F)F)Nc1cccc(-c2cnc3cc(C(=NO)C4CC4)ccn23)c1]
Example 1.2(6) m.p. 179° C.

TABLE A1-continued
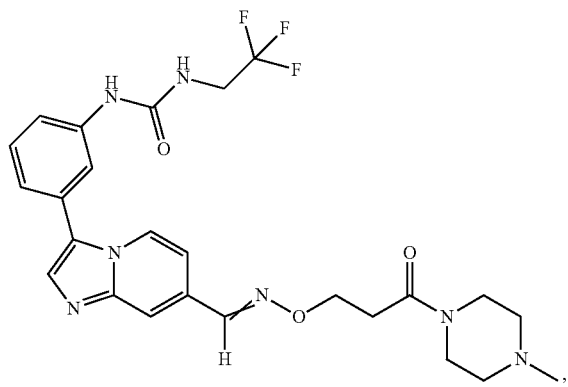 [SMILES: CN1CCN(C(=O)CCON=Cc2ccn3c(-c4cccc(NC(=O)NCC(F)(F)F)c4)cnc3c2)CC1]
Compound 1-51
Example 1.5(3) m.p. 194° C.
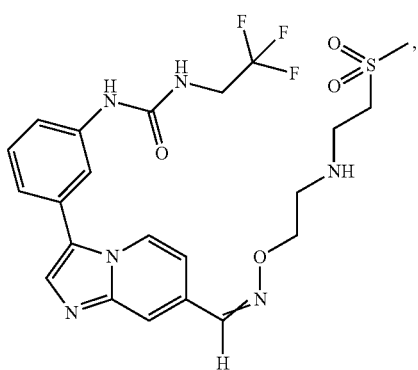 [SMILES: CS(=O)(=O)CCNCCON=Cc1ccn2c(-c3cccc(NC(=O)NCC(F)(F)F)c3)cnc2c1]
Compound 1-52
Example 1.3.c m.p. 198° C.
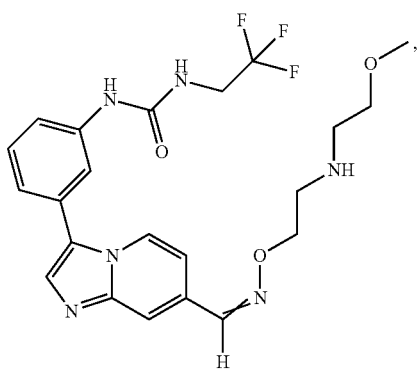 [SMILES: COCCNCCON=Cc1ccn2c(-c3cccc(NC(=O)NCC(F)(F)F)c3)cnc2c1]
Compound 1-53
Example 1.7.a(2) m.p. 172° C.
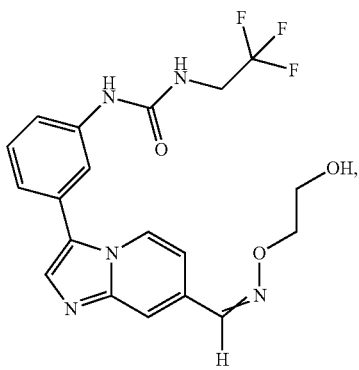 [SMILES: O=C(NCC(F)(F)F)Nc1cccc(-c2cnc3cc(C=NOCCO)ccn23)c1]
Compound 1-54
Example 1.1.a(7) m.p. 237° C.

TABLE A1-continued
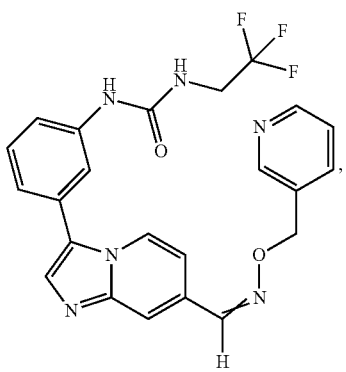
Example 1.1.b
Compound 1-55
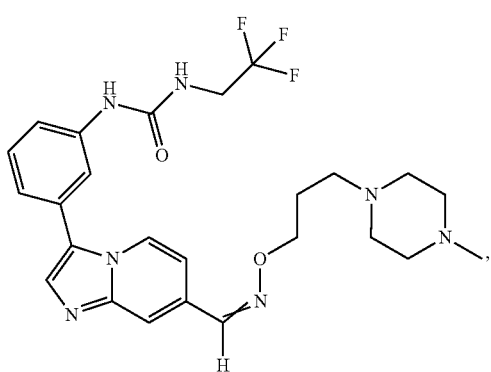 [SMILES: CN1CCN(CCCON=Cc2ccn3c(-c4cccc(NC(=O)NCC(F)(F)F)c4)cnc3c2)CC1]
Example 1.3.a(2)
Compound 1-56
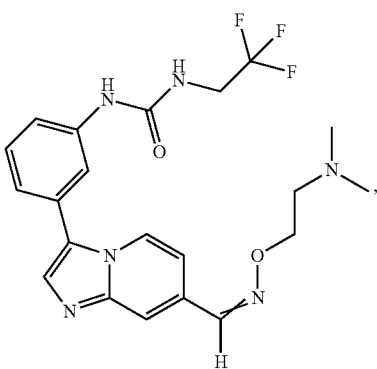 [SMILES: CN(C)CCON=Cc1ccn2c(-c3cccc(NC(=O)NCC(F)(F)F)c3)cnc2c1]
Example 1.3.b(2) m.p. 184° C.
Compound 1-57
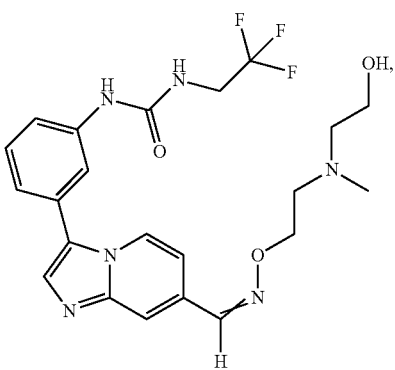 [SMILES: CN(CCO)CCON=Cc1ccn2c(-c3cccc(NC(=O)NCC(F)(F)F)c3)cnc2c1]
Example 1.3.d m.p. 185° C.
Compound 1-58

TABLE A1-continued
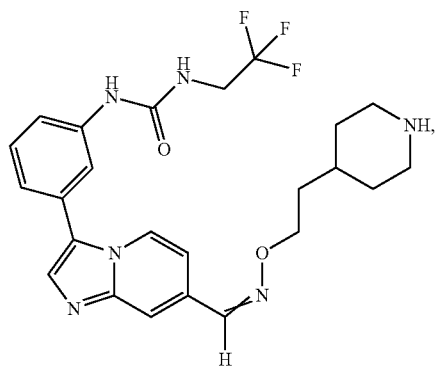 [SMILES: O=C(NCC(F)(F)F)Nc1cccc(-c2cnc3cc(C=NOCCC4CCNCC4)ccn23)c1]
Compound 1-59
Example 1.4.a(2)
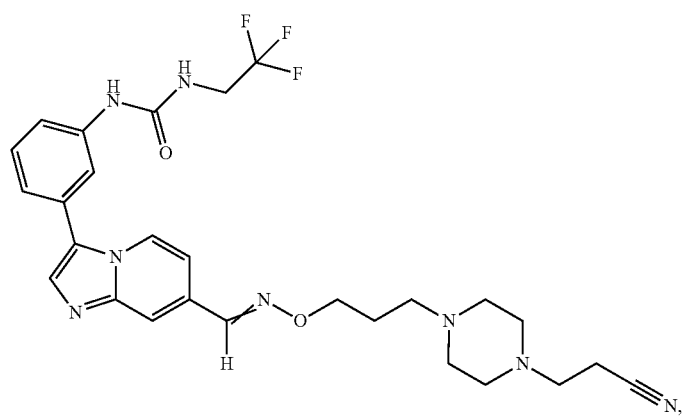 [SMILES: N#CCCN1CCN(CCCON=Cc2ccn3c(-c4cccc(NC(=O)NCC(F)(F)F)c4)cnc3c2)CC1]
Compound 1-60
Example 1.4.b(2)
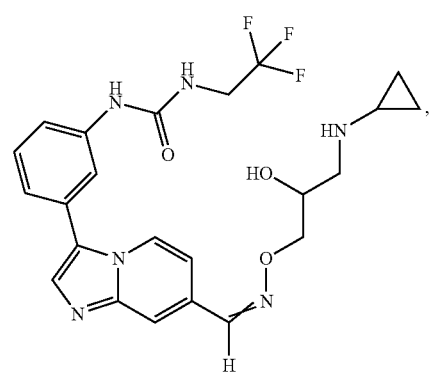 [SMILES: O=C(NCC(F)(F)F)Nc1cccc(-c2cnc3cc(C=NOCC(O)CNC4CC4)ccn23)c1]
Compound 1-61
Example 1.6(2)

TABLE A1-continued
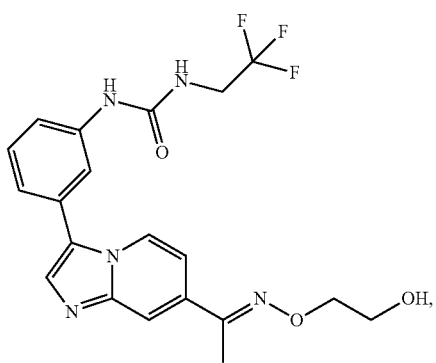 [SMILES: C/C(=N\OCCO)c1ccn2c(-c3cccc(NC(=O)NCC(F)(F)F)c3)cnc2c1]
Compound 1-62
Example 1.7.b(6) (E)
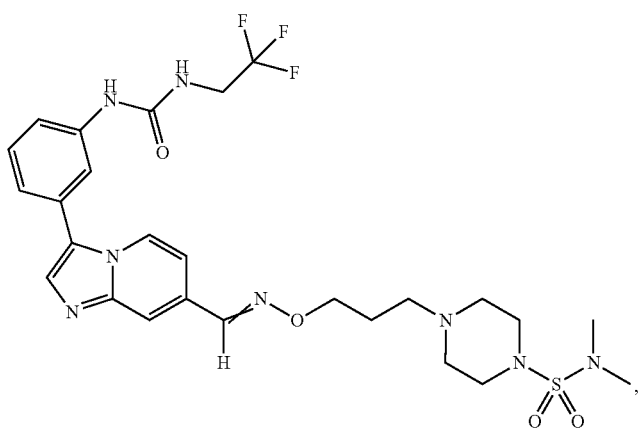 [SMILES: CN(C)S(=O)(=O)N1CCN(CCCON=Cc2ccn3c(-c4cccc(NC(=O)NCC(F)(F)F)c4)cnc3c2)CC1]
Compound 1-63
Example 1.7.c
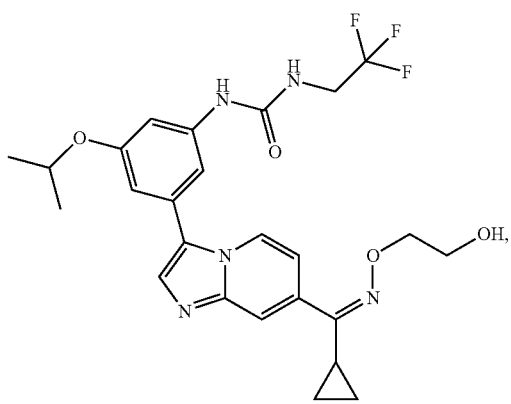 [SMILES: CC(C)Oc1cc(NC(=O)NCC(F)(F)F)cc(-c2cnc3cc(/C(=N\OCCO)C4CC4)ccn23)c1]
Compound 1-64
Example 1.10 (2) or 1.10 (5) (Z)

TABLE A1-continued

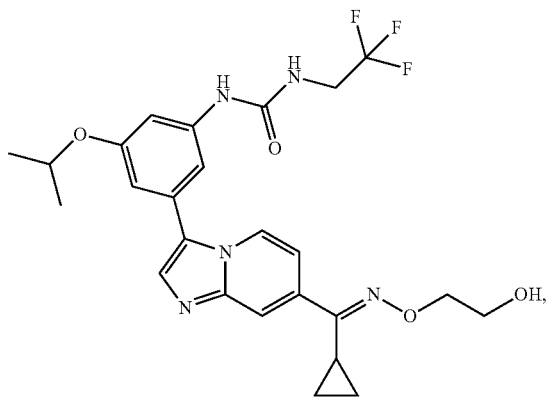 [SMILES: CC(C)Oc1cc(NC(=O)NCC(F)(F)F)cc(-c2cnc3cc(/C(=N/OCCO)C4CC4)ccn23)c1]

Compound 1-65

Example 1.10 (2) (E)

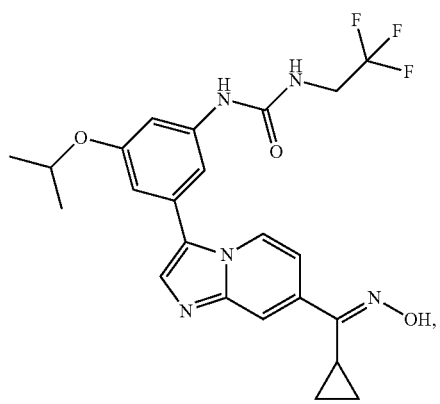 [SMILES: CC(C)Oc1cc(NC(=O)NCC(F)(F)F)cc(-c2cnc3cc(/C(=N/O)C4CC4)ccn23)c1]

Compound 1-66

Example 1.10 (3) (E)

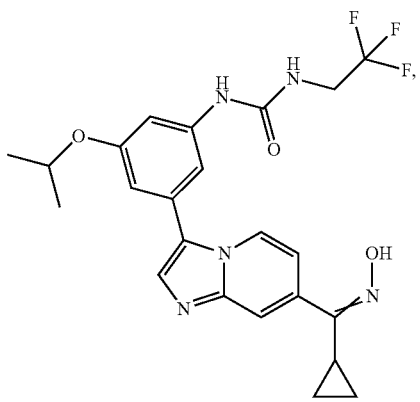 [SMILES: CC(C)Oc1cc(NC(=O)NCC(F)(F)F)cc(-c2cnc3cc(C(=NO)C4CC4)ccn23)c1]

Compound 1-67

Example 1-10 (3) (E/Z)

Analytical Part
LCMS
LCMS—General Procedure A

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS—General Procedure B

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS—General Procedure C

The LC measurement was performed using a HPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

LCMS—Procedure 1

In addition to the general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in H2O/methanol 95/5; mobile phase B: methanol) were used to run a gradient condition from 95% A and 5% B to 5% A and 95% B in 1.3 minutes and hold for 0.2 minutes. An injection volume of 0.5 μl was used.

Cone voltage was 10 V for positive ionization mode and 20 V for negative ionization mode.

LCMS—Procedure 2

In addition to the general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in H2O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used.

Cone voltage was 10 V for positive ionization mode and 20 V for negative ionization mode.

LCMS—Procedure 3

In addition to the general procedure A: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in H2O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used.

Cone voltage was 30 V for positive ionization mode and 30 V for negative ionization mode.

LCMS—Procedure 4

In addition to the general procedure B: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used.

Cone voltage was 10 V for positive ionization mode and 20 V for negative ionization mode.

LCMS—Procedure 5

In addition to the general procedure C: Reversed phase HPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

TABLE A2

Analytical data - Retention time ($R_t$ in minutes), $(MH)^+$ peak and LCMS procedure.

| Co. No. | $R_t$ | $[M + H]^+$ | LCMS Procedure |
|---|---|---|---|
| 1-33 | 0.86 | 462 | 3 |
| 1-32 | 0.83 | 462 | 3 |
| 1-31 | 3.46 | 476 | 5 |
| 1-60 | 0.81 | 557 | 2 |
| 1-29 | 1.06 | 446 | 2 |
| 1-30 | 0.87 | 432 | 2 |
| 1-28 | 0.89 | 432 | 2 |
| 1-18 | 0.77 | 436 | 2 |
| 1-47 | 0.81 | 450 | 2 |
| 1-46 | 0.79 | 480 | 2 |
| 1-17 | 0.93 | 473 | 2 |
| 1-50 | 0.8 | 418 | 2 |
| 1-24 | 0.96 | 432 | 2 |
| 1-51 | 0.74 | 532 | 2 |
| 1-52 | 0.74 | 527 | 2 |
| 1-39 | 0.71 | 548 | 2 |
| 1-14 | 1.04 | 516 | 2 |
| 1-13 | 0.89 | 486 | 2 |
| 1-12 | 0.94 | 487 | 2 |
| 1-16 | 0.83 | 490 | 2 |
| 1-15 | 1 | 458 | 2 |
| 1-55 | 0.86 | 469 | 2 |
| 1-11 | 1.03 | 432 | 2 |
| 1-63 | 0.94 | 611 | 2 |
| 1-53 | 0.72 | 479 | 2 |
| 1-10 | 0.72 | 475 | 2 |
| 1-52 | 0.75 | 527 | 2 |
| 1-21 | 1.12 | 392 | 1 |
| 1-22 | 0.96 | 406 | 2 |
| 1-21 | 0.78 | 392 | 2 |
| 1-62 | 0.78 | 436 | 2 |
| 1-58 | 0.7 | 479 | 2 |
| 1-57 | 0.7 | 449 | 2 |
| 1-59 | 0.74 | 489 | 2 |
| 1-42 | 0.82 | 541 | 2 |
| 1-48 | 0.8 | 547 | 2 |
| 1-44 | 0.88 | 519 | 2 |
| 1-45 | 0.92 | 450 | 2 |
| 1-34 | 0.66 | 532 | 1 |
| 1-49 | 0.73 | 533 | 2 |
| 1-35 | 0.72 | 489 | 2 |
| 1-36 | 0.78 | 533 | 2 |
| 1-37 | 0.71 | 519 | 2 |

TABLE A2-continued

Analytical data - Retention time ($R_t$ in minutes), $(MH)^+$ peak and LCMS procedure.

| Co. No. | $R_t$ | $[M + H]^+$ | LCMS Procedure |
|---|---|---|---|
| 1-38 | 0.69 | 505 | 2 |
| 1-21 | 0.76 | 392 | 2 |
| 1-56 | 0.73 | 518 | 2 |
| 1-53 | 0.72 | 479 | 2 |
| 1-59 | 0.74 | 489 | 2 |
| 1-8 | 1.14 | 508 | 2 |
| 1-9 | 0.92 | 489 | 2 |
| 1-59 | 0.72 | 489 | 2 |
| 1-20 | 0.77 | 472 | 2 |
| 1-6 | 0.86 | 469 | 2 |
| 1-7 | 4.31 | 466 | 4 |
| 1-41 | 5.95 | 569 | 4 |
| 1-5 | 0.76 | 456 | 2 |
| 1-40 | 0.79 | 493 | 2 |
| 1-61 | 0.74 | 491 | 2 |
| 1-4 | 0.85 | 469 | 2 |
| 1-54 | 0.75 | 422 | 2 |
| 1-43 | 0.66 | 535 | 2 |
| 1-1 | 0.96 | 440 | 2 |
| 1-3 | 0.82 | 505 | 2 |
| 1-2 | 0.87 | 480 | 2 |
| 1-64 | 0.94 | 520 | 3 |
| 1-65 | 0.97 | 520 | 3 |

1H-NMR (360 MHz, DMSO-d6)

Compound 1-64

1H-NMR (360 MHz, DMSO-d6): 9.05 (s, 1H), 8.59 (d, 1H), 7.92 (s, 1H), 7.89 (s, 1H), 7.28-7.21 (m, 3H), 6.97 (t, 1H), 6.83 (s, 1H), 4.78-4.57 (m, 2H), 4.19 (t, 2H), 4.09-3.95 (m, 4H), 3.68-3.60 (m, 2H), 1.97-1.87 (m, 1H), 1.35 (d, 6H), 0.97-0.83 (m, 4H).

Compound 1-65

1H-NMR (360 MHz, DMSO-d6): 9.06 (s, 1H), 8.58 (d, 1H), 7.86 (s, 1H), 7.83 (s, 1H), 7.27-7.20 (m, 3H), 6.96(t, 1H), 6.82 (s, 1H), 4.84-4.78 (m, 1H), 4.73 (dt, 1H), 4.19 (t, 2H), 4.08-3.95 (m, 2H), 3.78-3.70 (m, 2H), 2.18-2.08 (m, 1H), 1.35 (d, 6H), 1.13-1.03 (m, 2H), 0.86-0.76 (m, 2H).

Biological Assays

FGFR3, VEGFR2 and PDGFR in vitro Kinase Inhibitory Activity Assays

Enzymes (from Upstate), prepared at 2× final concentration, were incubated with test compounds, biotinylated Flt3 substrate (biotin-VASSDNEYFYVDF) (Cell Signalling Technology Inc.) and ATP in the appropriate assay buffer (Table 1). The reaction was allowed to proceed for 3 hours (FGFR3), 1 hour (VEGFR2, PDGFR-beta) at room temperature on a plate shaker at 700 rpm before being stopped with 35 mM EDTA, pH 8 (FGFR3, VEGFR2) or 55 mM EDTA, pH 8 (PDGFR-beta). 5× detection mix (50 mM HEPES pH 7.5, 0.1% BSA, 11.34 nM Eu-anti-pY (PY20) (PerkinElmer) 74 nM SA-XL665 (Cisbio) for FGFR3, 50 mM HEPES, pH 7.5, 0.1% BSA, 11.34 nM Eu-anti-pY (PY20), 187.5 nM SA-XL665 for VEGFR2 and 50 mM HEPES, pH 7.5, 0.1% BSA, 11.34 nM Eu-anti-pY (PT66) (PerkinElmer), 375 nM SA-XL665 (Cisbio) for PDGFR-beta) was then added to each well and the plate sealed and incubated at room temperature for one hour on a plate shaker at 700 rpm. The plate was then read on a Packard Fusion plate reader or a BMG Pherastar both in TRF mode.

TABLE 1

Final assay conditions for FGFR3, VEGFR2 and PDGFR-beta assays

| Enzyme | 1 × Assay Buffer | Flt3 substrate concentration | ATP concentration |
|---|---|---|---|
| FGFR3 | A | 0.125 μM | 8 μM |
| VEGFR2 | B | 0.5 μM | 0.5 μM |
| PDGFR-beta | C | 1 μM | 70 μM |

Kinase Assay buffers were:
A: 50 mM HEPES pH 7.5, 6 mM $MnCl_2$, 1 mM DTT, 0.01% TritonX-100
B: 50 mM HEPES pH 7.5, 6 mM $MnCl_2$, 1 mM DTT, 0.01% TritonX-100, 0.1 mM Sodium orthovanadate
C: 20 mM HEPES pH 7.5, 10 mM $MnCl_2$, 0.01% Triton X-100, 1 mM DTT, 0.1 mM Sodium orthovanadate FGFR3 and VEGFR2 Data for the compounds of the invention in the above assays are provided in Table A3.

FGFR1, FGFR2, FGFR4, VEGFR1 and VEGFR31 In vitro Kinase Inhibitory Activity Assays The inhibitory activity against FGFR1, FGFR2, FGFR4, VEGFR1 and VEGFR3 can be determined at Upstate Discovery Ltd. Enzymes are prepared at 10× final concentration in enzyme buffer (20 mM MOPS, pH 7.0, 1 mM EDTA, 0.1% B-mercaptoethanol, 0.01% Brij-35, 5% glycerol, 1 mg/ml BSA). Enzymes are then incubated in assay buffer with various substrates and $^{33}$P-ATP (~500 cpm/μmol) as described in the table.

The reaction is initiated by the addition of Mg/ATP. The reaction is allowed to proceed for 40 minutes at room temperature before being stopped with 5 μl of a 3% phosphoric acid solution. Ten μl of the reaction mix is transferred to either a filtermatA or P30 filtermat and washed three times in 75 mM phosphoric acid and once in methanol before being dried for scintillation counting.

Compounds are tested at the concentrations of the assay reagents as detailed below in duplicate against all kinases and the percent activity compared to control is calculated. Where inhibition is high an $IC_{50}$ can be determined.

| Enzyme | Assay Buffer | Substrate | ATP Concentration (μM) |
|---|---|---|---|
| FGFR1 | A | 250 μM KKKSPGEYVNIEFG | 200 μM |
| FGFR2 | B | 0.1 mg/ml poly(Glu, Tyr) 4:1 | 90 μM |
| FGFR4 | C | 0.1 mg/ml poly(Glu, Tyr) 4:1 | 155 μM |
| VEGFR1 | A | 250 μM KKKSPGEYVNIEFG | 200 μM |
| VEGFR3 | A | 500 μM GGEEEEYFELVKKKK | 200 μM |

Enzyme buffer A: 8 mM MOPS, pH 7.0, 0.2 mM EDTA, 10 mM MgAcetate
Enzyme buffer B: 8 mM MOPS, pH 7.0, 0.2 mM EDTA, 2.5 mM MnCl2, 10 mM MgAcetate
Enzyme buffer C: 8 mM Mops, pH 7.0, 0.2 mM EDTA, 10 mM MnCl2, 10 mM MgAcetate.

Cell-Based pERK ELISA Method

LP-1 or JIM-1 multiple myeloma cells were seeded in 96 well plates at $1 \times 10^6$ cells/ml in 200 ul per well in serum free media. HUVEC cells were seeded at $2.5 \times 10^5$ cells/ml and allowed to recover for 24 h prior to transfer to serum free media. Cells were incubated for 16 h at 37° C. prior to the addition of a test compound for 30 minutes. Test compounds were administered at a 0.1% final DMSO concentration. Following this 30 minute incubation a FGF-1/Heparin (FGF-1 at 100 ng/ml final and Heparin at 100 ug/ml) mixture or $VEGF^{165}$ (100 ug/ml) was added to each of the wells for a further 5 minutes. The media was removed and 50 ul ERK ELISA lysis buffer (R and D Systems DuoSet ELISA for pERK and Total ERK #DYC-1940E, DYC-1018E) added. ELISA plates and standards were prepared according o the standard DuoSet protocols and the relative amounts of pERK to total ERK in each sample calculated according to the standard curve.

In particular, compounds of the invention were tested against the LP-1 cell line (DSMZ no.: ACC 41) derived from human multiple myeloma.

HUVEC Cell Based Selectivity Assays

HUVEC cells are seeded in 6 well plates at $1 \times 10^6$ cells/well and allowed to recover for 24 h. They are transferred to serum free media for 16 hours prior to treatment with test compound for 30 minutes in 0.1% DMSO final. Following compound incubation FGF-1 (100 ng/ml) and Heparin (100 ug/ml) or VEGF[165] (100 ng/ml) are added for 5 minutes. Media is removed, cells washed with ice-cold PBS and lysed in 100 ul TG lysis buffer (20 mM Tris, 130 nM NaCl, 1% Triton-X-100, 10% Glycerol, protease and phosphatase inhibitors, pH 7.5). Samples containing equivalent amounts of protein are made up with LDS sample buffer and run on SDS PAGE followed by western blotting for a number of downstream VEGFR and FGFR pathway targets including phospho-FGFR3, phospho-VEGFR2 and phospho-ERK1/2. The western blot can then be analysed by visual inspection or densitometry.

Ba/F3-TEL-FGFR3 & Ba/F3 (WT) Cell Proliferation Assays

Stably transfected Ba/F3-TEL-FGFR3 cells were plated out into black 96-well tissue culture plates with clear bottoms in RPMI medium containing 10% FBS and 0.25 mg/ml G418 at a density of $5 \times 10^3$ cells/well (200 µl per well). The parental wild-type Ba/F3 cells (DSMZ no.: ACC 300) were plated out into black 96-well tissue culture plates with clear bottoms in RPMI medium containing 10% FBS and 2 ng/ml mouse IL-3 (R&D Systems) at a density of $2.5 \times 10^3$ cells/well (200 µl per well). Plates were placed in an incubator overnight before adding the compounds the following day. Dilutions of compounds were made in DMSO starting at 10 mM and were diluted into the wells to give a final DMSO concentration of 0.1% in assay. Compounds were left on the cells for 72 hours before the plates were removed from the incubator and 20 µl of Alamar Blue™ (Biosource) was added to each well. Plates were placed in the incubator for 4-6 hours before reading plates at 535 nm (excitation)/590 nm (emission) on a Fusion plate reader (Packard). Where inhibition is high an $IC_{50}$ can be determined.

Data for the compounds of the invention in the above assays are provided in Table A3.

In Vivo Models of Hypertension

A number of animal models exist to measure the potential hypertensive effects of small molecule inhibitors. They can be classified into two main types; indirect and direct measurements. The most common indirect method is the cuff technique. Such methods have the advantages of being non-invasive and as such can be applied to a larger group of experimental animals however the process allows only intermittent sampling of blood pressure and requires the animal to be restrained in some way. Application of restraint can stress the animal and means that changes in blood pressure attributable to a specific drug effect can be hard to pick up.

Direct methodologies include those that make use of radio telemetry technology or via indwelling catheters connected to externally mounted transducers. Such methods require a high level of technical expertise for the initial surgery involved in implantation and costs involved are high. However a key advantage is that they allow continuous monitoring of blood pressure without restraint over the time period of the experiment. These methods are reviewed in Kurz et al (2005), Hypertension. 45, 299-310.

hERG Activity

The activity of compound of formula (I) against the hERG $K^+$ ion channel can be determined using the assay described in the article by M. H. Bridgland-Taylor et al., *Journal of Pharmacological and Toxicological Methods*, 54 (2006), 189-199. This IonWorks™ HT hERG screening assay is performed commercially by Upstate (Millipore) using the PrecisION™ hERG-CHO cell line.

Determination of Potency against Cytochrome P450

The potency of the compound of formula (I) against cytochrome P450 (CYP450) enzymes 1A2, 2C9, 2C19, 3A4 and 2D6 can be determined using the Pan Vera Vivid CYP450 screening kits available from invitrogen (Paisley, UK). The CYP450s are supplied in the form of baculosomes containing the CYP450 and NADPH reductase and the substrates used are the fluorescent Vivid substrates. The final reaction mixtures are as follows:

1A2

100 mM potassium phosphate, pH 8, 1% acetonitrile, 2 µM 1A2 Blue vivid substrate, 100 µM $NADP^+$, 4 nM CYP450 1A2, 2.66 mM glucose-6-phosphate, 0.32 U/ml glucose-6-phosphate dehydrogenase.

2C9

50 mM potassium phosphate, pH 8, 1% acetonitrile, 2 µM Green vivid substrate, 100 µM $NADP^+$, 8 nM CYP450 2C9, 2.66 mM glucose-6-phosphate, 0.32 U/ml glucose-6-phosphate dehydrogenase.

2C19

50 mM potassium phosphate, pH 8, 1% acetonitrile, 8 µM Blue vivid substrate, 100 µM $NADP^+$, 4 nM CYP450 2C19, 2.66 mM glucose-6-phosphate, 0.32 U/ml glucose-6-phosphate dehydrogenase.

3A4

100 mM potassium phosphate, pH 8, 1% acetonitrile, 10 µM 3A4 Blue vivid substrate, 100 µM $NADP^+$, 2.5 nM CYP450 3A4, 2.66 mM glucose-6-phosphate, 0.32 U/ml glucose-6-phosphate dehydrogenase.

2D6

100 mM potassium phosphate, pH 8, 1% acetonitrile, 5 µM 2D6 Blue vivid substrate, 100 µM $NADP^+$, 16 nM CYP450 2D6, 2.66 mM glucose-6-phosphate, 0.32 U/ml glucose-6-phosphate dehydrogenase.

Fluorescence is monitored for 20 minutes at 30 second intervals on a Molecular Devices Gemini fluorescence plate reader. The excitation and emission wavelengths are 390 nm and 460 nm for 1A2, 2C19 and 3A4, 390 nm and 485 nm for 2D6 and 485 nm and 530 nm for 2C9. Initial rates are determined from progress curves.

The test compound is made up in methanol or acetonitirile and tested against the CYP450s at a concentration of 10 µM.

TABLE A3

| Co. No. | FGFR3 IC50(µM) or % I | VEGFR2 IC50(µM) or % I | BaF3 WT prolif (µM) | BaF3-TEL-FGFR3 prolif (µM) |
|---|---|---|---|---|
| 1-3 | 0.0180 | 0.682 | 2.8 | 0.31 |
| 1-2 | 0.0190 | 0.885 | 1.6 | 0.29 |
| 1-1 | 0.0194 | 0.635 | 0.31 | 0.21 |

TABLE A3-continued

| Co. No. | FGFR3 IC50(μM) or % I | VEGFR2 IC50(μM) or % I | BaF3 WT prolif (μM) | BaF3-TEL-FGFR3 prolif (μM) |
|---|---|---|---|---|
| 1-54 | 0.0210 | 0.620 | 0.51 | 0.5 |
| 1-61 | 0.0290 | 0.440 | 30.0% at 3.00 μM | 0.93 |
| 1-43 | 0.0240 | 0.520 | 0.000% at 10.0 μM | 6.6 |
| 1-40 | 0.0280 | 0.720 | | |
| 1-4 | 0.0140 | 0.230 | 5.3 | 0.26 |
| 1-7 | 0.0185 | 0.584 | 20.0% at 3.00 μM | 0.42 |
| 1-41 | 0.0551 | 1.79 | 5.9 | 0.86 |
| 1-5 | 0.0313 | 0.877 | 10.0% at 10.0 μM | 2.3 |
| 1-56 | 0.0190 | 0.380 | 3 | 0.32 |
| 1-20 | 0.00710 | 0.360 | | |
| 1-6 | 0.0130 | 0.480 | | |
| 1-8 | 0.215 | >10.0 | 0.828 | 0.0175 |
| 1-9 | 0.0140 | 0.680 | | |
| 1-34 | 0.0380 | 0.260 | 0.000% at 10.0 μM | 60.0% at 10.0 μM |
| 1-35 | 0.0230 | 0.330 | 28.0% at 3.00 μM | 0.56 |
| 1-36 | 0.0240 | 0.360 | 34.0% at 3.00 μM | 0.38 |
| 1-37 | 0.0280 | 0.270 | 43.0% at 10.0 μM | 3.5 |
| 1-48 | 0.0230 | 0.400 | 1.8 | 0.6 |
| 1-49 | 0.0190 | 0.330 | 36.0% at 3.00 μM | 1.4 |
| 1-21 | 0.00190 | 0.0300 | 17.0% at 10.0 μM | 0.046 |
| 1-22 | 0.00510 | 0.0920 | | |
| 1-62 | 0.00350 | 0.0510 | 45.0% at 10.0 μM | 0.11 |
| 1-44 | 0.00380 | 0.0590 | | |
| 1-59 | 0.0240 | 0.330 | 11.0% at 10.0 μM | 42.0% at 3.00 μM |
| 1-57 | 0.0290 | 0.470 | 30.0% at 3.00 μM | 0.25 |
| 1-42 | 0.0170 | 0.540 | 10.0% at 10.0 μM | 1.3 |
| 1-58 | 0.0290 | 0.340 | 55.0% at 10.0 μM | 0.78 |
| 1-39 | 0.0250 | 0.390 | 47.0% at 3.00 μM | 1.3 |
| 1-38 | 0.0260 | 0.390 | 21.0% at 10.0 μM | 1.8 |
| 1-63 | 0.0160 | 0.500 | 45.0% at 3.00 μM | 0.31 |
| 1-11 | 0.0270 | 46.0% at 1 μM | 0.88 | 0.6 |
| 1-12 | 0.0180 | 0.540 | 38.0% at 10.0 μM | 0.24 |
| 1-13 | 0.0300 | 0.660 | 46.0% at 1.00 μM | 0.3 |
| 1-14 | 0.0270 | 0.680 | 43.0% at 3.00 μM | 0.56 |
| 1-55 | 0.00770 | 0.380 | 51.0% at 3.00 μM | 0.14 |
| 1-15 | 0.0260 | 0.980 | 4.6 | 0.043 |
| 1-45 | 0.00410 | 0.0680 | 4 | 0.048 |
| 1-10 | 0.0190 | 0.270 | 2.8 | 0.14 |
| 1-53 | 0.0350 | 0.810 | 13 | 0.48 |
| 1-52 | 0.0260 | 0.730 | 25.0% at 10.0 μM | 4.9 |
| 1-51 | 0.0330 | 0.880 | 27.0% at 10.0 μM | 2.2 |
| 1-16 | 0.0180 | 0.610 | 19.0% at 10.0 μM | 1.3 |
| 1-24 | 0.0150 | 0.230 | 38.0% at 1.00 μM | 0.26 |
| 1-50 | 0.00970 | 0.230 | 62.0% at 10.0 μM | 0.3 |
| 1-25 | 0.0110 | 0.240 | 46.0% at 3.00 μM | 0.32 |
| 1-26 | 0.00450 | 0.0830 | 40.0% at 10.0 μM | 0.12 |
| 1-17 | 0.0130 | 0.660 | 4.1 | 0.23 |
| 1-46 | 0.00310 | 0.0680 | 39.0% at 10.0 μM | 0.032 |
| 1-47 | 0.00230 | 0.0510 | 63.0% at 10.0 μM | 0.000% at 10.0 μM |
| 1-18 | 0.0190 | 0.400 | 4.7 | 0.24 |
| 1-27 | 0.0800 | 1.20 | 1.5 | 1.3 |
| 1-28 | 0.0220 | 0.330 | 43.0% at 3.00 μM | 0.57 |
| 1-29 | 0.0590 | >1.00 | 16.0% at 10.0 μM | 28.0% at 10.0 μM |
| 1-30 | 0.0190 | 0.290 | 20.0% at 10.0 μM | 43.0% at 10.0 μM |
| 1-19 | 0.0230 | 0.670 | 5.2 | 2.4 |
| 1-60 | 0.0220 | 0.560 | 0.000% at 1.00 μM | 85.0% at 1.00 μM |
| 1-31 | 0.0230 | 1.34 | 6.2 | 0.47 |
| 1-32 | 0.0720 | 0.960 | 50.0% at 10.0 μM | 1.1 |
| 1-33 | 0.0180 | 0.180 | 11 | 0.25 |
| 1-64 | 0.030 | 1.2 | | 0.5 |
| 1-66 | 0.023 | 1.4 | 6.2 | 0.47 |

The invention claimed is:

1. A compound of formula (I):

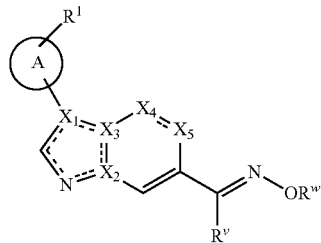

wherein $X_1$, $X_2$ and $X_3$ are each independently selected from carbon or nitrogen, such that at least one of $X_1$-$X_3$ represents nitrogen;

$X_4$ represents $CR^3$, nitrogen, NH or C=O;

$X_5$ represents $CR^6$, nitrogen, NH or C=O;

provided that no more than three of $X_1$-$X_5$ represent nitrogen;

------ represents a single or double bond, such that when $X_5$ represents C=O, $X_4$ and $X_5$ are joined by a single bond and such that at least one bond within the 5 membered ring system is a double bond;

$R^3$ represents hydrogen, halogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkenyl, cyano, halo$C_{1-6}$ alkyl, halo$C_{1-6}$ alkoxy, amino, or —$C_{1-6}$alkylamino;

$R^6$ represents halogen, hydrogen, $C_{1-6}$ alkyl, $C_{1-6}$ alkoxy, $C_{2-6}$ alkenyl, $C_{2-6}$ alkynyl, —C≡N, $C_{3-8}$ cycloalkyl, $C_{3-8}$ cycloalkenyl, —NHSO$_2$R$^w$, —CH=N—OR$^w$, or a 3-6 membered monocyclic heterocyclyl group wherein said $C_{1-6}$ alkyl, $C_{2-6}$ alkenyl, $C_{2-6}$ alkynyl, $C_{1-6}$ alkoxy and heterocyclyl groups may be optionally substituted by one or more $R^a$ groups;

A represents an aromatic or non-aromatic carbocyclyl or heterocyclyl group which may be optionally substituted by one or more (e.g. 1, 2 or 3) $R^a$ groups;

$R^1$ represents —NHCONR$^4$R$^5$, —NHCOOR$^4$, —NH—CO—(CH$_2$)$_n$—NR$^4$R$^5$, —NH—(CH$_2$)$_n$—CONR$^4$R$^5$, —NH—CO—(CH$_2$)$_n$—COOR$^4$, —NH—CO—(CH$_2$)$_n$—CSOR$^4$, —NHSO$_2$R$^4$, —NHSO$_2$NR$^4$R$^5$, —NHCSNR$^4$R$^5$, —NHCOR$^4$, —NHCSR$^4$, —NHCSSR$^4$, —NHC(=NR$^4$)NR$^4$R$^5$, —NHC(=N—CN)NR$^4$R$^5$, —NHC(=NR$^4$)R$^5$, —NH—C(=NH)—NH—CO—R$^4$, —NHCSOR$^4$, —NHCOSR$^4$ or an NH-heterocyclyl group wherein the heterocyclyl group represents thiadiazolyl or oxadiazolyl and the heterocyclyl group may be optionally substituted by one or more (e.g. 1, 2 or 3) $R^a$ groups;

$R^4$ and $R^5$ independently represent hydrogen, $C_{1-6}$ alkyl, $C_{2-6}$ alkenyl, $C_{2-6}$ alkynyl, $C_{3-8}$ cycloalkyl, $C_{3-8}$ cycloalkenyl, $C_{1-6}$ alkanol, halo$C_{1-6}$ alkyl, —(CH$_2$)$_n$—NR$^x$R$^y$, —(CH$_2$)$_s$—COOR$^z$, —(CH$_2$)$_n$—O—(CH$_2$)$_m$—OH, —(CH$_2$)$_n$-aryl, —(CH$_2$)$_n$—O-aryl, —(CH$_2$)$_n$-heterocyclyl or —(CH$_2$)$_n$—O-heterocyclyl wherein said $C_{1-6}$ alkyl, $C_{2-6}$ alkenyl, $C_{2-6}$ alkynyl, $C_{3-8}$ cycloalkyl, $C_{3-8}$ cycloalkenyl, aryl and heterocyclyl groups may be optionally substituted by one or more (e.g. 1, 2 or 3) $R^a$ groups;

$R^x$, $R^y$ and $R^z$ independently represent hydrogen, $C_{1-6}$ alkyl, $C_{2-6}$ alkenyl, $C_{2-6}$ alkynyl, $C_{1-6}$ alkanol, —COOC$_{1-6}$ alkyl, hydroxy, $C_{1-6}$ alkoxy, halo$C_{1-6}$ alkyl, —(CH$_2$)$_n$—OH, —(CH$_2$)$_n$—O—C$_{1-6}$alkyl, —CO—(CH$_2$)$_n$—C$_{1-6}$ alkoxy, —(CH$_2$)$_s$—CN, —C$_{1-6}$ alkylamino, —C$_{1-6}$ alkyl-N(C$_{1-6}$ alkyl)$_2$, —C$_{1-6}$ alkyl-NH (C$_{1-6}$ alkyl), —(CH$_2$)$_s$—C$_{3-8}$ cycloalkyl, amino, -aminoC$_{1-6}$ alkyl, -amino(C$_{1-6}$ alkyl)$_2$, —(CH$_2$)$_s$—NH—SO$_2$—N(C$_{1-6}$alkyl)$_q$, —(CH$_2$)$_s$—N(C$_{1-4}$alkyl)-SO$_2$—N(C$_{1-6}$alkyl)$_q$, —(CH$_2$)$_s$—O—C(=O)—C$_{1-4}$ alkyl-N(C$_{1-6}$alkyl)$_q$, —(CH$_2$)$_s$—C$_{3-8}$ cycloalkenyl, or when attached to nitrogen or carbon atom R$^x$ and R$^y$ can form a ring;

R$^a$ represents halogen, C$_{1-6}$ alkyl, C$_{2-6}$ alkenyl, C$_{2-6}$ alkynyl, C$_{3-8}$ cycloalkyl, C$_{3-8}$ cycloalkenyl, —OR$^x$, —(CH$_2$)$_n$—O—R$^x$, —O—(CH$_2$)$_n$—OR$^x$, haloC$_{1-6}$ alkyl, haloC$_{1-6}$ alkoxy, C$_{1-6}$ alkanol, =O, =S, nitro, —Si(R$^x$)$_4$, —(CH$_2$)$_s$—CN, —S—R$^x$, —SO—R$^x$, —SO$_2$—R$^x$, —COR$^x$, aryl, heterocyclyl group, —(CR$^x$R$^y$)$_s$—COOR$^z$, —(CR$^x$R$^y$)$_s$—CONR$^x$R$^y$, —(CH$_2$)$_s$—NR$^x$R$^y$, —(CH$_2$)$_s$—NR$^x$COR$^y$, —(CH$_2$)$_s$—NR$^x$—(CH$_2$)$_s$—SO$_2$—R$^y$, —NR$^x$—(CH$_2$)$_s$—R$^z$, —(CH$_2$)$_s$—O—C(=O)—C$_{1-4}$alkyl-NR$^x$R$^y$, —(CH$_2$)$_s$—NR$^x$—(CH$_2$)$_n$—O—C(=O)—R$^z$, —(CR$^x$R$^y$)—O—C(=O)—R$^z$, —(CH$_2$)$_s$—NH—SO$_2$—NR$^x$R$^y$, —OCONR$^x$R$^y$, —(CH$_2$)$_s$—NR$^x$CO$_2$R$^y$, —O—(CH$_2$)$_s$—CR$^x$R$^y$—(CH$_2$)$_t$—OR$^z$, —(CH$_2$)$_s$—SO$_2$NR$^x$R$^y$ or —NH—C(=NH)—NH$_2$ groups; wherein said C$_{1-6}$ alkyl, C$_{2-6}$ alkenyl, C$_{2-6}$ alkynyl, C$_{3-8}$ cycloalkyl, C$_{3-8}$ cycloalkenyl, aryl and heterocyclyl groups may be optionally substituted by one or more R$^x$ groups;

R$^b$ represents a -Q-R$^a$ group or a —Y-carbocyclyl or —Z-heterocyclyl group wherein said carbocyclyl and heterocyclyl groups may be optionally substituted by one or more (e.g. 1, 2 or 3) R$^a$ groups;

Y and Z independently represent a direct bond, —CO—(CR$^x$R$^y$)$_s$—, —(CR$^x$R$^y$)$_s$—CO—, —COO, —(CR$^x$R$^y$)$_n$—, —NR$^x$—(CR$^x$R$^y$)$_s$—, —(CR$^x$R$^y$)$_s$—NR$^x$—, —CONR$^x$—, —NR$^x$CO—, —SO$_2$NR$^x$—, —NR$^x$SO$_2$—, —NR$^x$CONR$^y$—, —NR$^x$CSNR$^y$—, —O—(CR$^x$R$^y$)$_s$—, —(CR$^x$R$^y$)$_s$—O—, S—, —SO— or —(CR$^x$R$^y$)$_s$—SO$_2$—;

Q represents NR$^x$, S(O)$_q$ or a direct bond;

m and n independently represent an integer from 1-4;

s and t independently represent an integer from 0-4;

q represents an integer from 0-2;

and wherein (a) R$^v$ represents hydrogen or R$^b$; and
R$^w$ represents —(CH$_2$)$_n$—O—R$^x$, —(CH$_2$)$_s$—NR$^x$R$^Y$, —(CH$_2$)$_s$—NR$^x$—(CH$_2$)$_s$—SO$_2$R$^y$, or a —Z-heterocyclyl group wherein said heterocyclyl group may be optionally substituted by one or more (e.g. 1, 2 or 3) R$^a$ groups; or (b) R$^v$ represents a —Y-carbocyclyl group wherein said carbocyclyl group may be optionally substituted by one or more (e.g. 1, 2 or 3) R$^a$ groups; and
R$^w$ represents hydrogen, C$_{1-6}$alkyl, or —(CH$_2$)$_n$—O—R$^x$; or a pharmaceutically acceptable salt, tautomer, N-oxide or solvate thereof.

2. A compound as defined in claim 1 wherein A represents a phenyl group optionally substituted by one or more R$^a$ groups, or a pharmaceutically acceptable salt, tautomer, N-oxide or solvate thereof.

3. A compound as defined in claim 1 wherein A represents a phenyl group optionally substituted at the 3-position by one R$^a$ group, or a pharmaceutically acceptable salt, tautomer, N-oxide or solvate thereof.

4. A compound as defined in claim 3 wherein A represents unsubstituted phenyl, or a pharmaceutically acceptable salt, tautomer, N-oxide or solvate thereof.

5. A compound as defined in claim 1 wherein R$^1$ represents —NHCONR$^4$R$^5$, or a pharmaceutically acceptable salt, tautomer, N-oxide or solvate thereof.

6. A compound as defined in claim 5 wherein R$^1$ represents —NHCONHCH$_2$CF$_3$, or a pharmaceutically acceptable salt, tautomer, N-oxide or solvate thereof.

7. A compound as defined in claim 1 wherein R$^v$ represents hydrogen and R$^w$ represents:
—(CH$_2$)$_n$—O—R$^x$;
—(CH$_2$)$_s$—NR$^x$R$^y$; or
—(CH$_2$)$_s$—NR$^x$—(CH$_2$)$_s$—SO$_2$R$^y$, or a pharmaceutically acceptable salt, tautomer, N-oxide or solvate thereof.

8. A compound as defined in claim 1 wherein R$^v$ represents hydrogen and R$^w$ represents a —Z-heterocyclyl group wherein said heterocyclyl group may be optionally substituted by one or more (e.g. 1, 2 or 3) R$^a$ groups, or a pharmaceutically acceptable salt, tautomer, N-oxide or solvate thereof.

9. A compound as defined in claim 8 wherein Z represents a direct bond, —(CR$^x$R$^y$)$_n$, —(CR$^x$R$^y$)$_s$—NR$^x$ or —(CR$^x$R$^y$)$_s$—CO—, or a pharmaceutically acceptable salt, tautomer, N-oxide or solvate thereof.

10. A compound as defined in claim 8 wherein said heterocyclyl group is substituted by one or more C$_{1-6}$alkyl, —O—R$^x$, —(CH$_2$)$_n$—O—R$^x$, —(CH$_2$)$_s$—SO$_2$—NR$^x$R$^y$, —(CH$_2$)$_s$NR$^x$R$^y$ or —NH—C(=NH)—NH$_2$ group, or a pharmaceutically acceptable salt, tautomer, N-oxide or solvate thereof.

11. A compound as defined in claim 8 wherein R$^w$ is —(CR$^x$R$^y$)$_n$-heterocyclyl, wherein the heterocyclyl group is a nitrogen containing heterocyclyl group, or a pharmaceutically acceptable salt, tautomer, N-oxide or solvate thereof.

12. A compound as defined in claim 1 wherein:
(i) R$^v$ and R$^w$ independently represent C$_{1-6}$alkyl, —(CH$_2$)$_n$—O—R$^x$ or —(CH$_2$)$_n$—O—C$_{1-6}$alkyl, or
(ii) R$^v$ represents -Q-R$^a$ wherein Q represents a direct bond and R$^a$ represents C$_{1-6}$alkyl and R$^w$ represents a —Z-heterocyclyl group wherein said heterocyclyl group may be optionally substituted by one or more (e.g. 1, 2 or 3) R$^a$ groups, or
(iii) R$^v$ represents a —Y-carbocyclyl group and R$^w$ represents hydrogen, or
(iv) R$^v$ represents a —Y—C$_{3-6}$ cycloalkyl group and R$^w$ represents hydrogen, or
(v) R$^v$ represents a —Y-carbocyclyl group and R$^w$ represents C$_{1-6}$alkyl or —(CH$_2$)$_n$—O—R$^x$, or a pharmaceutically acceptable salt, tautomer, N-oxide or solvate thereof.

13. A compound as defined in claim 12 wherein Z represents —(CR$^x$R$^y$)$_n$, or Y is a direct bond or —(CR$^x$R$^y$)$_n$—, or a pharmaceutically acceptable salt, tautomer, N-oxide or solvate thereof.

14. A compound as defined in claim 1 wherein X$_1$-X$_5$ are as defined by the following ring system:

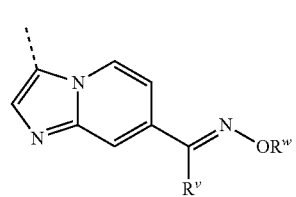

(j)

or a pharmaceutically acceptable salt, tautomer, N-oxide or solvate thereof.

15. A compound as defined in claim 1 which is a compound selected from:
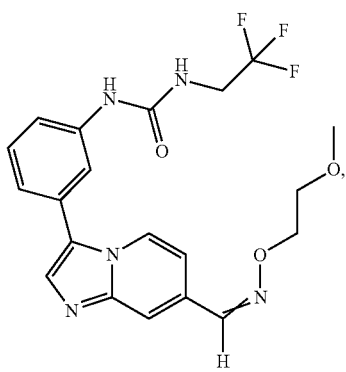
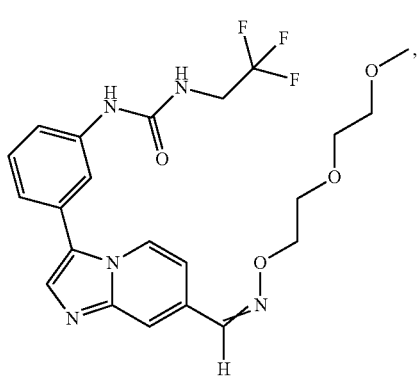
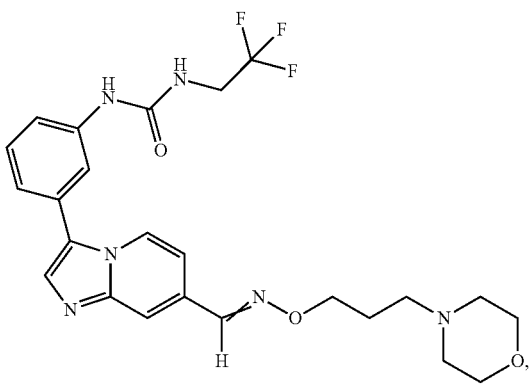
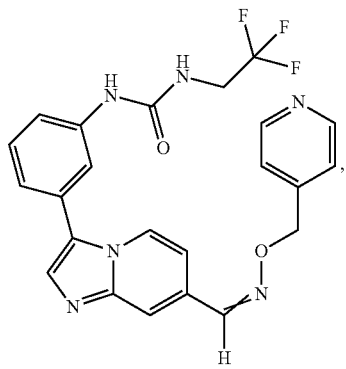
-continued
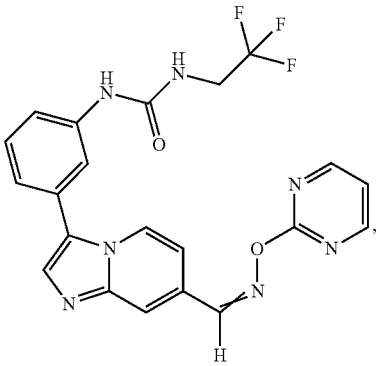
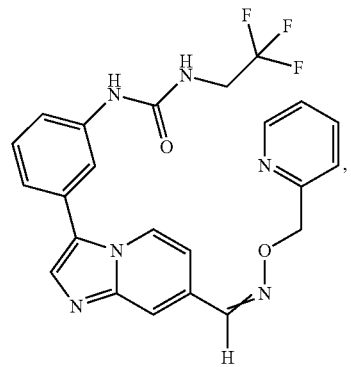
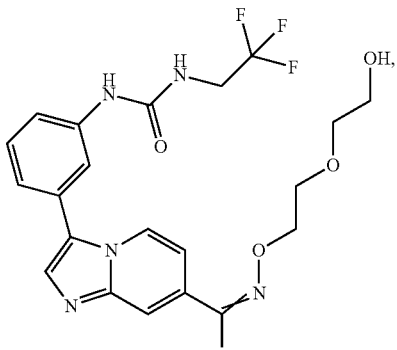
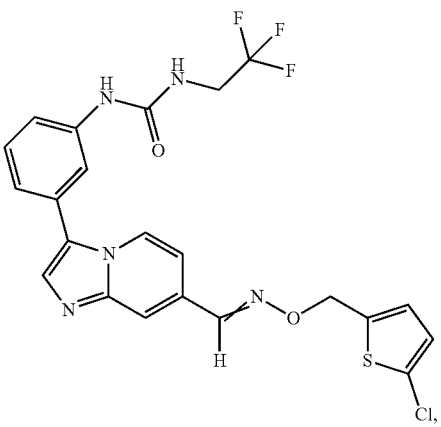

159
-continued
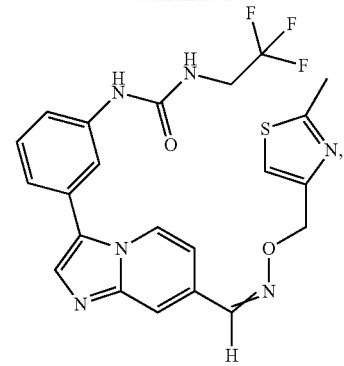
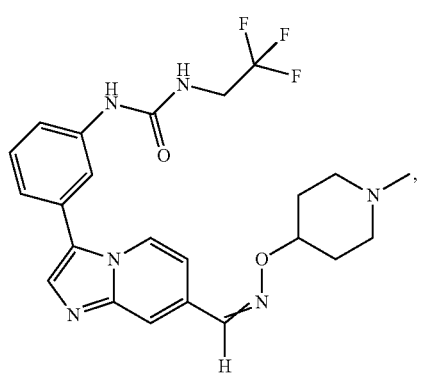
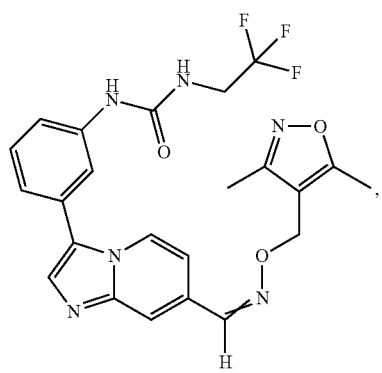
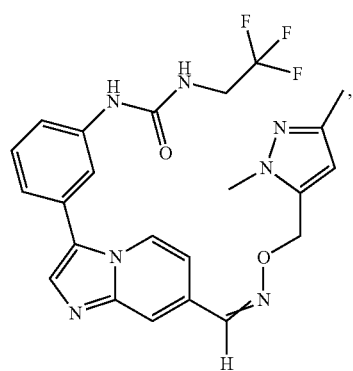
160
-continued
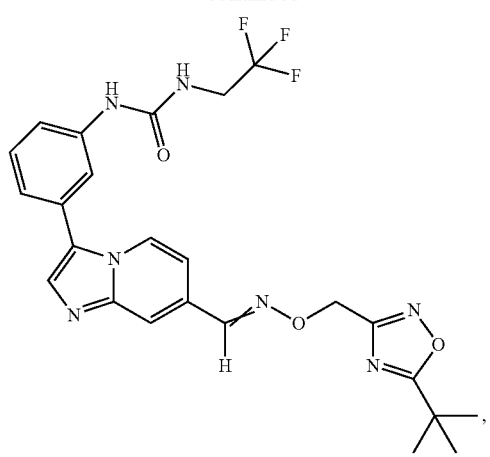
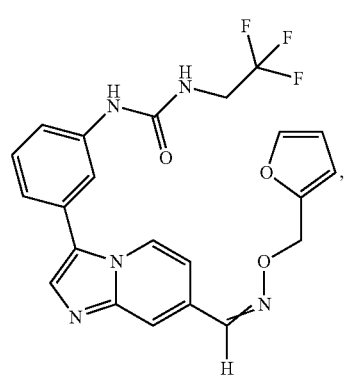
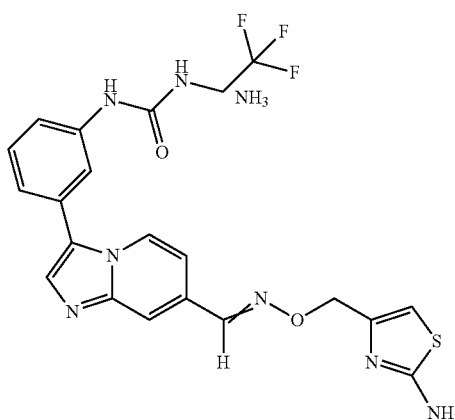
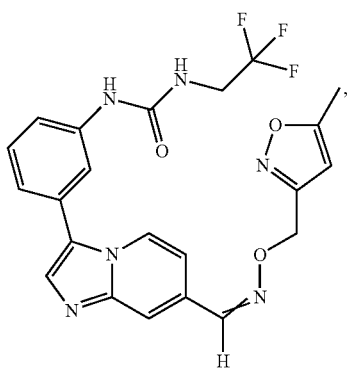

161
-continued
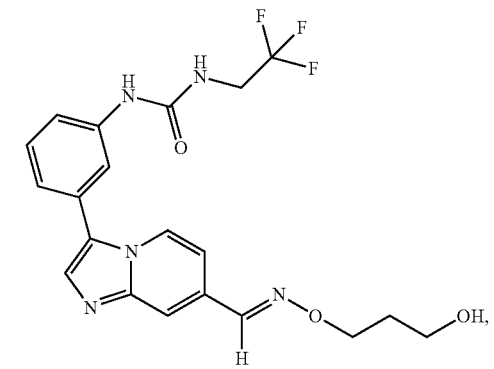
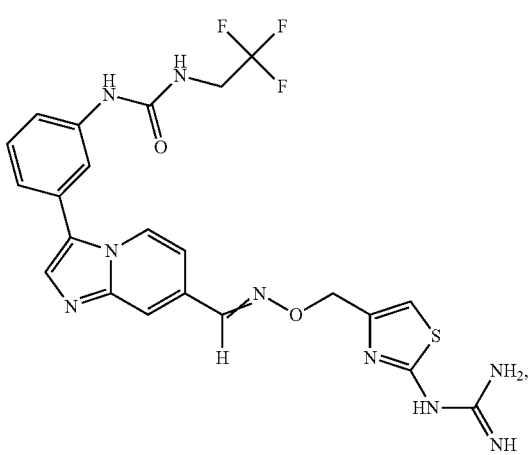
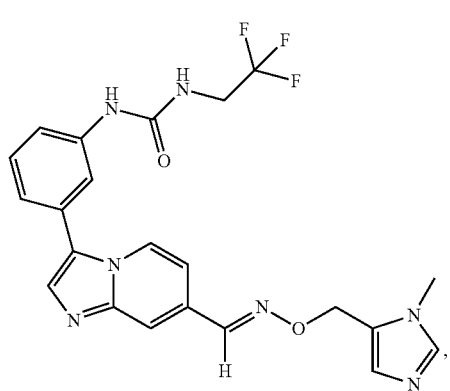
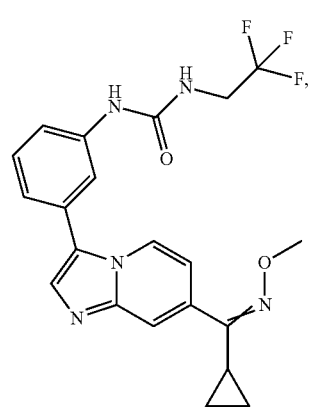
162
-continued
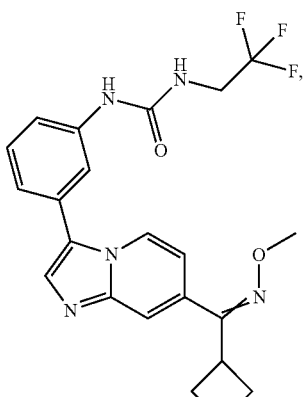
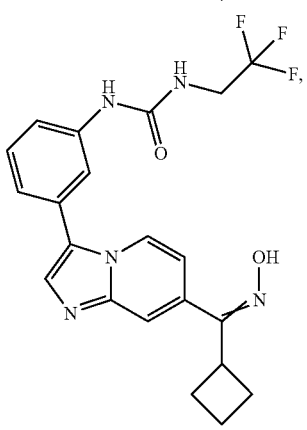
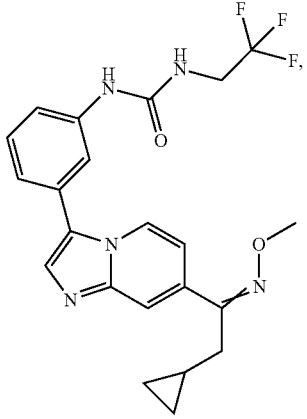
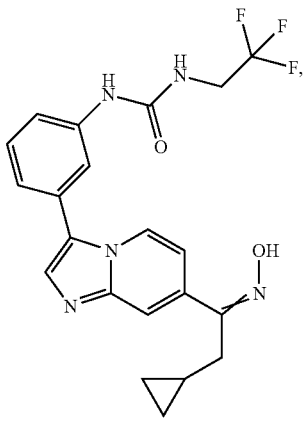

163
-continued
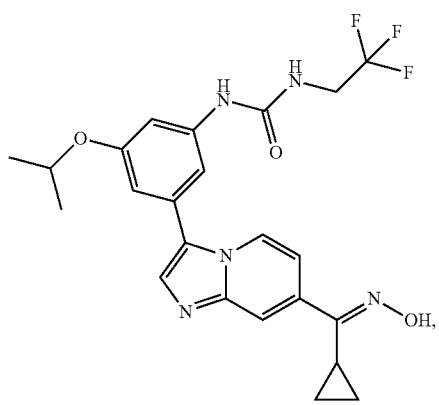
164
-continued
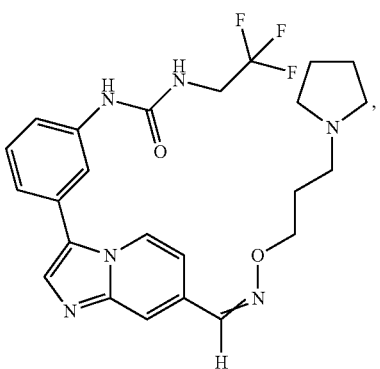
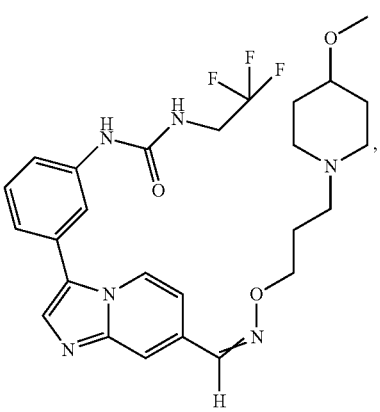
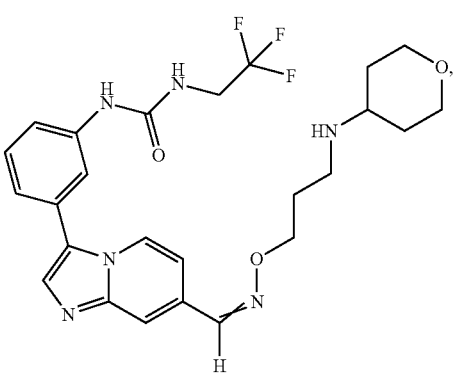
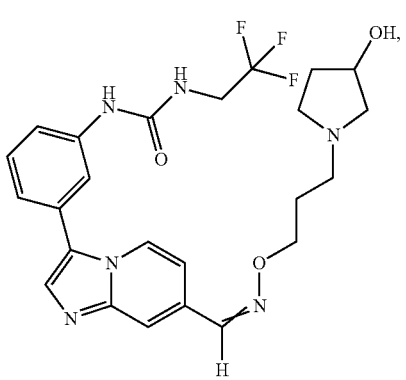

165
-continued
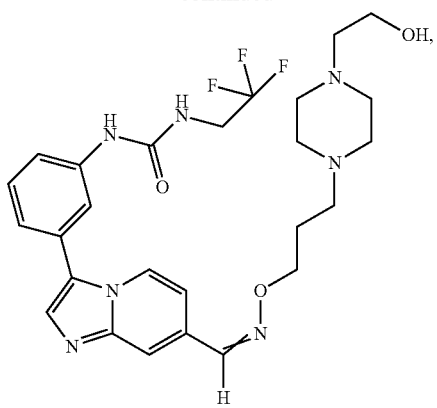
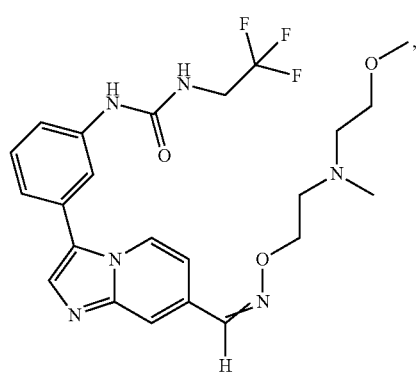
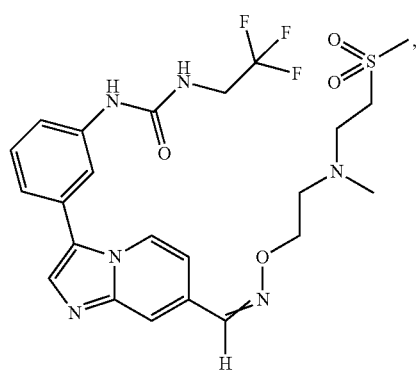
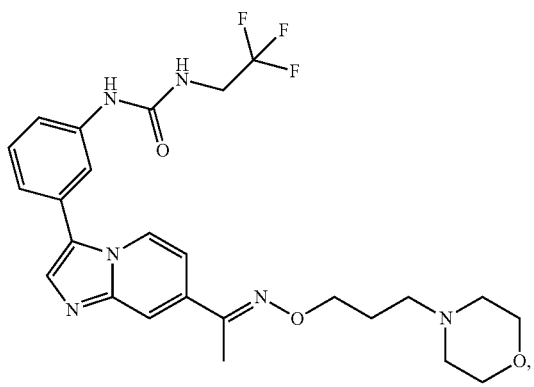
166
-continued
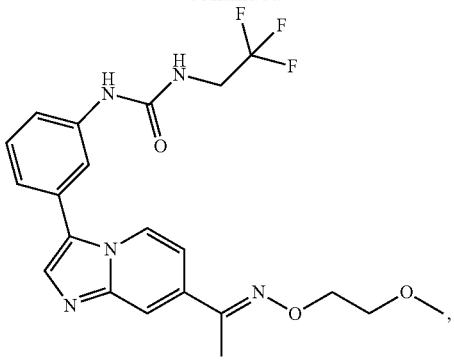
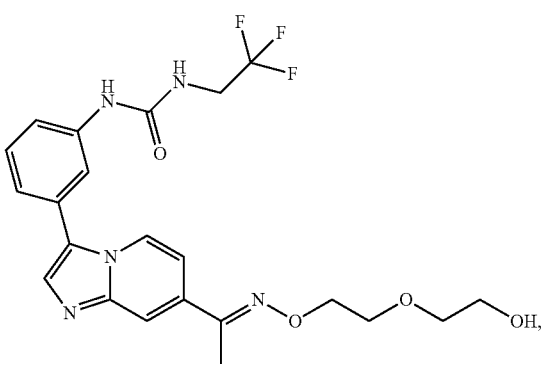
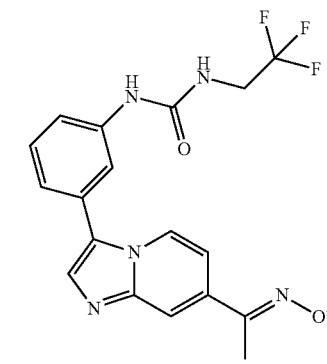
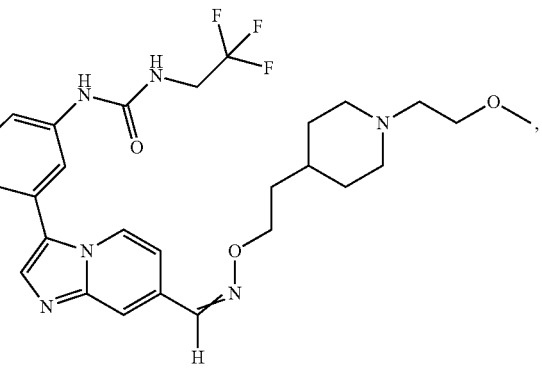

167
-continued

168
-continued

169
-continued
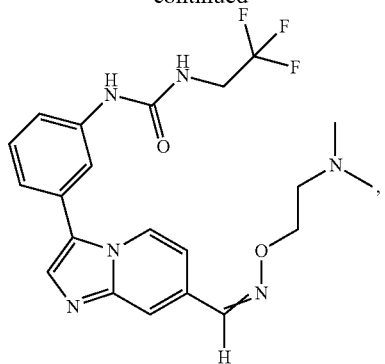
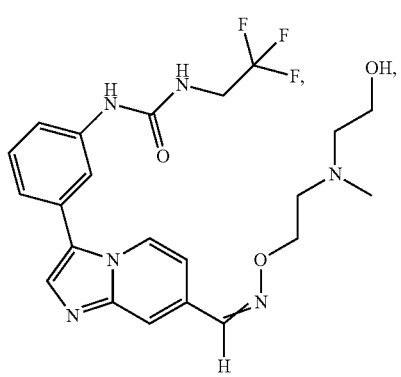
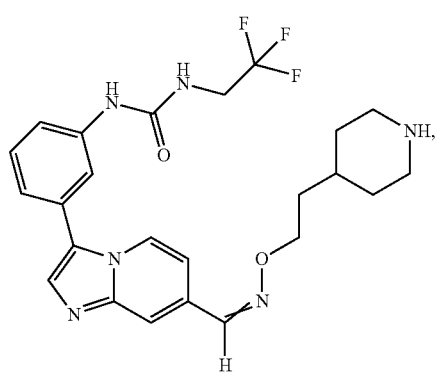
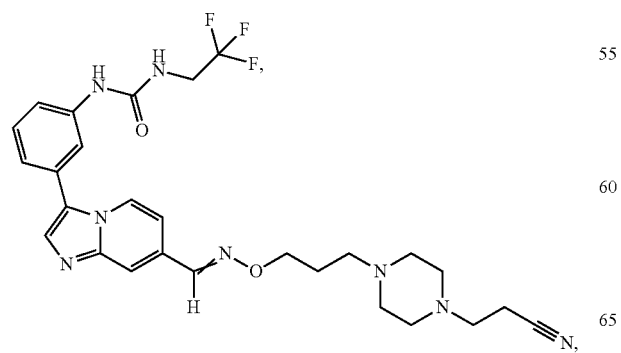
170
-continued
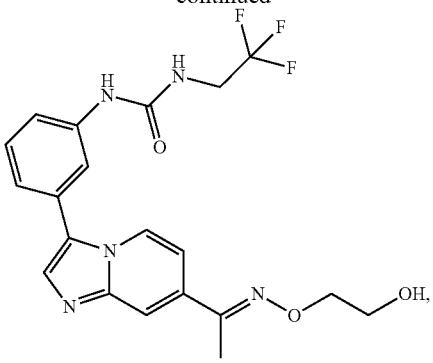
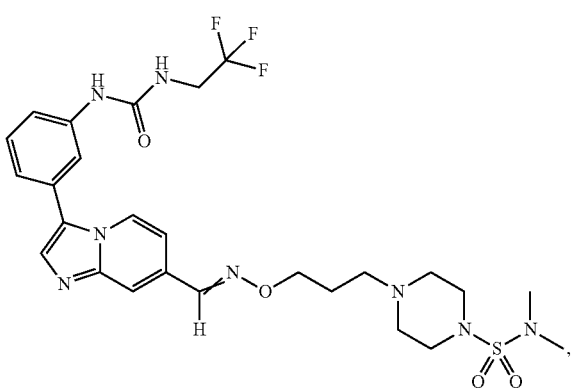
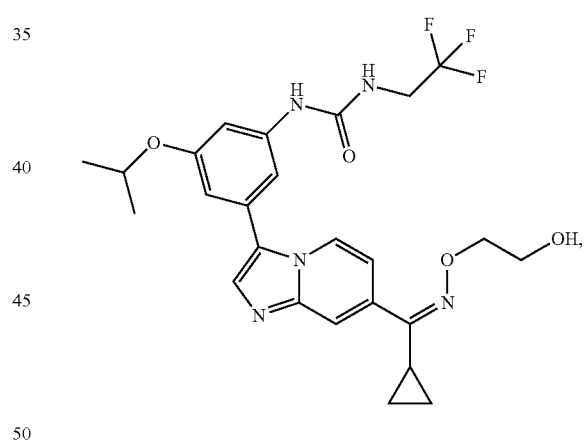
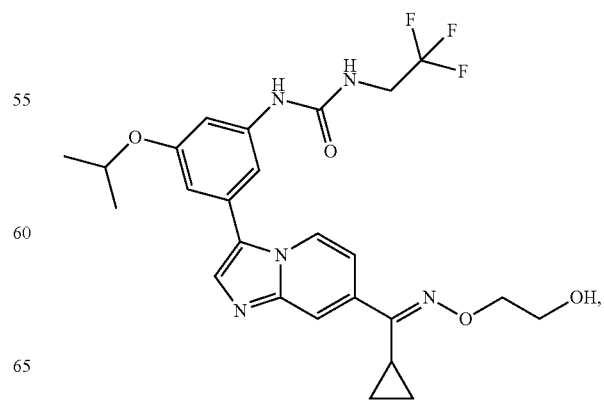

-continued

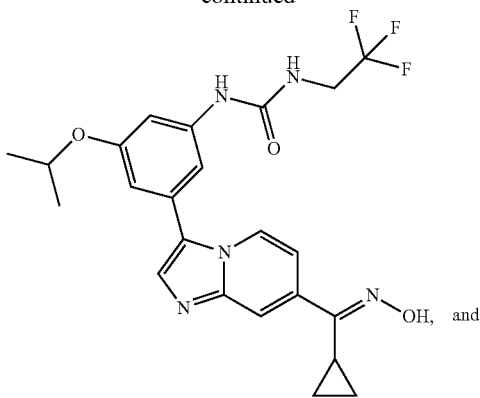
and

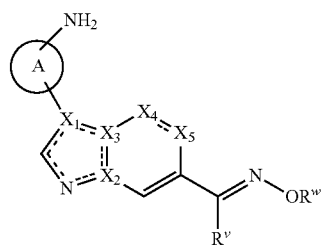

or a pharmaceutically acceptable salt, tautomer, N-oxide or solvate thereof.

16. A compound as defined in claim 1 or a pharmaceutically acceptable salt or solvate thereof.

17. A process for the preparation of a compound of formula (I) as defined in claim 1, or a pharmaceutically acceptable salt, tautomer, N-oxide or solvate thereof, which process comprises:

(i) the reaction of a compound of the formula (II):

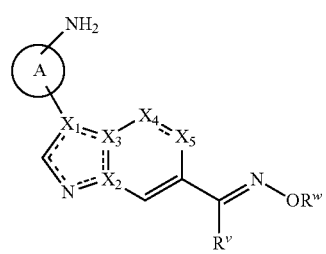

(II)

or a protected form thereof, with an appropriately substituted isocyanate or an appropriately substituted amine in the presence of carbonyl diimidazole (CDI); or (ii) the reaction of a compound of the formula (II):

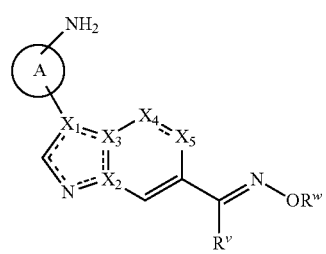

(II)

or a protected form thereof, with an appropriately substituted carboxylic acid; or (iii) the reaction of a compound of the formula (II):

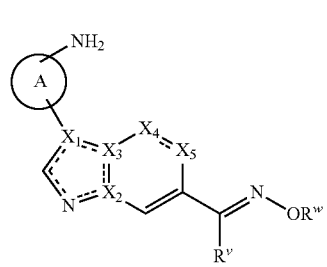

(II)

or a protected form thereof, with an appropriately substituted aldehyde or ketone; or (iv) the reaction of a compound of the formula (III):

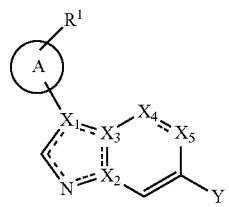

(III)

or a protected form thereof, wherein Y is a group which can be converted to an oxime of formula —$CR^v$=N—$OR^w$ e.g. ketone or aldehyde;

and then converting to an oxime of formula —$CR^v$=N—$OR^w$;

and thereafter removing any protecting group present;

wherein $X_{1-5}$, A, and $R^1$ are as defined herein; and optionally thereafter converting one compound of the formula (I) into another compound of the formula (I).

18. A pharmaceutical composition comprising a compound of formula (I) as defined in claim 1, or a pharmaceutically acceptable salt, tautomer, N-oxide or solvate thereof.

19. A method for the treatment of a disease state or condition mediated by a FGFR kinase, which method comprises administering to a subject in need thereof a compound of the formula (I) as defined in claim 1, or a pharmaceutically acceptable salt, tautomer, N-oxide or solvate thereof.

20. The method according to claim 19, wherein the disease state or condition mediated by a FGFR kinase is selected from the group consisting of pancreatic cancer, bladder carcinoma, cervical carcinoma, multiple myeloma, lung cancer, breast cancer, prostate cancer, colon cancer, liver tumor, pituitary tumor, hepatocellular carcinoma, oral squamous cell carcinoma, thyroid carcinoma, classic lobular carcinoma, urothelial carcinoma, rhabdomyosarcoma tumor, liver cirrhosis, glomerulonephritis, idiopathic pulmonary fibrosis, systemic fibrosis, and rheumatoid arthritis.

* * * * *